(12) United States Patent
Peltonen et al.

(10) Patent No.: US 6,951,928 B1
(45) Date of Patent: Oct. 4, 2005

(54) NUCLEIC ACID MOLECULE ENCODING A (POLY)PEPTIDE CO-SEGREGATING IN MUTATED FORM WITH AUTOIMMUNE POLYENDOCRINOPATHY CANDIDIASIS ECTODERMAL DYSTROPHY (APECED)

(75) Inventors: Leena Peltonen, Los Angeles, CA (US); Johanna Aaltonen, Helsinki (FI); Petra Björses, Helsinki (FI); Jaakko Perheentupa, Helsinki (FI); Aarno Palotie, Los Angeles, CA (US); Nina Horelli-Kuitunen, Helsinki (FI); Marie-Laure Yaspo, Berlin (DE); Hans Lehrach, Berlin (DE)

(73) Assignee: National Public Health Institute, Helsinki (FI)

( * ) Notice: Subject to any disclaimer, the term of this patent is extended or adjusted under 35 U.S.C. 154(b) by 0 days.

(21) Appl. No.: 09/509,595

(22) PCT Filed: Oct. 2, 1998

(86) PCT No.: PCT/EP98/06294

§ 371 (c)(1),
(2), (4) Date: Jul. 5, 2000

(87) PCT Pub. No.: WO99/18197

PCT Pub. Date: Apr. 15, 1999

(30) Foreign Application Priority Data

Oct. 2, 1997 (DE) .......................... 97 11 7154
Oct. 8, 1997 (DE) .......................... 97 11 7398
Nov. 12, 1997 (DE) .......................... 97 11 9810

(51) Int. Cl.[7] .............................................. C07H 21/00
(52) U.S. Cl. ...................... 536/23.1; 435/325; 435/320; 435/69.1; 435/70.1; 435/440; 514/44
(58) Field of Search ........................ 536/23.1; 514/44; 435/325, 440, 320, 69.1, 70.1, 320.1

(56) References Cited

U.S. PATENT DOCUMENTS 6,071,717 A * 6/2000 Klinger et al. .............. 435/69.1
6,166,180 A * 12/2000 Korenberg et al. ......... 530/350

OTHER PUBLICATIONS

Heino, M. et al. (2001) APECED mutations in the autoimmune regulator (AIRE) gene. Hum. Mutat. vol. 18, pp. 205–211. Review.*

Aaltnen J. et al. (1997) High-resolution physical and transcriptional mapping of the autoimmune polyendocrinopathy–candidiasis–ectodermal dystrophy locus on chromosome 21q22.3 by FISH. Genome Res. vol. 7, pp. 820–829.*

Bjorses P. et al. (1996)Genetic homogeneity of autoimmune polyglandular disease type I. Am. J. Hum. Genet. vol. 59, pp. 879–886.*

Pitkanen, J., et al., "Subcellular Localization of the Autoimmune Regulator Protein," *The Journal of Biological Chemistry*, vol. 276, No. 22, Jun. 1, 2002, pp. 19597–19602.

LeDouarin et al., "The N-terminal part of TIF1, a putative mediator of the ligand–dependent activation function (AF–2) of nuclear receptors, is fused to B-raf in the oncogenic protein T18," *The EMBO Journal*, 14(9):2020–2033 (1995).

Levanon et al., "Common Promoter Features in Human and Mouse Liver Type Phosphofructokinase Gene," *Biochemistry and Molecular Biology International*, 35(5):929–936 (Apr. 1995).

Aaltonen et al., "An autosomal locus causing autoimmune disease: autoimmune polyglandular disease type I assigned to chromosome 21," *Nature Genetics*, 8:83–87 (Sep. 1994).

The Finnish–German APECED Consortium, "An autoimmune disease, APECED, caused by mutations in a novel gene featuring two PHD–type zinc–finger domains,".

* cited by examiner

*Primary Examiner*—Karen Cochrane Carlson
*Assistant Examiner*—Samuel W. Liu
(74) *Attorney, Agent, or Firm*—DLA Piper Rudnick Gray Cary US LLP

(57) ABSTRACT

APECED (Autoimmune polyendocrinopathy candidiasis ectodermal dystrophy) is the only described systemic autoimmune disease with monogenic background. We have isolated a novel polynucleotide in chromosome 21q22.3 and identified five different mutations APECED patients originating from different populations. We named polypeptide, which is encoded by the said polynucleotide, APGD1 (i.e., autoimmune polyglandular disease type 1). The APGD1 polypeptide consists of 545 amino acid residues comprising two Cys(4)-His-Cys(3) double-paired finger motif similar to the PHD finger domains (zinc finger-like motifs). The identification of the polynucleotide facilitates direct genetic diagnosis of APECED and provides tools for dissection of the molecular pathogenesis of the disease.

16 Claims, 30 Drawing Sheets

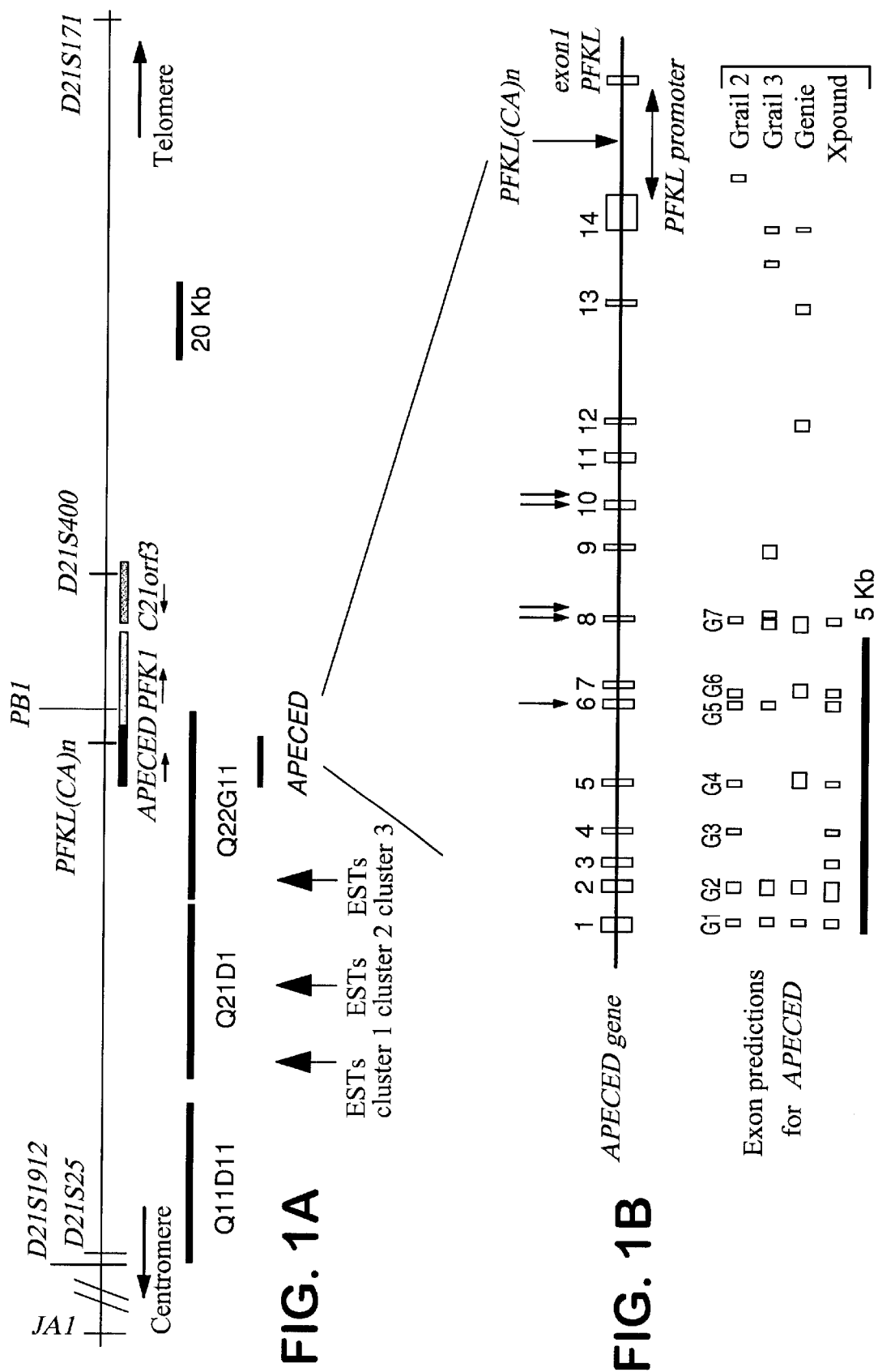

Figure 1C:
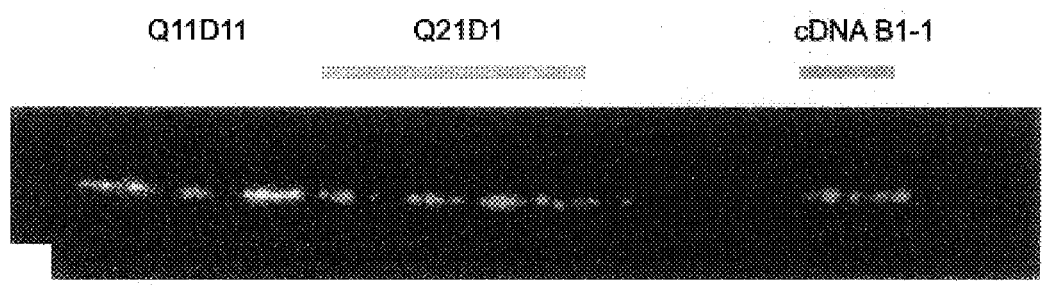

```
  1 cgggcgcacagccggcgcggaggcccacagcccgccgggacccgaggccaagcgaggg        60
 61 gctgccagtgtcccggaccccaccgcgtccgccccagcccgggtcccgcgcccaccccc       120
121 atggcgacgcggcgcgctacgcccggcttctgaggctgcaccgcgagatcgcggtg          180
  1 M  A  T  D  A  A  L  R  R  L  L  H  R  T  E  I  A  V              20
181 gccgtggacagcgccttcccactgctgcaccgcgctggctgaccacgacgtggtcccgag      240
 21 A  V  D  S  A  F  P  L  L  H  H  A  L  A  D  H  D  V  V  P  E    40
241 gacaagtttcaggagacgcttcatctgaaggaaaagagaggctgccccaggccttccac       300
 41 D  K  F  Q  E  T  L  H  L  K  E  K  R  G  C  P  Q  A  F  H        60
301 gcccctcctgtcctggctgctgaccaggactccacagccatcctggacttctggaggtg       360
 61 A  L  L  S  W  L  L  T  Q  D  S  T  A  I  L  D  F  W  R  V        80
361 ctgttcaaggactacaacctggagcgctatggccgcctgcagcccatccttgacagcttc      420
 81 L  F  K  D  Y  N  L  E  R  Y  G  R  L  Q  P  I  L  D  S  F       100
421 cccaaagatgtggaccctcagcctcagctcccagcccccagcccccggccgtccccaag       480
101 P  K  D  V  D  L  S  Q  P  R  K  G  R  K  P  P  A  V  P  K       120
481 gctttggtaccgccgccgcgcctgactccagggcaccgcagcctctcaactgaaggcc        540
121 A  L  V  P  P  P  R  L  T  P  R  G  T  A  S  P  G  S  Q  L  K  A 140
541 gccgcgccagcagcccctgacttccggagagcggcagcagcagagcagcagccacagccgg    600
141 A  A  P  A  A  P  L  T  P  R  G  T  A  S  P  G  S  Q  L  K  A    160
601 gccgcgccagcagcccctgacttccggagagcggcagcagcagagcagcagccacagccgg    660
161 A  A  P  A  A  P  L  T  P  R  G  T  A  S  P  G  S  Q  L  K  A    180
661 attcagaccatgtcagcttcagtccagagagctgtggccatgtcctccgggacgtcccg      720
181 I  Q  T  M  S  A  S  V  Q  R  A  V  A  M  S  S  G  D  V  P       200
```

FIG. 2A-1

```
721   ggagcccgaggggccgtggaggggatccctcatccagcaggtgtttgagtcaggcggctcc   780
201    G  A  R  G  A  V  E  G  I  L  I  Q  Q  V  F  E  S  G  G  S    220

781   aagaagtgcatccaggttggtgggagttctacactcccagcaagttcgaagactccggc    840
221    K  K  C  I  Q  V  G  G  E  F  Y  T  P  S  K  F  E  D  S  G    240

841   agtgggaagaacaaggcccgcagcagcagtggcccgaagcctctgttcgagccaaggga    900
241    S  G  K  N  K  A  R  S  S  S  G  P  K  P  L  V  R  A  K  G    260

901   gcccagggcgctgccccggtggaggtgaggctaggctggggcagcagggcagcgttccc    960
261    A  Q  G  A  A  P  G  G  E  V  R  L  G  W  G  E  A  R  L  G  Q  Q  G  S  V  P    280

961   gcccctctgccctccccagtgaccccagctccatctgctgtcccctcggcctgcccacctg  1020
281    A  P  L  A  L  P  S  D  P  Q  L  H  Q  K  N  E  D  E  C  A    300

1021  gtgtgtcgggacggcggggagctcatctgcctgtgacggctgcccctcggcgccttccacctg  1080
301    V  C  R  D  G  G  E  L  I  C  C  D  G  C  P  R  A  F  H  L    320

1081  gcctgcctgtcccctccgctccgggagatcccgctcgggggctgtccagctgc  1140
321    A  C  L  P  P  L  R  E  I  P  S  G  T  W  R  C  S  S  C    340

1141  ctgcaggcaacagtccaggaggtgcagccccggcagagagagccccggcccaggagca  1200
341    L  Q  A  T  V  Q  E  V  Q  P  R  A  E  E  P  R  P  Q  E  P    360

1201  cccgtggagaccccgctccccccggcttagtcggcgggagaggaggtaagaggtcca  1260
361    P  V  E  T  P  L  P  P  G  L  R  S  A  G  E  E  V  R  G  P    380

1261  cctgggaaccccctagccggcatggacacgactcttgtctacaagcacctgccggctccg  1320
381    P  G  E  P  L  A  G  M  D  T  T  L  V  Y  K  H  L  P  A  P    400

1321  ccttctgcagccccgctgcccaggccctgcaccccctgcaccccctgcctgaccctactgtgtg  1380
401    P  S  A  A  P  L  P  G  L  D  S  S  A  L  H  P  L  L  C  V    420
```

FIG. 2A-2

```
1381  ggtcctgagggtcagcagagaacctggctcctggtgcgcgttgcggggtgtgcggagatggt  1440
 421  G  P  E  G  Q  Q  N  L  A  P  G  A  R  C  G  V  C  G  D  G   440

1441  acggacgtgctgcggtgtactcactgcgccttccactggcgctgccactgccacttccca  1500
 441  T  D  V  L  R  C  T  H  C  A  A  A  F  H  W  R  C  H  F  P   460

1501  gccggcaacctcccggaccgggctgcgctgcagatcctgctcaggagacgtgacc  1560
 461  A  G  T  S  R  P  G  T  G  L  R  C  R  S  C  S  G  D  V  T   480

1561  ccagccctgtggaggggtgctggccccagcccgcctggccctgggcctgcc  1620
 481  P  A  P  V  E  G  V  L  A  P  S  P  A  R  L  A  P  G  P  A   500

1621  aaggatgacactgccagtcacgagtccgctctgcacagggatgacctggagtccttctg  1680
 501  K  D  D  T  A  S  H  E  P  A  L  H  R  D  D  L  E  S  L  L   520

1681  agcgagcacacctcgatgcatcctgcagtgggccatccagagcatgcgtccgcg  1740
 521  S  E  H  T  F  D  G  I  L  Q  W  A  I  Q  S  M  A  R  P  A   540

1741  gccccttcccctcctgacccctcagtcagctctgatgagagtgctg  1800
 541  A  P  F  P  S  *                                              546
           B1-1

1801  agaaggacaccttcctcctcagtcctcagtcctcctggatcaagaagggacag  1860

1861  cgccacctctgttgtcggctgctgtaaacagctctgtgttctgggacaccagccat  1920

1921  catgtgcctggaattaaacctgcccactctctactctgaagtcccggagcctc  1980

1981  tccttgcctggtgacctactaaaaatataaaaattagctggtggtggtgggtgcctg  2040
                           D1-1

2041  taatcccagctacatggagcctgaggcatgagaatcacttgaactcggggaggt  2100

2101  tgcagtgagctgagattgcgccactccagtctggtcggcaagagtgagactccgt  2160

2161  ctcaaaaacaaaaaccacataacataaattatcatctgaccactttcagt  2220
                          D1-1

2221  tcagtggcattcacatctcatgtaa  2245
```

FIG. 2A-3

```
mAIRE  6486 GTGTGGACTG TCACGGAAAC CCCCACGTGT GATGGAAAGT
hAIRE 19186 AAGGGGCTGG TGTGGAAAGC CCCACGGCAT GGTGGAAAGT
            --G-GG----G T----G-AA-C CCC---G---T G-TGGAAAGT mAIRE       CCAAAATTCT ACAGGAGTCT TTCTGTTGAT CTCCAGTCAG AGGCTGGGGG  6575
hAIRE       CCGAAATTCT ACAGGGGCCT CTTTGTTAAA CCTCCATGCA AGAGGCTGGG 19275
            CC-AAATTCT ACAGG-G-CT -T-TGTT-A- C---C--T--- AG----GGG
```

FIG. 13B

```
  1 ATGGCAGGTGGGGATGGAATGCTACGCCGTCTGCTGAGGCTGCACCGAGATCGCG    60
    ---------+---------+---------+---------+---------+---------+
  1 M  A  G  G  D  G  M  L  R  R  L  L  R  L  H  R  T  E  I  A    20
                        70                          110

61 GTGGCCATAGACAGTGCCTTTCCGCTGCTGCATGCTCTAGCCGACGACGTGGTCCCT   120
    ---------+---------+---------+---------+---------+---------+
 21 V  A  I  D  S  A  F  P  L  L  H  A  L  A  D  H  D  V  V  P    40
                        130                         170

121 GAGGACAAGTTCCAGGAGACGCTCCGTCTGAAGGAGAAGGAAGGCTGCCCCCAGGCCTTC   180
    ---------+---------+---------+---------+---------+---------+
 41 E  D  K  F  Q  E  T  L  R  L  K  E  K  E  G  C  P  Q  A  F    60
                        190                         230

181 CACGCCCTGCTGTCCTGGCTGCTCCTGACCCGGGACAGTGGGGCCATCCTGGATTTCTGGAGG   240
    ---------+---------+---------+---------+---------+---------+
 61 H  A  L  L  S  W  L  L  L  T  R  D  S  G  A  I  L  D  F  W  R   80
                        250                         290

241 ATTCTCTTTAAGGACTACAATCTGGAGCGGTACAGCCGCCTGCATAGCATCCTGGACGGC   300
    ---------+---------+---------+---------+---------+---------+
 81 I  L  F  K  D  Y  N  L  E  R  Y  S  R  L  H  S  I  L  D  G   100
                        310                         350

301 TTCCCAAAAGATGTGGACCTAAACCAGTCCCGGAAAGGAGAAAGCCCCTTGCTGGTCCC   360
    ---------+---------+---------+---------+---------+---------+
101 F  P  K  D  V  D  L  N  Q  S  R  K  G  R  K  P  L  A  G  P   120
```

FIG. 14-1

```
361  AAGGCCGCGGTACTGCCACCCAGACCCCCACCAAGAGAAAGCACTGGAGGAGCCTCGA  420
121   K  A  A  V  L  P  P  R  P  P  T  K  R  K  A  L  E  E  P  R   140
            430                 450                 470

421  GCCACCCCACCAGCAACTCTGGCCTCAAAGAGCGTCTCCAGCCTCCACCTGAAG       480
141   A  T  P  P  A  T  L  A  S  K  S  V  S  S  P  G  S  H  L  K   160
            490                 510                 530

481  ACTAAGCCCCCTAAGAAGCCAGATGGCAACTTGGAGTCACAGCACCTTCCTCTTGGAAAC  540
161   T  K  P  P  K  K  P  D  G  N  L  E  S  Q  H  L  P  L  G  N   180
            550                 570                 590

541  GGAATTCAGACCATGGCAGCTTCTGTCCAGAGAGCTGTGACCGTGGCCTCTGGGGATGTT  600
181   G  I  Q  T  M  A  A  S  V  Q  R  A  V  T  V  A  S  G  D  V   200
            610                 630                 650

601  CCAGGAACCCGAGGGGCCGTGGAAGGGATCCTTATCCAGCAGGTGTTTGAGTCAGGAAGA  660
201   P  G  T  R  G  A  V  E  G  I  L  I  Q  Q  V  F  E  S  G  R   220
            670                 690                 710

661  TCCAAGAAGTGCATTCAGGTTGGGGGAGAGTTTTATACACCCAACAAGTTCGAAGACCCC  720
221   S  K  K  C  I  Q  V  G  G  E  F  Y  T  P  N  K  F  E  D  P   240
```

FIG. 14-2

```
721  AGTGGCAATTTGAAGAACAAGGCCCGAGTGGTAGCAGCCTAAAGCCAGTGGTCCGAGCC  780
241   S  G  N  L  K  N  K  A  R  S  G  S  S  L  K  P  V  V  R  A   260
                  790                 800                 810

781  AAGGGAGCCCAGGTCACTATACCTGGTAGAGATGAGCAGAAAGTGGGCCAGCAGTGTGGG  840
261   K  G  A  Q  V  T  I  P  G  R  D  E  Q  K  V  G  Q  Q  C  G   280
                  850                 860                 870

841  GTTCCTCCCCTTCCATCCCTCCCCAGTGAGCCCCAGGTTAACCAGAAGAACGAGGATGAG  900
281   V  P  P  L  P  S  L  P  S  E  P  Q  V  N  Q  K  N  E  D  E   300
                  910                 920                 950

901  TGTGCCGTGTGCCACGACGGAGGTGAGCTCATCTGTTGTGACGGCTGTCCCCGGGCCTTC  960
301   C  A  V  C  H  D  G  G  E  L  I  C  C  D  G  C  P  R  A  F   320
                  970                 980                 990    1010

961  CACCTGGCTTGCCTGTCCCCACCCTGCAGGAGATCCCCAGTGGCCTCTGGAGATGCTCC  1020
321   H  L  A  C  L  S  P  P  L  Q  E  I  P  S  G  L  W  R  C  S   340
                  1030                1050                1070

1021 TGCTGCCTCCAGGGGCAGAGTCCAACAGAGAACCTGTCCCAGCCTGAGGTGTCCAGGCCCCCG  1080
341   C  C  L  Q  G  R  V  Q  Q  N  L  S  Q  P  E  V  S  R  P  P   360
```

FIG. 14-3

```
                 1090       1110       1130
1081    GAGCTACCTGCAGAGACCCCGATCCCTCGTGGGACTGAGGTCAGCTTCAGAGAAAACCAGG   1140
        ---------+---------+---------+---------+---------+---------+
 361     E  L  P  A  E  T  P  I  L  V  G  L  R  S  A  S  E  K  T  R    380
                 1150       1170       1190

1141    GGCCCATCCAGGGAGCTCAAAGCCAGTTCTGATGCTGCTGTCACATATGTGAACCTGCTG   1200
        ---------+---------+---------+---------+---------+---------+
 381     G  P  S  R  E  L  K  A  S  S  D  A  A  V  T  Y  V  N  L  L    400
                 1210       1230       1250

1201    GCCCCGCACCCTGCAGCTCCTCTGCTGGAGCCTTCAGCACTGTGCCCTCTACTGAGTGCT   1260
        ---------+---------+---------+---------+---------+---------+
 401     A  P  H  P  A  A  P  L  L  E  P  S  A  L  C  P  L  L  S  A    420
                 1270       1290       1310

1261    GGGAATGAGGGCGGGCGCCCAGGTCCAGCACCAAGCGCGGATGCCAGTGTGTGTGGCGATGGC   1320
        ---------+---------+---------+---------+---------+---------+
 421     G  N  E  G  R  P  G  P  A  P  S  A  R  C  S  V  C  G  D  G    440
                 1330       1350       1370

1321    ACCGAGGTGTTGCGTGCACACTGTGCCTTCCACTGGCGCTGCCACTTCCCG   1380
        ---------+---------+---------+---------+---------+---------+
 441     T  E  V  L  R  C  A  H  C  A  A  A  F  H  W  R  C  H  F  P    460
                 1390       1410       1430
```

FIG. 14-4

```
1381  ACGGCCGCCGCCCGGCCGGGGGACCAATCTCCGCTGCAAATCCTGCTCTGCAGACTCGACT  1440
 461   T  A  A  A  R  P  G  T  N  L  R  C  K  S  C  S  A  D  S  T   480
                            1450                1470          1490

1441  CCCACGCCAGGCACACCGGGCACCTGTACCCACCTCTGGGCCCGTCCAGCACCTGG       1500
 481   P  T  P  G  T  P  G  E  A  V  P  T  S  G  P  R  P  A  P  G   500
                            1510                1530          1550

1501  CTTGCCAAGgtagGGGGACGACTCTGCTAGTCACGACCCTGTTCTACATAGGGACGACCTG  1560
 501   L  A  K  V  G  D  D  S  A  S  H  D  P  V  L  H  R  D  D  L   520
                            1570                1590          1610

1561  GAGTCCCTCCTCAATGAGCACTCATTTGACGGCATCCTGCAGTGGGCCATCCAGAGCATG  1620
 521   E  S  L  L  N  E  H  S  F  D  G  I  L  Q  W  A  I  Q  S  M   540
                            1630                1650

1621  TCACGCCCGCTGGCCGAGACACCACCCTTCTCTTCC                            1656
 541   S  R  P  L  A  E  T  P  P  F  S  S                             552
```

FIG. 14-5

```
Human AIRE      -MATDA RR  L RLHRTEIA  VAVDSAFPLL  HALADHDVVP  EDKFQETLHL
Mouse AIRE      MAGGDGM RR  L RLHRTEIA  VAIDSAFPLL  HALADHDVVP  EDKFQETLRL
Consensus       ----D-- LRR  L RLHRTEIA  VA-DSAFPLL  HALADHDVVP  EDKFQETL-L 51                                                    100
Human AIRE      KEKEGCPQAF  HALLSWLLTQ  DSTAILDFWR  VLFKDYNLER  YGRLQPILDS
Mouse AIRE      KEKEGCPQAF  HALLSWLLTR  DSGAILDFWR  ILFKDYNLER  YSRLHSILDG
Consensus       KEKEGCPQAF  HALLSWLLT-  DS-AILDFWR  -LFKDYNLER  Y-RL--ILD- 101                                                   150
Human AIRE      FPKDVDLSQP  RKGRKPPAVP  KALVPPPRLP  TKRKASEEAR  AAAPAALTPR
Mouse AIRE      FPKDVDLNQS  RKGRKPLAGP  KAAVLPPRPP  TKRKALEEPR  ATPPATLASK
Consensus       FPKDVDL-Q-  RKGRKP-A-P  KA-V-PPR-P  TKRKA-EE-R  A--PA-L---

151                                                   200
Human AIRE      GTASPGSQLK  AKPPKKPESS  AEQQRLPLGN  GIQTMSASVQ  RAVAMSSGDV
Mouse AIRE      SVSSPGSHLK  TKPPKKPDGN  LESQHLPLGN  GIQTMAASVQ  RAVTVASGDV
Consensus       ---SPGS-LK  -KPPKKP---  -E-Q-LPLGN  GIQTM-ASVQ  RAV---SGDV 201                                                   250
Human AIRE      PGARGAVEGI  LIQQVFESGG  SKKCIQVGGE  FYTPSKFED.  SGSGKNKARS
Mouse AIRE      PGTRGAVEGI  LIQQVFESGR  SKKCIQVGGE  FYTPNKFEDP  SGNLRNKARS
Consensus       PG-RGAVEGI  LIQQVFESG-  SKKCIQVGGE  FYTP-KFED-  SG--KNKARS 251                                                   300
Human AIRE      SSGPKPLVRA  KGAQGAAPGG  GEARLGQQGS  VPAPLALPSD  PQLHQKNEDE
Mouse AIRE      GSSLKPVVRA  KGAQVTIPGR  DEQKVGQQCG  VPPLPSLPSE  PQVNQKNEDE
Consensus       -S--KP-VRA  KGAQ---PG-  -E---GQQ--  VP----LPS-  PQ--QKNEDE
```

FIG. 16-1

```
              301
Human AIRE    CAVCRDGGEL ICCDGCPRAF HLACLSPPLR EIPSGTWRCS SCLQATVQEV
Mouse AIRE    CAVCHDGGEL ICCDGCPRAF HLACLSPPLQ EIPSGLWRCS CCLQGRVQQN
Consensus     CAVC-DGGEL ICCDGCPRAF HLACLSPPL- EIPSG-WRCS -CLQ--VQ--

351                                                400
Human AIRE    QPRAEEPRPQ EPPVETPLPP GLRSAGEEVR GPPGEPLAGM DTTLVYKHLP
Mouse AIRE    LSQPEVSRPP ELPAETPILV GLRSASEKTR GPSRELKASS DAAVTYVNLL
Consensus     ---E--RP-- E-P-ETP--- GLRSA-E--R GP--E--A-- D----Y--L-

401                                                450
Human AIRE    APPSAAPLPG LDSSALHPLL CVGPEGQQNL APGARCGVCG DGTDVLRCTH
Mouse AIRE    APHPAAPL.. LEPSALCPLL SAGNEGRPGP APSARCSVCG DGTEVLRCAH
Consensus     AP--AAPL-- L--SAL-PLL --G-EG---- AP--ARC-VCG DGT-VLRC-H 451                                                500
Human AIRE    CAAAFHWRCH FPAGTSRPGT GLRCRSCSGD VTPAP.VEGV LAP.SPARLA
Mouse AIRE    CAAAFHWRCH FPTAAARPGT NLRCKSCSAD STPTPGTPGE AVPTSGPRPA
Consensus     CAAAFHWRCH FP----RPGT -LRC-SCS-D -TP-P---G- --P-S--R-A 501                                                550
Human AIRE    PGPAK..DDT ASHEPALHRD DLESLLSEHT FDGILQWAIQ SMARPAAPFP
Mouse AIRE    PGLAKVGDDS ASHDPVLHRD DLESLLNEHS FDGILQWAIQ SMSRPLAETP
Consensus     PG-AK--DD- ASH-P-LHRD DLESLL-EH- FDGILQWAIQ SM-RP-A--P 551
Human AIRE    S---
Mouse AIRE    PFSS
Consensus     ----
```

FIG. 16-2

NUCLEIC ACID MOLECULE ENCODING A (POLY)PEPTIDE CO-SEGREGATING IN MUTATED FORM WITH AUTOIMMUNE POLYENDOCRINOPATHY CANDIDIASIS ECTODERMAL DYSTROPHY (APECED)

This patent application claims foreign priority benefits. Specifically, this patent application claims the benefit of the filing date under 35 U.S.C. 120 of International Application No. PCT/EP98/06294, filed 28 Mar. 1998, and the benefit of the filing date under 35 U.S.C. 119 of Germany Application Nos. 97117154.1, filed 2 Oct. 1997.

The present invention relates to a nucleic acid molecule encoding a (poly)peptide co-segregating in mutated form with Autoimmune Polyendocrinopathy Candidiasis Ectodermal Dystrophy (APECED). In addition, the present invention relates to a mammalian, preferably murine, homologue of the above nucleic acid molecule. The present invention further relates to a nucleic acid molecule deviating by at least one mutation from the nucleic acid molecule described above wherein said mutation co-segregates with APECED and is an insertion, a deletion, a substitution and/or an inversion, and wherein said mutation further results in a loss or a gain of function of the (poly)peptide encoded by said mutated nucleic acid molecule. Furthermore, the present invention relates to a vector comprising the nucleic acid molecules described above and to a host transformed with said vector. In addition, the present invention relates to a process of recombinantly producing a (poly)peptide encoded by the nucleic acid molecules described above comprising culturing or raising said host and isolating said (poly)peptide from said culture or said host. The present invention further relates to the (poly)peptide encoded by said nucleic acid molecules or produced by the process described above. Additionally, the present invention relates to an antibody that specifically recognizes said (poly)peptides. Moreover, the present invention relates to a method for testing for a carriership for APECED or for a corresponding disease state comprising testing a sample obtained from a prospective patient or from a person suspected of carrying a predisposition for a mutation in the wild-type nucleic acid molecule described above or a mutated form of the (poly)peptide encoded by said mutated nucleic acid molecule in an immuno-assay using the antibody described above. Self tolerance and the ability to discriminate between self and non-self antigens are central to the immune response. Autoimmunity develops following a loss of self tolerance. There are several hypotheses which have been suggested, reflecting possible mechanisms leading to an autoimmune response: These hypotheses comprise:

Presentation of sequestered self antigens: immunological tolerance is not established when molecules of the body are hidden from the lymphoreticular system (e.g. in the lens of the eye, in sperm or the heart). If the tissues are damaged, an autoimmune response can develop.

Cross-reactivity: in the case when a self antigen and an exogenous antigen cross-react, the shared epitope is presented to the immune system with a different carrier, allowing T helper cells to confer a signal to B cells with antibody receptors recognizing the epitope.

Modification of auto-antigens: a modification of an auto-antigen may arise and if different, this altered antigen could be recognized as foreign and trigger an immune response.

Viral infections: auto-antibodies can sometimes arise following viral infections.

Ectopic expression of human leukocyte antigens (HLA) class II antigens: class II antigens have a restricted tissue distribution. The tissues affected in autoimmune diseases may express class II antigens inappropriately.

Regulatory defects: (1) T cells sometimes recognize self-antigens but fail to co-operate with B cells due to peripheral tolerance exerted by suppressor T cells. A failure in this regulatory mechanism could result in autoimmunity. (2) Polyclonal B cell activation: some molecules can mimic the T cell stimulus and activate B cells to divide polyclonally. This could lead to the activation of B cells secreting auto-antibodies.

There is a wide range of autoimmune diseases. The spectrum spans conditions involving a single organ through those involving all systems in the body. Autoimmune diseases are characterized by an abnormal response of the human immune system to self components. The impact of these diseases on health of populations is high since many common diseases like diabetes mellitus, multiple sclerosis or rheumatoid arthritis represent autoimmune reactions. Censequently, characterization of molecules involved in autoimmunity are of high importance for the cure and treatment of these disorders.

Autoimmune polyendocrinopathy candidiasis ectodermal dystrophy (APECED, OMIM 240300) is an autosomal recessive disease characterized by 1) autoimmune polyendocrinopathies: hypoparathyroidism, adrenocortical failure, IDDM, gonadal failure, hypothyroidism, pernicious anemia, and hepatitis, 2) chronic mucocutaneous candidiasis and 3) ectodermal dystrophies: vitiligo, alopecia, keratopathy, dystrophy of dental enamel, nails and tympanic membranes (Ahonen, P., et al., *N. Engl. J. Med.,* 322, 1829–1836 (1990)). The disease is reported worldwide but is exceptionally prevalent among the Finnish population (incidence 1: 25 000) and the Iranian Jews (Ahonen, P., et al., *N. Engl. J. Med.,* 322, 1829–1836 (1990); Zlotogora, J., et al., *J. Med. Genet.,* 29, 824–826 (1992)). The primary biochemical defect in this disorder remains elusive.

APECED is the only described systemic autoimmune disease in humans with Mendelian inheritance, and the clinical phenotype characterized by autoimmune endocrinopathies, including IDDM, and chronic candidiasis would suggest defects in both humoral (Ahonen, P., et al., *J. Clin. Endocrinology and Metabolism,* 64, 494–500 (1987)) and cell mediated immunity (Fidel, P. L. & Sobel, J. D., *TIMB,* 2, 202–206 (1994)). No single HLA associated haplotype exists (Ahonen, P., et al., *J. Clin. Endocrinology and Metabolism,* 66, 1152–1157 (1988)), autoantibodies are found against several cell types in the patients' sera (Ahonen, P., et al., *J. Clin. Endocrinology and Metabolism,* 64, 494–500 (1987)) and only unspecific abnormal responses have been found in T cell proliferation tests. These observations would suggest a deregulation of both B and T cell specific immune responses in APECED. Moreover, the non-specific autoantibodies detected in the APECED patients' sera against several cell types do not support the hypothesis of one major autoantigen (Krohn, K., et al., *Lancet,* 339, 770–773 (1992)). However, despite these well defined characteristics, the etiology of APECED, like of most autoimmune diseases, remains unknown. Insights into said etiology would also provide an entry point for the dissection of molecular mechanisms leading to the development of autoimmunity in general. On the basis of such knowledge, means and methods for the prevention or treatment of autoimmune diseases in general and APECED in particular might be developed.

Accordingly, the technical problem underlying the present invention was to uncover factors involved in the development of APECED that might contribute to providing means of treating or curing monogenic autoimmune diseases, in particular APECED.

The solution to the above technical problem is achieved by providing the embodiments characterized in the claims.

Accordingly, in one aspect the present invention relates to a nucleic acid molecule encoding a (poly)peptide co-segregating in mutated form with Autoimmune Polyendocrinopathy Candidiasis Ectodermal Dystrophy (APECED) which is (a) a nucleic acid molecule comprising a nucleic acid molecule encoding the (poly)peptide having the amino acid sequence of FIG. 2A;

(b) a nucleic acid molecule comprising the nucleic acid molecule having the nucleotide sequence of FIG. 2A that encodes the amino acid sequence of FIG. 2A;

(c) a nucleic acid molecule hybridizing to the nucleic acid molecule of (a) or (b); or (d) a nucleic acid molecule which is degenerate to the nucleic acid molecule of (c).

The present invention surprisingly revealed that a novel polypeptide, designated APGD1 for autoimmune poly glandular disease type 1, encoded by the nucleic acid molecule of the invention co-segregates in mutated form with APECED. As used throughout the present specification the term "APGD1" and the term "AIRE" denote the same (poly)peptide and are used interchangeably.

As used herein, the term "co-segregation" relates to any association of the mutated form of the polypeptide with APECED. APGD1 is a protein with a predicted length of 545 amino acids, a theoretical molecular weight of 57.7 kD and a calculated pI of 7.53. Statistical analysis of the protein sequence of FIG. 2A (Brendel, V., et al., *Proc. Natl. Acad. Sci. USA*, 89, 2002–2006 (1992)) indicates a high content of proline (11.7%) but no apparent clusters of charged amino acids or periodicity patterns. The secondary structural content of APGD1 was predicted to consist mostly of coils, with only a weak probability for the occurrence of structural α-helices or β-sheets. A putative bi-partite nuclear targeting signal (Dingwall, C. & Laskey R. A., *TIBS*, 16, 478–481 (1991)) was found between amino acids 113 to 133 (FIG. 2A). The predicted protein harbors two cysteine-rich regions of 42 amino acids, each specifying a Cys4-His-Cys3 double-paired finger motif similar to the PHD finger type (Aasland, R., et al., *TIBS*, 20, 56–59 (1995)) (FIG. 2A). Spacing of essential residues is conserved in the two motifs found in APGD1: $C_{299,434}$-XX-$C_{302,437}$-X(8)-$C_{311,446}$-XX-$C_{314,449}$-X(4)-$H_{319,454}$-XX-$C_{322,471}$-XX-$C_{340,474}$ (where X is any amino acid and numbers in parenthesis represent the length of the intervening peptide sequence). This structural motif has been reported for a number of nuclear proteins involved in the mediation or regulation of transcription, such as TIF1 (Transcription Intermediary Factor 1) (Douarin, Le, B., et al., *EMBO J.*, 14, 2020–2033 (1995)) and KRIP-1 (KRAB-A Interacting Protein)(Kim, S-S., et al., *Proc. Nal. Acad. Sci. USA*, 13, 15299–14304 (1996)). Sequence homology of APGD1 with other proteins in the databases was strictly limited to this Cys4-His-Cys3 motif. Although the spacing of residues is conserved in each case, the sequence is most closely homologous to the Mi-2 autoantigen (Ge, Q., et al., *J. Clin. Invest.*, 96, 1730–1737 (1995)) and the TIF1 protein (Thenot, S., et al., *J. Biol. Chem.*, 272, 12062–12068 (1997)). Mi-2 is the major nuclear antigen detected in the sera of autoimmune dermatomyositis patients (Ge, Q., et al., *J. Clin. Invest.*, 96, 1730–1737 (1995)) and TIF1 is involved in the transcriptional control of the estrogen receptor (Thenot, S., et al., *J. Biol. Chem.*, 272, 12062–12068 (1997)).

By the provision of the nucleotide acid molecule of the invention it is now possible to isolate identical or similar nucleic acid molecules which code for proteins with identical functions and characteristics and which are derived from other individuals or which represent alleles of the nucleic acid molecule of the invention. Well-established approaches for the identification and isolation of such related sequences are, e.g., the isolation from genomic or cDNA libraries using the complete part of the disclosed sequence as a probe or the amplification of corresponding nucleic acid molecules by polymerase chain reaction using specific primers.

As stated hereinabove, the invention also relates to nucleic acid molecules which hybridize to the above described nucleic acid molecules and differ at one or more positions in comparison to these as long as they encode a (poly)peptide having the above described characteristics. In connection with the present invention, the term "hybridizing" is understood as referring to conventional hybridization conditions, preferably such as hybridization in 50% formamide, 6×SSC, 0.1% sodium dodecyl sulfate (SDS), and 100 μg/ml single stranded DNA (ssDNA), in which temperatures for hybridization are above 37° C. and temperatures for washing in 0.1×sodium chloride citrate (SSC), 0.1% SDS are above 55° C. Most preferably, the term "hybridizing" refers to stringent hybridization conditions, for example such as described in Sambrook, et al. (Molecular cloning; A Laboratory Manual, Second Edition, Cold Spring Harbor Laboratory Press, Cold Spring Harbor N.Y. (1989)) or Higgins & Hames (Nucleic acid hybridization, A practical approach, IRL Press, Oxford (1985)). Said nucleic acid molecules comprise those which differ, for example, by deletion(s), insertion(s), alteration(s) or any other modification known in the art in comparison to the above described nucleic acid molecules. Methods for introducing such modifications in the nucleic acid molecules according to the invention are well-known to the person skilled in the art; see, e.g., Sambrook, et al., supra.

As mentioned hereinabove, the invention also relates to nucleic acid molecules the sequence of which differs from the sequence of the above-described hybridizing molecules due to the degeneracy of the genetic code.

In a preferred embodiment of the nucleic acid molecule of the present invention, said (poly)peptide has the function of a transcription factor or a transcription-associated factor. As used herein, the term "transcription factor" or "transcription-associated factor" comprises any factor which directly or indirectly influences transcription of a gene by, e.g., directly interacting with regulatory sequences, interacting with other transcription regulating factors, changing the conformation of chromatin, and the like.

The (poly)peptide encoded by the nucleic acid molecule of the invention preferably comprises at least one zinc finger motif. The term "zinc finger" describes a certain amino acid motif, which is able to bind metal ions, and is well known for those skilled in the art. Preferably, the (poly)peptide of the invention comprises two double-paired zinc finger motifs. Comprised by the present inventions are furthermore embodiments of nucleic acid molecules that specify polymorphisms of the above identified locus which correlate with APECED. Said polymorphisms may or may not lead to amino acid substitutions. Polymorphisms can be tested for according to conventional procedures.

In yet another aspect, the present invention relates to a mammalian homologue of the nucleic acid molecule(s) of the present invention. The person skilled in the art knows on the basis of the teachings of the present invention how to obtain the homologue, e.g., of other mammals such as mouse, rat, rabbit or pig. This can be effected, e.g., by hybridization of the molecule of the present invention under low stringent conditions to the corresponding nucleic acids from other species contained, e.g., in conventional libraries. "Low stringent conditions" differ from stringent conditions (described hereinabove) in that higher salt concentrations and/or lower temperatures are employed for hybridization. Such conditions are well known in the art (see, e.g., Sambrook et al. or Higgins & Hames, supra).

In a preferred embodiment said mammalian homologue is a murine homologue.

In a most preferred embodiment said murine homologue is a nucleic acid molecule which is (a) a nucleic acid molecule comprising a nucleic acid molecule encoding the (poly)peptide having the amino acid sequence of FIG. 14;
(b) a nucleic acid molecule comprising the nucleic acid molecule having the nucleotide sequence of FIG. 14 that encodes the amino acid sequence of FIG. 14;
(c) a nucleic acid molecule hybridizing to the nucleic acid molecule of (a) or (b); or
(d) a nucleic acid molecule which is degenerate to the nucleic acid molecule of (c).

The murine homologue of the nucleic acid molecule of the present invention may be advantageously used to develop an animal model for APECED. Based on this animal model it is envisaged in accordance with the present invention to dissect the events which lead to the development of APECED. This may ultimately lead to the development of e.g. pharmaceutical compositions for preventing and/or treating this autoimmune disease.

In a further embodiment, the present invention relates to a nucleic acid molecule deviating by at least one mutation from the nucleic acid molecules described above, wherein said mutation co-segregates with APECED and is
(a) an insertion;
(b) a deletion;
(c) a substitution; and/or
(d) an inversion,
and wherein said mutation further results in a loss of function or a gain of function of the (poly)peptide of the invention.

Especially with respect to insertions and deletions, it could be shown in accordance with the present invention that such mutations may lead to a frame shift which in turn leads to the expression of a truncated form of the (poly) peptide of the present invention.

The term "substitution", as used herein, also includes point mutations resulting in an amino acid exchange. Examples of specific point mutations are given herein below. However, such point mutations may also lead to the creation of nonsense codons, i.e. stop codons, which lead to premature termination of translation and, thus, to truncated forms of the (poly)peptide of the present invention.

In a preferred embodiment of the present invention, said insertion, which is a duplication of 4 nucleotides (CCTG) normally found at position 1086–1089, is a 4 nucleotide insertion at the nucleotide position 1085 or 1090, an insertion of an adenosine at position 1284, or an insertion of a cytosine at position 1365 of the nucleotide sequence of FIG. 2A.

In another preferred embodiment of the invention, said deletion is a 13 nucleotide deletion of nucleotides 1085–1097, a deletion of the thymidine at position 1051 or a deletion of the cytosine at position 1309 or 1313 of the nucleotide sequence of FIG. 2A.

In still another preferred embodiment of the present invention, said substitution is a cytosine to thymidine exchange at nucleotide position 889 a guanosine to thymidine exchange at nucleotide position 358, an adenosine to guanosine exchange at nucleotide position 374, a guanosine to adenosine exchange at nucleotide position 1052, or a cytosine to adenosine exchange at nucleotide position 1094 of the nucleotide sequence of FIG. 2A.

As mentioned above, said mutation results in a loss or a gain of function of the (poly)peptide of the invention. In a preferred embodiment of the present invention, said loss of function is a loss of macromolecule binding properties. However, a loss of transactivating property in addition or instead of the loss of the macromolecule binding property is also envisaged. Other possibilities relate to the loss of a structural determinant (truncated protein) in addition to the loss of a functional determinant.

For example, the experiments performed in accordance with the present invention suggest that at least some of the mutations identified so far in the AIRE gene lead to truncated forms of the (poly)peptide of the present invention lacking at least one of the PHD zinc fingers. Based on the cellular localization studies performed in accordance with the present invention (for details see Examples 10 to 12) it is, furthermore, envisaged in accordance with the present invention, but without being bound to any scientific theory, that loss of function of the mutated/truncated (poly)peptides of the invention may be associated with their abnormal nuclear distribution. Thus, it is conceivable that the truncated (poly)peptides of the invention are erroneously directed to other nuclear structures by default as consequence of missing a domain normally interacting with either a core DNA target or chromatin-associated protein. In addition, it could be shown in accordance with the present invention that AIRE interacts with structural components of the cytoplasmic compartment. More specifically, it is an envisaged that AIRE associates with vimentin since AIRE harbors a cluster of basic amino acids within the nuclear targeting signal. Moreover, the apparently variable temporal and spatial decoration of filament arrays and nuclear speckles by anti-AIRE antibodies suggests the existence of a dynamic or passive trafficking of AIRE in the cell. Thus, it is also envisaged in accordance with the present invention that AIRE is residing on vimentin fibers as part of a docking mechanism regulating nuclear translocation. The occurrence of nuclear factors interacting with components of the cytoskeleton is not an unprecedented observation. An interesting example is the regulation of the function of Gli zinc finger transcription factor, vertebrate homologue of *Drosophila* ci gene (Biesecker, L. G. (1997). Strike three for GLI3 [published erratum appears in Nat Genet 1998 Jan; 18(1) :88]. *Nature Genetics* 17, 259–260). This transcription factor is mainly tartgeted to the cytoplasm where it is anchored to microtubules, whereas a truncated form of Gli processed by proteolytic cleavage of the molecule is directed to the nucleus (Aza-Blanc, P., Ramirez-Weber, F. A., Laget, M. P., Schwartz, C. & Kornberg, T. B. (1997). Proteolysis that is inhibited by hedgehog targets Cubitus interruptus protein to the nucleus and converts it to a repressor. *Cell* 89, 1043–1053; Robbins, D. J., Nybakken, K. E., Kobayashi, R., Sisson, J. C., Bishop, J. M. & Therond, P. P. (1997). Hedgehog elicits signal transduction by means of a large complex containing the kinesin-related protein costal2. *Cell* 90, 225–234). To date, the only described nuclear factor interacting with vimentin is a protein component of the nuclear matrix, NMP125, transiently stored along vimentin during mitosis (Marugg, R. A. (1992). Transient storage of a nuclear matrix protein along intermediate-type filaments during mitosis: a novel function of cytoplasmic intermediate filaments. *Journal of Structural Biology* 108, 129–139). Thus, AIRE represents the first example of a zinc-finger protein co-localizing with vimentin intermediate filaments. With respect to the abnormal cytoplasmic localization, it is thus envisaged that loss of function may be associated with impaired protein-protein interactions involved in maintaining the shape and integrity of intermediate filaments. In other words, aggregates of the mutant (poly)peptides of the present invention may prevent the formation of vimentin intermediate filaments by, e.g., entrapping vimentin. On the other hand, it may also be envisaged that the abovementioned docking/activation mechanism of the mutant (poly)peptides of the invention is impaired threby leading to a loss of function. Thus, the pathological consequences of at least some of the mutations found in the AIRE gene may elicit their effects at least in part by effecting the spatial organization of AIRE in the cell.

In an alternative preferred embodiment of the present invention, said gain of function is involved in molecular interaction. An example of such a gain of function is the indirect regulation of a cellular process. For instance, if the deletion of a zinc finger results in the loss of a binding property involving a second molecule, this second molecule may "gain" a function in case its function was modulated by APGD1.

The present invention further relates to a fragment of any of the aforementioned nucleic acid molecule(s) comprising at least 14 nucleotides. Preferably, said fragment is about 17 nucleotides long, and most preferably, it is about 21 nucleotides long. Said fragment can be used, e.g., as a probe in nucleic acid hybridization experiments like, e.g., Southern or Northern blot experiments, or as primer in primer extension analyses. In a preferred embodiment said fragment is labeled.

In another aspect, the present invention provides a nucleic acid molecule which is complementary to any of the nucleic acid molecules or fragments thereof described above. Such a nucleic acid molecule can be used, e.g., as a probe in RNase protection assays, or as an anti-sense probe to inhibit expression of the (poly)peptide(s) of the present invention. The person skilled in the art is familiar with the preparation and the use of said probes (see, e.g., Sambrook et al., supra).

In a further embodiment of the present invention, the nucleic acid molecule(s) of the invention are DNA molecules like, e.g., cDNA or genomic DNA molecules, or RNA molecules like mRNA molecules.

In another embodiment, the present invention provides a primer pair which hybridizes under stringent conditions to any of the nucleic acid molecules mentioned above. Said primer pair can be used, e.g., in a polymerase chain reaction (PCR) to amplify nucleic acid fragments derived from the nucleic acid molecules described above. In the case that RNA is used as the template in the amplification reaction, it is beforehand reverse transcribed into DNA. The skilled artisan knows how to design and use said primer pair, which conditions for the amplification reaction have to be set up, and how to reverse transcribe RNA into DNA (see, e.g., Sambrook et al., supra).

Furthermore, the present invention relates to a vector comprising a nucleic acid molecule of the invention.

Examples for such vectors are, e.g., plasmids like, e.g., pUC18/19, pBR322 or pBlueScript all of which are commercially available. In addition, vectors of the present invention may be cosmids, viruses or bacteriophages used conventionally in genetic engineering that comprise the nucleic acid molecule of the invention. Preferably, said vector is a gene transfer or targeting vector. Such vectors may comprise further genes such as marker genes which allow for the selection of said vector in a suitable host cell and under suitable conditions. In another preferred embodiment the nucleic acid molecule present in the vector is operatively linked to regulatory elements permitting expression in prokaryotic or eukaryotic host cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and, optionally, a poly-A signal ensuring termination of transcription and stabilization of the transcript, and/or an intron further enhancing expression of said polynucleotide. Additional regulatory elements may include transcriptional as well as translational enhancers, and/or naturally-associated or heterologous promoter regions. Possible regulatory elements permitting expression in prokaryotic host cells comprise, e.g., the PL, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the nucleic acid molecule of the invention. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCDM8, pRc/CMV, pcDNA1, pcDNA3 (In-vitrogene), pSPORT1 (GIBCO BRL)) or pCI (Promega).

Preferably, the expression control sequences will be eukaryotic promoter systems in vectors capable of transforming or transfecting eukaryotic host cells, but control sequences for prokaryotic hosts may also be used. As mentioned above, the vector of the present invention may also be a gene transfer or targeting vector. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art; see, e.g., Giordano, Nature Medicine 2 (1996), 534–539; Schaper, Circ. Res. 79 (1996), 911–919; Anderson, Science 256 (1992), 808–813; Isner, Lancet 348 (1996), 370–374; Muhlhauser, Circ. Res. 77 (1995), 1077–1086; Wang, Nature Medicine 2 (1996), 714–716; WO94/29469; WO 97/00957 or Schaper, Current Opinion in Biotechnology 7 (1996), 635–640, and references cited therein. The polynucleotides and vectors of the invention may be designed for direct introduction or for introduction via liposomes, or viral vectors (e.g. adenoviral, retroviral) into the cell. Preferably, said cell is a gern line cell, embryonic cell, or egg cell or derived therefrom, most preferably said cell is a stem cell.

The invention also relates to a host comprising a vector according to the invention. The transformation of hosts with the vectors of the invention is well known in the art (see, e.g., Sambrook et al., supra). Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook et al., Molecular Cloning A Laboratory Manual, Cold Spring Harbor Laboratory (1989) N.Y. and Ausubel et al., Current Protocols in Molecular Biology, Green Publishing Associates and Wiley Interscience, N.Y. (1989). Alternatively, the polynucleotides and vectors of the invention can be reconstituted into liposomes for delivery to target cells. The vectors containing the polynucleotides of the invention can be transferred into the host cell by well-known methods, which vary depending on the type of cellular host. For example, calcium chloride transfection is commonly utilized for prokaryotic cells, whereas, e.g., calcium phosphate or DEAE-Dextran mediated transfection or electroporation may be used for other cellular hosts; see Sambrook, supra.

In a preferred embodiment of the present invention, the host is a bacterium, a yeast cell, an insect cell, a fungal cell, a mammalian cell, a plant cell, a transgenic animal or a transgenic plant. As used herein, the term "transgenic" also relates to organisms that contain a gene which has been knocked out. For example, animals with no functional allele of the APGD1-gene can be used for the investigation of the role APGD-1 plays in cellular life as well as a model for the development of APECED. Techniques for the production of transgenic or knock-out organisms are well known in the art.

In a further embodiment, the present invention relates to a process of producing a (poly)peptide of the invention comprising culturing or raising the host described above and isolating said (poly)peptide from said culture or said host. Such methods are well known in the art (see, e.g., Sambrook et al., supra).

Furthermore, the invention relates to a (poly)peptide encoded by a nucleic acid molecule of the invention or produced by the above described process. In this context it is also understood that the (poly)peptides according to the invention may be further modified by conventional methods known in the art. By providing the (poly)peptides according to the present invention it is also possible to determine the portions relevant for their biological activity. This may allow the construction of chimeric proteins or fusion proteins comprising an amino acid sequence derived from a (poly)peptide of the invention which is crucial for its biological activity and other functional amino acid sequences like, e.g., nuclear localization signals, transactivating domains, DNA-binding domains, hormone-binding domains, protein tags glutathione S-transferase (GST), Green Fluorescent Protein (GFP), h-myc peptide, Flag, histocompatability antigen (HA) peptide) which may be derived from the same or from heterologous proteins. Said chimeric or fusion proteins are also comprised by the present invention.

The present invention also relates to a compound derived from a (poly)peptide of the invention and having essentially the same three dimensional structure thereof. Said compounds can be theoretically constructed on computers using molecular modelling software and subsequently be synthesized. Since such compounds are preferably not of proteinaceous nature, they may be used in applications where proteolytic degradation should be avoided, e.g., when contained in pharmaceutical compositions that are applied orally. The design of such compounds may, e.g., be effected by peptidomimetics.

In a further embodiment, the present invention relates to an antibody that specifically recognizes the (poly)peptide of the invention. Namely, the invention relates to an antibody which specifically recognizes (poly)peptides according to the invention irrespective of whether they are the wild-type or a mutated form and/or depending on whether the (poly)peptide of the invention is the wild-type or a mutated form. The antibody of the present invention may be a monoclonal antibody, a polyclonal antibody or a synthetic antibody as well as a fragment of said antibodies, such as, e.g., a Fab, a Fv or a scFv fragment. Furthermore, the antibody or fragments thereof can be obtained by using methods which are described, e.g., in Harlow and Lane, "Antibodies, A Laboratory Manual", CSH Press, Cold Spring Harbor, 1988. The antibody of the present invention can be used, e.g., for the immunoprecipitation and immunolocalization of the (poly)peptides of the invention as well as for the monitoring of the presence of such (poly)peptides, e.g., in recombinant organisms, and for the identification of compounds interacting with the (poly)peptides according to the invention.

Moreover, the present invention relates to a pharmaceutical composition comprising at least one of the aforementioned nucleic acid molecules, vectors, (poly)peptides, three-dimensionally equivalent compounds, and/or the antibody according to the present invention either alone or in combination, and optionally a pharmaceutically acceptable carrier. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by conventional methods. The pharmaceutical compositions can be administered to the subject at a suitable dose. Administration of the suitable compositions may be effected by different ways, e.g. by intravenous, intraperitoneal, subcutaneous, intramuscular, topical or intradermal administration. The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Generally, the regimen as a regular administration of the pharmaceutical composition should preferably be in the range of 1 μg to 10 mg units per day. If the regimen is a continuous infusion, it should preferably also be in the range of 1 μg to 10 mg units per kilogram of body weight per minute, respectively. Progress can be monitored by periodic assessment. Dosages will vary but a preferred dosage for intravenous administration of DNA is preferably from approximately $10^6$ to $10^{22}$ copies of the DNA molecule. The compositions of the invention may be administered locally or systemically. Administration will generally be parenterally, e.g., intravenously; DNA may also be administered directly to the target site, e.g., by biolistic delivery to an internal or external target site or by catheter to a site in an artery.

In addition, the present invention relates to a diagnostic composition comprising at least one of the aforementioned nucleic acid molecules, vectors, (poly)peptides, three-dimensionally equivalent compounds, and/or the antibody according to the present invention either alone or in combination.

Said diagnostic composition can be used to test for a carriership for APECED or for a corresponding disease state comprising testing a sample obtained from a prospective patient or from a person suspected of carrying a predisposition for a mutation in the nucleic acid molecule(s) of the invention. Furthermore, the diagnostic composition can be used to test for a carriership for APECED or for a corresponding disease state comprising testing a sample obtained from a prospective patient or from a person suspected of carrying a predisposition for a mutated form of the (poly) peptide(s) according to the invention in an immuno-assay using the antibody of the invention. The term "immuno-assay", as used herein, comprises methods like, e.g., immuno-precipitation, immuno-blotting, ELISA, RIA, indirect immuno-fluorescence experiments, and the like. Such techniques are well known in the art and are described, e.g. in Harlow and Lane, supra.

The components of the composition of the invention may be packaged in containers such as vials, optionally in buffers and/or solutions. If appropriate, one or more of said components may be packaged in one and the same container.

In another embodiment, the present invention relates to methods for testing for a carriership for APECED or for a corresponding disease state comprising testing a sample obtained from a prospective patient or from a person suspected of carrying a predisposition for a mutation in the nucleic acid molecule(s) of the invention. Such methods comprise, e.g., Southern blotting or amplifying nucleic acid molecules from a nucleic acid obtained from a prospective patient or from a person suspected of carrying a predisposition for APECED with the primer pair of the invention, and analyzing the amplified nucleic acid molecules for the presence of a mutation. Said nucleic acid molecules can be analyzed, e.g., by sequencing with the primer or probe of the invention, hybridizing with the primer of the invention or by size-fractionating said nucleic acid molecules by gel-electrophoresis. Alternatively, and by way of example said nucleic acid obtained from a prospective patient or from a person suspected of carrying a predisposition for APECED can be directly analyzed by sequencing or hybridizing with the primer or probe of the invention. All the above mentioned primers or probes may hybridize to a mutated or a wild-type sequence. Further, all of the aforedescribed methods are well known in the art (see, e.g., Sambrook et al., supra).

In yet another embodiment, the present invention relates to methods for testing for a carriership for APECED or for a corresponding disease state comprising testing a sample obtained from a prospective patient or from a person suspected of carrying a predisposition for a mutated form of the (poly)peptide(s) according to the invention. Such methods comprise, e.g., immuno-precipitation, immuno-blotting, enzyme liked immunosorbent assay (ELISA), radioimmunoassay (RIA), indirect immuno-fluorescence experiments, and the like. Such techniques are well known in the art and are described, e.g. in Harlow and Lane, supra.

In another embodiment, the present invention relates to the use of the nucleic acid molecule(s) or the vectors of the invention for gene therapy. Vectors comprising a nucleic acid molecule of the invention may be stably integrated into the genome of the cell or may be maintained in an extra-chromosomal form. On the other hand, viral vectors described in the prior art may be used for transfecting certain cells, tissues or organs. Suitable gene delivery systems may include liposomes, receptor-mediated delivery systems, naked DNA, and viral vectors such as herpes viruses, retroviruses, adenoviruses, and adeno-associated viruses, among others. Delivery of nucleic acid molecules to a specific site in the body for gene therapy may also be accomplished using biolistic delivery systems.

Standard methods for transfecting cells with nucleic acid molecules are well known to those skilled in the art, see, e.g., Sambrook et al., supra. Gene therapy to cure APECED may be carried out by directly administering the nucleic acid molecule of the invention encoding a functional form of APGD1 to a patient or by transfecting cells with said nucleic acid molecule of the invention ex vivo and infusing the transfected cells into the patient. Furthermore, research pertaining to gene transfer into cells of the germ line is one of the fastest growing fields in reproductive biology. Gene therapy, which is based on introducing therapeutic genes into cells by ex-vivo or in-vivo techniques is one of the most important applications of gene transfer. Suitable vectors and methods for in-vitro or in-vivo gene therapy are described in the literature and are known to the person skilled in the art. The nucleic acid molecules comprised in the pharmaceutical composition of the invention may be designed for direct introduction or for introduction via liposomes, or viral vectors (e.g. adenoviral, retroviral) containing said nucleic acid molecule into the cell. Preferably, said cell is a germ line cell, embryonic cell, or egg cell or a cell derived therefrom, if the production of transgenic non-human animals is envisaged.

It is to be understood that the introduced nucleic acid molecule encoding the protein having the biological activity of APGD1 expresses said protein after introduction into said cell and preferably remains in this status during the lifetime of said cell. For example, cell lines which stably express said protein having the biological activity of APGD1 may be engineered according to methods well known to those skilled in the art. Rather than using expression vectors which contain viral origins of replication, host cells can be transformed with the recombinant DNA molecule or vector of the invention and a selectable marker, either on the same or separate vectors. Following the introduction of foreign DNA, engineered cells may be allowed to grow for 1–2 days in an enriched media, and then are switched to a selective media. The selectable marker in the recombinant plasmid confers resistance to the selection and allows for the selection of cells having stably integrated the plasmid into their chromosomes and growing to form foci which in turn can be cloned and expanded into cell lines. This method may advantageously be used to engineer cell lines which express the protein having the biological activity of APGD1. A number of selection systems may be used, including but not limited to the herpes simplex virus thymidine kinase, hypoxanthine-guanine phosphoribosyltransferase, and adenine phosphoribosyl-transferase in tk, hgprt or aprt cells, respectively. Also, antimetabolite resistance can be used as the basis of selection for dhfr, which confers resistance to methotrexate, gpt, which confers resistance to mycophenolic acid, neo, which confers resistance to the aminoglycoside G-418, hygro, which confers resistance to hygromycin, or puromycin (pat, puromycin N-acetyl transferase). Additional selectable genes have been described, for example, trpB, which allows cells to utilize indole in place of tryptophan; hisD, which allows cells to utilize histinol in place of histidine, and ODC (ornithine decarboxylase) which confers resistance to the omithine decarboxylase inhibitor, 2-(difluoromethyl)-DL-omithine, DFMO.

The documents cited in the present specification are herewith incorporated by reference.

The figures show:

FIG. 1

A) The physical map of the APECED region showing the markers used to construct the disease haplotypes (cen—JA1, D21S1912, PFKL (CA$_n$), PB1, D21S171—tel), the other genes (PFKL, green and 694N10, pink) and the ESTs (EST cluster 1: AA082879, AA085392, EST cluster 2: N67176, T84071, T86112, T79577, T79655, R23544, R44295, EST cluster 3: AA453553) located in the close vicinity of APGD1 (SEQ ID NOS.: 1–2)(blue) and the key cosmid clones Q21D11 and Q22G11 used for genomic sequencing as well as cosmid clone Q11D11 that was used as orientation marker in the fiber FISH experiment (see FIG. 1C).

B) The genomic structure of the APGD1 gene. The 14 true exons of the gene are compared with the gene models predicted with different gene finding programs (Uberbacher, E., et al., *Proc. Natl. Acad. Sci, USA,* 88, 11261–1265 (1991); Thomas, A., & Skolnick, M. H., *IMA J. Math. Appl. Med. Biol.,* 11, 149–160 (1994); Kulp, D., et al., ISMB-96, St. Louis, Mo., AAAI/MIT Press. (available on the worldwide web at hgc.lbl.gov/projects/genie.html) (1996)). Solid boxes indicate exons in which at least one boundary was correctly predicted, open boxes are false exons. Genomic sequence of cosmid clones Q21D1, Q22G11, EST matches, detailed gene prediction data and the intron-exon boundaries of APGD1 are available on the internet at http://chr21.rz-berlin.mpg.de.(ADECED.html/.

C) Fiber FISH image showing the assignment of the APGD1, red signal, (cDNA clone B1-1 used as a probe) in relation to previously mapped cosmid clones, Q11D11 (yellow) and Q21D1 (green). Detailed protocol is described elsewhere (Heiskanen, M., et al., *TIG,* 10, 379–382 (1996)).

FIG. 2

A) The nucleotide and predicted amino acid sequence of human APGD1. The boundaries corresponding to the composite cDNA sequence are indicated by brackets, the most 3' end nucleotides for cDNA clones B1-1 and D1-1 are at positions 1809 and 2181, respectively. The last 64 nucleotides were determined by PCR extension. A putative non-canonical polyadenylation signal was found at nucleotide 2191 (underlined). The Alu sequence overlapping with the PFKL promotor is starting at nucleotide 1995 (arrowed bracket). Silent polymorphisms are indicated by small arrows (nucleotides 708, 801, 1317 and 1698). The predicted protein is 545 amino acids. The putative bi-partite nuclear localisation signal is underlined in blue. The two PHD zinc finger domains are underlined in magenta. The cDNA sequence has been deposited in EMBL (Accession No. Z97990). B) Northern blot analysis using cDNA B1-1 (1,8 kb) as a probe on a multiple tissue Northern blot, each lane containing 2 µg poly(A) RNA from human adult tissues (Clontech catalog # 7754-1 and 7751-1). The lower panel shows the hybridization with the β-globin control probe.

FIG. 3

The mutations in the APGD1 gene (see also Table 1). A) The C-lanes of the sequencing gel showing a patient homozygous for the Finnish major mutation and a normal control. $C_{889}$ of the patient has been mutated to T. B) A-lanes of a normal control and a Finnish patient heterozygous for the haplotype 4.1 show an A insertion at position 1284. C) Homozygous deletion of $C_{1313}$ is observed in C-lane of the sequence of a French patient also homozygous for the disease haplotype 5.1. D) Comparison of C-lanes of an Italian patient homozygous for the haplotype 2.1 and normal control reveal a 4 bp insertion (nucleotides 1086–1089). E) A 13 bp deletion (nucleotides 1085–1097) can be observed in C-lanes of a patient carrying haplotype 3.1 compared with a normal control.

FIG. 4

Schematic diagram of the AIRE constructs. The full length protein is 545 amino acids. Gray boxes indicate the PHD zinc finger domains, the hatched box the nuclear localization signal. The AIME-ΔSacI mutant is truncated after 306 amino acids, the AIRE-ΔBamHI mutant after 209 amino acids.

FIG. 5

Western blot analysis of cell extracts from transiently transfected COS1 cells. Cells were transfected with the indicated plasmids. The blot was probed with sp97181 antiserum. Expression of the full length protein (lanes 3 and 4) is compared with Mock (lane 1) or pSG5-only transfected cells (lane 2). Expression of the mutant proteins is shown in lane 5 (AIRE-ΔSacI) and lane 6 (AIRE-ΔBamHI). Arrows indicate the detected proteins for AIRE, AIRE-ΔSacI and AIRE-ΔBamHI constructs.

FIG. 6

Subcellular distribution of the AIRE protein. COS1 cells were transfected with 5 µg pSG5-AIRE and stained for AIRE with antibody sp97181 (red) after 24 h. Nuclei were stained with YOYO-1 (green). Images were scanned using a confocal laser microscope scanner. (I) Nuclear localization; Nu: Nucleoli. (II) Cytoplasmic and nuclear localization of AIRE. (a) Red and green images merged; overlapping signals appear yellow. (b) Red image. (c) Green image.

FIG. 7

Co-localization of cytoplasmic AIRE with vimentin. COS7 cells (I and II) or human primary fibroblasts (III) were transfected with pSG5-AIRE and co-stained for AIRE (sp97181, red) and vimentin (green) after 24 h (I and II) or 48 h (III). Images were analyzed with an epifluorescence microscope. (a) Red and green images merged; co-localization of AIRE with vimentin appears yellow. (b) Red image. (c) Green image.

FIG. 8

AIRE-ΔSacI forms nuclear inclusions and co-localizes with vimentin in COS7 cells. COS7 cells were transfected with pSG5-AIRE-ΔSacI and co-stained for AIRE (sp97181, red) and vimentin (green) after 24 h (I) or 48 h (II and III). Nuclei were stained with DAPI (blue, I and III). (a) Red, green and blue images merged. Co-localization of AIRE-ΔSacI and vimentin appears yellow. (b) Red image. (c) Green image. White arrowheads indicate nuclear AIRE-DSacI.

FIG. 9

Subcellular localization of AIRE-ΔSacI and co-localization with vimentin in human primary fibroblasts. Fibroblasts were transfected with pSG5-AIRE-ΔSacI and co-stained for AIRE (sp97181, red) and vimentin (green) after 48 h. (I) Nuclear localization of AIRE-ΔSacI, (II) cytoplasmic co-localization of AIRE-ΔSacI with vimentin. (a) Red and green images merged; co-localization of AIRE with vimentin appears yellow. (b) Red image. (c) Green image. White arrowheads indicate nuclear AIRE-DSacI.

FIG. 10

AIRE-ΔBamHI forms cytoplasmic aggregates and nuclear inclusions in COS7 cells. COS7 cells were transfected with pSG5-AIRE-ΔBamHI and stained for AIRE (sp97181, red) after 24 h (II) or 48 h (I and III) and vimentin (green, II and III). Nuclei were stained with DAPI (blue, I and II). (a) Images merged; co-localization of AIRE with vimentin appears yellow. (b) Red image. (c) Green image. White arrowheads indicate nuclear AIRE-ΔBamHI.

FIG. 11

Subcellular localization of AIRE-ΔBamHI and co-localization with vimentin in human primary fibroblasts. Fibroblasts were transfected with pSG5-AIRE-ΔBamHI and co-stained for AIRE (sp97181, red) and vimentin (green) after 48 h. Nuclei were stained with DAPI (blue). (I) Cytoplasmic aggregates and nuclear AIRE-ΔBanHI. (II) Cytoplasmic filamentous localization of AIRE-ΔBamHI. (a) Images merged; co-localization of AIRE with vimentin appears yellow. (b) Red image. (c) Green image. White arrowheads indicate nuclear AIRE-ΔBamHI.

FIG. 12

Genomic structure of the mouse and human AIRE gene showing the positions of the fourteen exons, the position of the TATA box and a conserved region 3 kb upstream of the first exon. CpG islands and repetitive elements are depicted as solid boxes and arrows, respectively (B 1, B1-F, PB1D9=Alu-like repeats in mouse; B2, B4, MIR=various short interspersed nucleotide elements; L1, L2=various long interspersed nucleotide elements; LTR=long terminal repeats; MER=DNA transposon elements). The human AIRE gene locus (cosmid Q22G11) was previously sequenced.

FIG. 13

Dot-matrix of sequence comparison of the human (SEQ ID NO:4) and murine (SEQ ID NO.:3) AIRE gene structure (A). Arrows mark exons. Arrowhead denotes conserved region (SEQ ID NO:5) shown in detail in FIG. 13B.

FIG. 14 cDNA sequence of murine AIRE (SEQ ID NO:6) gene and deduced amino acid sequence (SEQ ID NO:7).

FIG. 15

The murine AIRE gene is located on chromosome 10. PCR amplification of monochromosomal mouse hybrids, using mouse specific primers Mforw2 Mrev32 (see Example 16). M is 100 bp ladder marker; 1: hybrid containing mouse chr. 10; 2: hybrid containing mouse chr. 3; 3: hybrid containing mouse chr. 3+17, 4: total mouse genomic DNA; 5: total human genomic DNA; 6: water negative control.

FIG. 16

Amino acid sequence comparison of the human (SEQ ID NO:8) and murine (SEQ ID NO:9) AIRE protein. Consensus sequence is indicated (SEQ ID NO:10) Shaded boxes mark PHD fingers and the dolled line the SAND domain. The unclear localization signal (NLS) is underlined, and the LXXLL-motif is boxed.

FIG. 17

Differential splicing of the mouse AIRE gene. Amino acid sequence (SEQ ID NO:12) is indicated above the nucleic acid sequence (SEQ ID NO:11).
(a) Shows skipping of exon 10 (SEQ ID NO:11–12);
(b) Shows deletion of a lysine in exon 8 (SEQ ID NO:13–14);
Shows deletion of Proline, Isoleucine, Threonine, Valine in exon 6(SEQ ID NO:15–16).

FIG. 18

Expression of human AIRE in a series of immunological tissues. Reverse transciption-polymerase chain reaction amplification was performed as described in Example 15. Lanes 1 to 8 correspond to: fetal liver, lymph node, peripheral blood leukocyte, thymus, bone marrow and spleen respectively. Lane 9 is negative control; M1 is lambda HindIII marker, M2 is 100 bp ladder marker.

The examples illustrate the invention

EXAMPLE 1

Isolation of the Human APGD1-cDNA

We have mapped APECED to chromosome 21q22.3 by linkage analysis and further refined the localisation by linkage disequilibrium to a region between the markers D21S25 and D21S171 (Aaltonen, J., et al., Nature Genet 8, 83–87 (1994); Aaltonen et al., Genome Research 7 (1997), 820–827). This critical region was 350 kb in size and a bacterial clone contig was constructed across this region. Several techniques were used to identify candidate genes in this gene rich region. Exon trapping (Buckler, A., et al., Proc. Natl. Acad. Sci., USA, 88, 4005–4009, (1991)) and cDNA selection (Lovett, M., et al., Proc. Natl. Acad Sci, USA, 88, 9628–9632, (1991)) methods identified a new gene, 694N10 (Accession No. Z93322), just distal to the previously knowvn PFKL gene (Phosphofructokinase of liver type, EC 2.7.1.11) (Elson et al., Genomics, 7, 47–56 (1990)) (FIG. 1A). Partial unordered genomic sequence encompassing the PFKL gene (available at the International Chromosome 21 genomic sequence repository, on the worldwide web at eri.uchsc.edu was used to generate a new polymorphic marker, PB1. This marker showed an obligatory recombination in one APECED family, thus we were able to restrict the APECED region to 145 kb between the markers D21S25 and P1 (FIG. 1A). Therefore 694N 10 was excluded as causative gene for APECED.

Figure 2B:
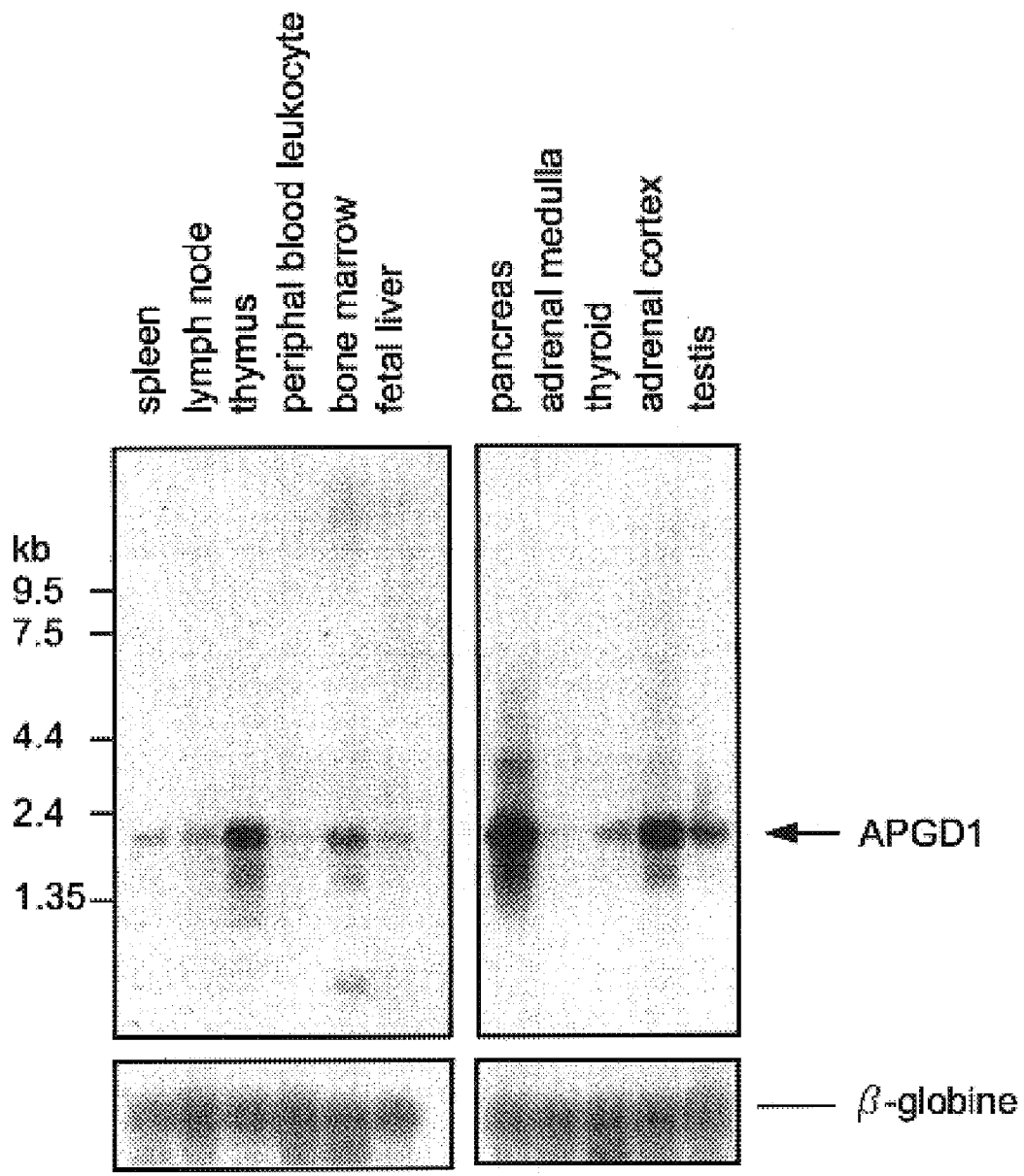

In parallel, we initiated a large scale sequencing approach from cosmid clones 21D1 and 22G11 mapping to the critical region (FIG. 1A). A total of 87 kb of genomic sequence obtained from these cosmids were analysed with BlastN and BlastX algorithms (Altschul, S. F., et al., J. Mol. Biol., 215, 403–410, (1990)) against public databases. Three different EST (Expressed Sequence Tag) clusters were found in a region between D21S25 and PFKL (FIG. 1A). Exon prediction was performed using the GRAIL2 program (Uberbacher, E., et al., Proc. Natl. Acad. Sci, USA, 88, 11261–11265 (1991)). A gene model was predicted directly upstream of the promotor of PFKL where no EST matches were identified (exons G1 to G7, FIG. 1B). However, since the linkage disequilibrium data (Björses, P., et al., Am. J. Hum. Genet., 59, 8779–886 (1996)) suggested the APECED gene to be located in the close vicinity of PFKL further analyses were focused on this potential gene. Polymerase Chain Reaction (PCR) amplification (5'-AGA AGT GCA TCC AGG TTG GC-3' (SEQ ID NO. 17) and 5'-GGA AGA GGG GCG TCA GCA AT-3')(SEQ ID NO:18) of a 316 bp genomic fragment spanning predicted exons G5 and G6 (FIG. 1B) generated a probe for screening a human adult thymus cDNA library (Clontech catalog #HL5010b). Two cDNA clones (B1-1 and D1-1) and a 3' UTR extension PCR product yielded a composite cDNA sequence of 2,245 kb (FIG. 2A). The cDNA clone B1-1 was localised on the physical map by fiber FISH (Fluorescent In Situ Hybridization) (FIG. 1C) (Heiskanen, M., et al., TIG, 10, 379–382 (1996)). Northern blot analysis showed a major transcript of approximately 2 kb expressed in all tissues analysed, the most intensive signals were obtained from thymus, pancreas and adrenal cortex (FIG. 2B). In this respect, it is surprising that no ESTs were found in the databases. The cDNA sequence exhibits an unusually high GC content of 68.8% and contains an open reading frame (ORF) of 581 amino acids followed by a STOP codon at nucleotide 1756. The likely initiator ATG codon occurs at nucleotide 121 (FIG. 2A), predicting a 545 residue protein.

EXAMPLE 2

Structure of the APGD1-gene

The structure of the APGD1 gene was determined from a comparison of the cDNA sequence with the cosmid 22G11 genomic sequence using the est_genome program (developed by Richard Mott, available at the Sanger center, UK). The genomic structure consists of 14 exons spanning 11,9 kb of genomic DNA (FIG. 1B). A putative promotor containing a TATA box located 35 nucleotides from the first nucleotide of exon 1 and a GC box was identified immediately upstream of the first exon of the APGD1 gene. A CpG island was also associated with the promotor region. Detailed analysis of the genomic sequence upstream of the APGD1 gene did not suggest any additional exons within 22 kb of the predicted promotor. The translation of the genomic sequence identified an in frame STOP codon 16 residues upstream of the first amino acid of the translated cDNA sequence. Analysis of the 3' end of the gene suggested that exon 14 represents the last since the STOP codon at position 1756 is followed by repetitive sequences. Further, exon 14 overlaps with the promoter region of the PFKL gene (Levanon, D., et al., *Biochem and Mol. Biol. Int.*, 35, 929–936 (1995)) which is transcribed from the same DNA strand (FIGS. 1B and 2A). Apparent C to T silent polymorphisms were found at third codon positions in exons 5, 6, 10 and 14 (FIG. 2A). The gene organisation was poorly predicted by GRAIL: only three (exons 2, 4 and 6) of the 14 exons were identified bona fide and 7 exons were completely missed FIG. 1B). Yet, the gene is located in a GC rich region and intron-exon boundaries follow the GT-AG rule (Mount, S. M., et al., *Nucleic Acids Research.*, 10, 459–472 (1982)). Subsequent analysis of the genomic sequence with other gene finding software including GRAIL1a (Uberbacher, E., et al., *Proc. Natl. Acad. Sci, USA*, 88, 11261–11265 (1991)), Xpound (Thomas, A., & Skolnick, M. H., *IMA J. Math. Appl. Med. Biol.*, 11, 149–160 (1994)), and Genie (Kulp, D., et al., ISMB-96, St. Louis, Mo., AAAI/MIT Press. available on the worldwide web at hgc.lbl.gov/projects/genie.html) (1996)) showed that Genie, based on hidden Markov model, performed best for modeling the 3' end of this gene (FIG. 1B).

EXAMPLE 3

APECED-associated Mutations Found in the APGD1-gene

Figure 3:
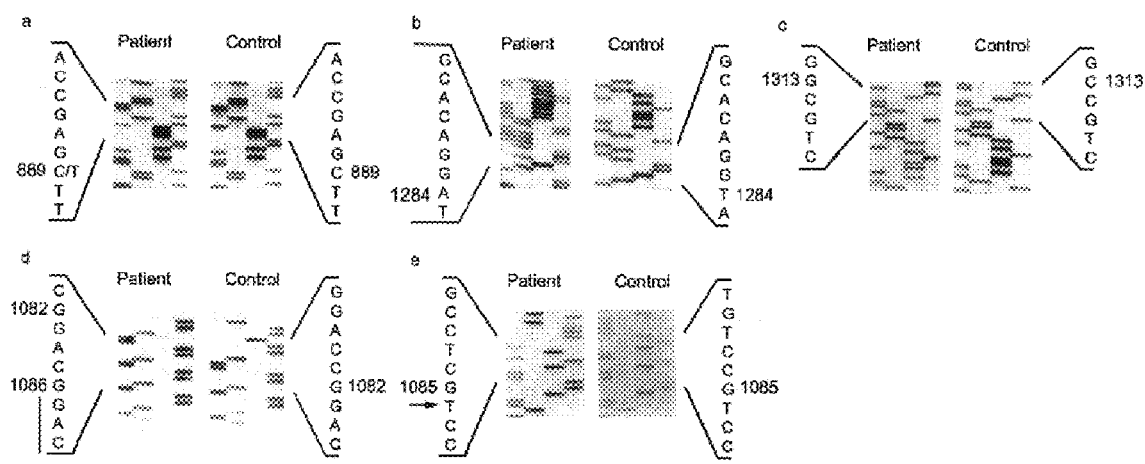

For mutation screening in APECED patients, all 14 exons were amplified from genomic DNA using primers located in the respective flanking introns (primer sequences and the detailed protocols available on the worldwide web at chr21.rz-berlin.mpg.de/APECED.html). Five different mutations were identified in the coding region of APGD1 (Table 1). The mutations were monitored in a control panel of 500 unrelated Finns and 60 unrelated Europeans including 32 CEPH parents. The most common mutation was the "Finnish major mutation" found in 82% of the Finnish patients, all of which have the major disease haplotype (No. 1.1 in Table 1) (Björses, P., et al., *Am. J. Hum. Genet.*, 59, 8779–886 (1996)). This mutation is a C to T transition at nucleotide 889 in exon 6, changing an Arg into a STOP codon. Among the 500 Finns this mutation was detected in two heterozygotes, indicating a carrier frequency of 1:250. The same mutation was also found in an Italian and in a German patient, who carried different haplotypes (haplotypes No. 1.2 to 1.4 in Table 1, respectively). Two mutations were found in exon 8. The first one is a duplication of four nucleotides (CCTG) normally found at position 1086 to 1089. The other mutation in this exon is a 13 bp deletion (nucleotides 1085 to 1097) observed in four non-Finnish patients (two British, a Dutch and a German) carrying the same haplotype (No. 2.1 in Table 1). Two other mutations which involve insertion or deletion of a single nucleotide were found in exon 10. The insertion of an A at position 1284 was found in two compound heterozygote Finnish patients having the Finnish major mutation in the other allele. Deletion of a C was found at position 1313 in a French patient homozygous for the disease haplotype (No. 5.1 in Table 1). Mutations and the associated haplotypes are summarized in FIG. 3 and Table 1. Northern blot analysis performed on lymphoblast mRNA from patients whose cell lines were available (all Finnish patients) did not show a size difference of the transcript or altered level of expression when compared to control subjects. All the mutations cosegregated with the disease in the respective families and were predicted to result in truncation of the conceptual protein (Table 1). This provides strong evidence that alterations of the APGD1 gene represent the primary cause for the APECED disease.

EXAMPLE 4

Recombinant AIRE Expression in *E. coli* and Purification of the Protein

The QIA expressionist method (Qiagen) was used for bacterial expression and purification of the 6×His-tagged recombinant AIRE protein. A 1.8 kb SalI/NotI cDNA fragment derived from clone B1-1pA ( ) and containing the complete AIRE coding sequence was cloned into the pQE32N vector (pQE32N-AIRE). The correct cloning orientation and the reading frame were verified by sequencing. *E. coli* strain SCS1 pSE III was transformed with pQE32N-AIRE and protein expression was induced for 4 h with 1 mM isopropyl-b-thiogalactopyranoside (IPTG). The His-tagged protein was purified under denaturing conditions on a Ni-NTA Agarose column according to the manufacturer's recommendations (Qiagen), and analyzed by SDS-PAGE and Western Blotting.

EXAMPLE 5

AIRE Expression Plasmids for Transient Transfection

For expression of the full length 545 amino acids protein in mammalian cells the 1.8 kb EcoRI insert from B1-1pA AIRE cDNA was cloned into the expression vector pSG5 (Invitrogen) and named pSG5-AIRE. The correct orientation was verified by restriction digest and sequencing. AIRE deletion mutants were generated by restriction digests using unique restriction sites in the cDNA. The pSG5-AIRE-ΔBamHI construct was generated by deleting a 1.1 kb BamHI 3'-termninal fragment from pSG5-AIRE cDNA, producing a protein that is truncated at residue 209. In this construct, a stop codon is provided by the pSG5 vector sequence after encoding for 17 nonsense amino acids at the AIRE-ΔBamHI C-terminus. The pSG5-AIRE-ΔSacI construct was generated by deleting a 0.8 kb SacI/BgIII fragment from pSG5-AIRE cDNA and religation of the DNA molecule after generating blunt ends by T4 DNA polymerase and Klenow Fragment. This construct encodes for a protein truncated at amino acid 306; a stop codon is provided by the vector sequence after encoding for 2 nonsense amino acids at the C-terminus of AIRE-ΔSacI.

EXAMPLE 6

Antibody Production and Purification

Polyclonal antibodies against the AIRE protein were obtained by injecting rabbits with the synthetic peptides MATDAALRRLLRLHR (SEQ ID NO:19) (corresponding to aa 1–15) and SQPRKGRKPPAVPK (SEQ ID NO:20) (corresponding to aa 107–120), respectively. The resulting immune sera sp97179 (for aa 1–15) and sp97181 (for aa 107–120) were affinity purified against their corresponding synthetic peptides immobilized on a HiTrap NHS-activated 1 ml column (Pharmacia) according to the manufacturer's recommendations.

EXAMPLE 7

Cell Culture and Transfection Experiments

COS 1 cells were maintained at 37° C. and 5% $CO_2$ in Dulbecco's Modified Eagle Medium (DMEM) containing 1000 mg/l glucose, 10% Fetal Calf Serum, 10 U/ml Penicillin and 10 µg/ml Streptomycin. Transfections were performed by electroporation as follows: $10^6$ cells grown at 80–90% confluence were centrifuged, washed twice in ice-cold phosphate buffered saline (PBS) containing 2 mM Hepes (HeBS) and resuspended in 800 µl HeBS. DNA was diluted in 130 µl HeBS before being added to the cells (either 2, 5, 10 or 20 µg of DNA). After 10 min incubation on ice, cells were pulsed with a field strength of 3 kV/cm (capacitance 25 µf) using a Gene Pulser (Bio-Rad). Cells were allowed to recover on ice for 10 min before being transferred in 10 ml pre-equilibrated DMEM containing 25 mM Hepes. Transfected cells were seeded in Leighton tubes (Costar) for immunofluorescence studies ($1.5 \times 10^5$ cells/Leighton) and in 10 cm petri dishes ($4 \times 10^5$ cells/dish) for cell extract preparations and incubated at 37° C. and 5% $CO_2$ for 24 h or 48 h. COS7 cells and fibroblasts were maintained at 37° C. and 5% $CO_2$ in DMEM/F12 medium containing 1000 mg/l glucose, 10 % Fetal Calf Serum, 10 U/ml Penicillin and 10 µg/ml Streptomycin. Cells were transfected using the LipofectACE method according to the manufacturer's recommendations (Gibco Life Technologies). Cells were seeded into a six-well-plate containing glass cover slips ($4 \times 10^5$ cells per well) and allowed to grow for 24 h before transfection. Transfections were performed using 3 µg of DNA per well and cells were incubated in the LipofectACE/DNA mix for 6 h. Cells were analyzed by indirect immunofluorescence 48 h post-transfection.

EXAMPLE 8

Indirect Immunofluorescence

Cells were fixed either with methanol/acetone or paraformaldehyde (PFA). Methanol/acetone fixation: Cells were briefly rinsed in PBS, fixed in–1:1 methanol/acetone for 10 min at −20° C., air dried and then incubated at 4° C. overnight in PBS containing 3% Bovine Serum Albumin (BSA). After a brief rinse in PBS, cells were incubated with antisera sp97179 or sp97181 diluted 1:200 in PBS/0.1% Triton X-100 (PBS-T) for 1 h at room temperature. Cells were washed three times in PBS-T for 10 min followed by 1 h incubation with a Cy3 labeled anti-rabbit antibody (Jackson Immuno Research) diluted 1:200 in PBS. Cells were washed twice in PBS-T and once in PBS for 10 min before staining with 12 nM YOYO-1 iodide in PBS (Molecular Probes) for 15 min. After washing in PBS three times for 5 min, preparations were mounted in 75% glycerol/PBS.

PFA-fixation: Cells were briefly rinsed in PBS before fixation in 3.7% PFA in PBS for 10 min at room temperature. Cells were again briefly rinsed and then permeabilized with PBS/0.2% Triton X-100 for 10 min. Blocking and incubation with the AIRE antibodies were performed as described above, except that blocking was reduced to 1 h at room temperature. Simultaneous detection of AIRE and vimentin was performed by co-staining cells with sp97179 (or sp97181) and anti-vimentin-antibodies. Vimentin polyclonal antibody raised in goat (produced by standard techniques well known to the person skilled in the art) was diluted 1:400 and incubated for 1 h, followed by incubation with a FITC-conjugated donkey-anti-goat secondary antibody (Jackson Immuno Research) diluted 1:200 in PBS. Coverslips were mounted in Vectashield (Vector Laboratories) containing 5 µg/ml DAPI.

Cells were either visualized and scanned with a confocal laser microscope (LSM 510-axioplan2, Zeiss) or analyzed with an epifluorescence microscope (Axioskop 50, Zeiss). Photos were taken with a CCD camera.

EXAMPLE 9

Western Blot Analysis

Harvested cells were lysed in a buffer containing: 2% Triton X-100, 1% SDS, 100 mM NaCl, 10 mM Tris pH 8, 1 mM EDTA and supplemented with 2 mM PMSF, 10 mM b-mercaptoethanol, 10 µg/ml Leupeptin and 10 µg/ml Pepstatin. 20 µg of total protein extracts were separated by 12% SDS-PAGE and blotted on a PVDF membrane. The membrane was blocked for 2 h in TBS-T (20 mM Tris pH 7.5, 150 mM NaCl, 0.05% Tween-20) containing 3% BSA followed by incubation with the polyclonal antiserum (sp97179, sp97181) diluted 1:1000 in TBS-T for 1 h. After washing the membrane three times for 5 min in TBS-T, the membrane was incubated for 1 h with an anti-rabbit IgG alkaline phosphatase conjugate (Calbiochem) diluted 1:5000 in PBS-T. The membrane was then washed three times for 5 min in TBS-T, briefly rinsed twice in TBS and incubated in Western Blue Stabilized Substrate (Promega) for 6 min. The reaction was stopped by rinsing the membrane with $H_2O$.

In order to demonstrate the specificity of the antibodies in immunofluorescence and Western blot detection, experiments were repeated after pre-incubation of the antisera with an excess of His-tagged AIRE recombinant protein in PBS-T for 1 h at room temperature.

EXAMPLE 10

Transient Expression of AIRE and Characterization of Polyclonal Antibodies

Figure 4:
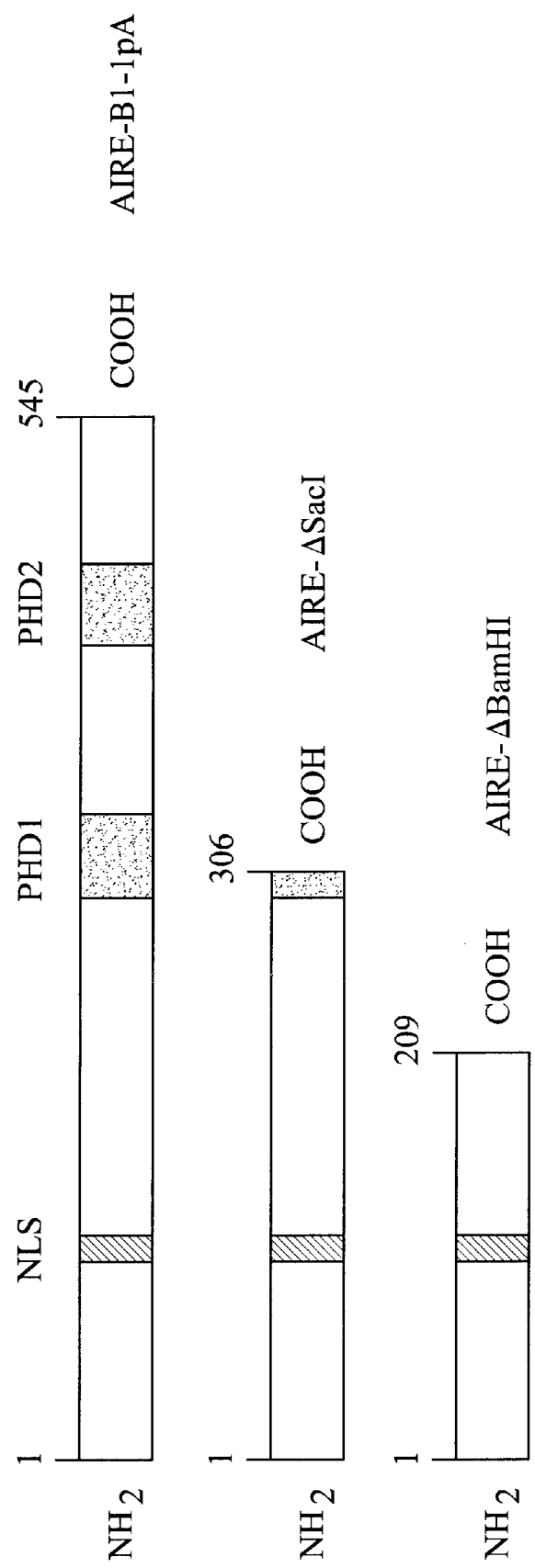

In order to investigate the cellular sub-localization of wild-type and deletion mutants of the AIRE protein in mammalian cells, the constructs shown in FIG. 4 were designed. The full-length construct contains a cDNA encoding for the 545 residues AIRE protein (AIRE-B1-1pA). Two AIRE mutants truncated at amino acid residues no. 306 and no. 209 were designated AIRE-Δ SacI and AIRE-ΔBamHI, respectively. AIRE-ΔSacI is truncated within PHD1, whereas AIRE-ΔBamHI is lacking a larger protein segment encompassing both PHD domains. Full-length or truncated AIRE were expressed-transiently in monkey COS cells and human primary fibroblasts using an SV40 promoter. For immunodetection of the AIRE protein, two polyclonal antisera were raised against synthetic peptides corresponding to the $NH_2$-terminal region and to the nuclear targeting signal (sp97179 and sp97181; see Example 6). Affinity-purified antibodies were tested on Western blots containing the 6×His-tagged recombinant AIRE fusion protein expressed in

Figure 5:
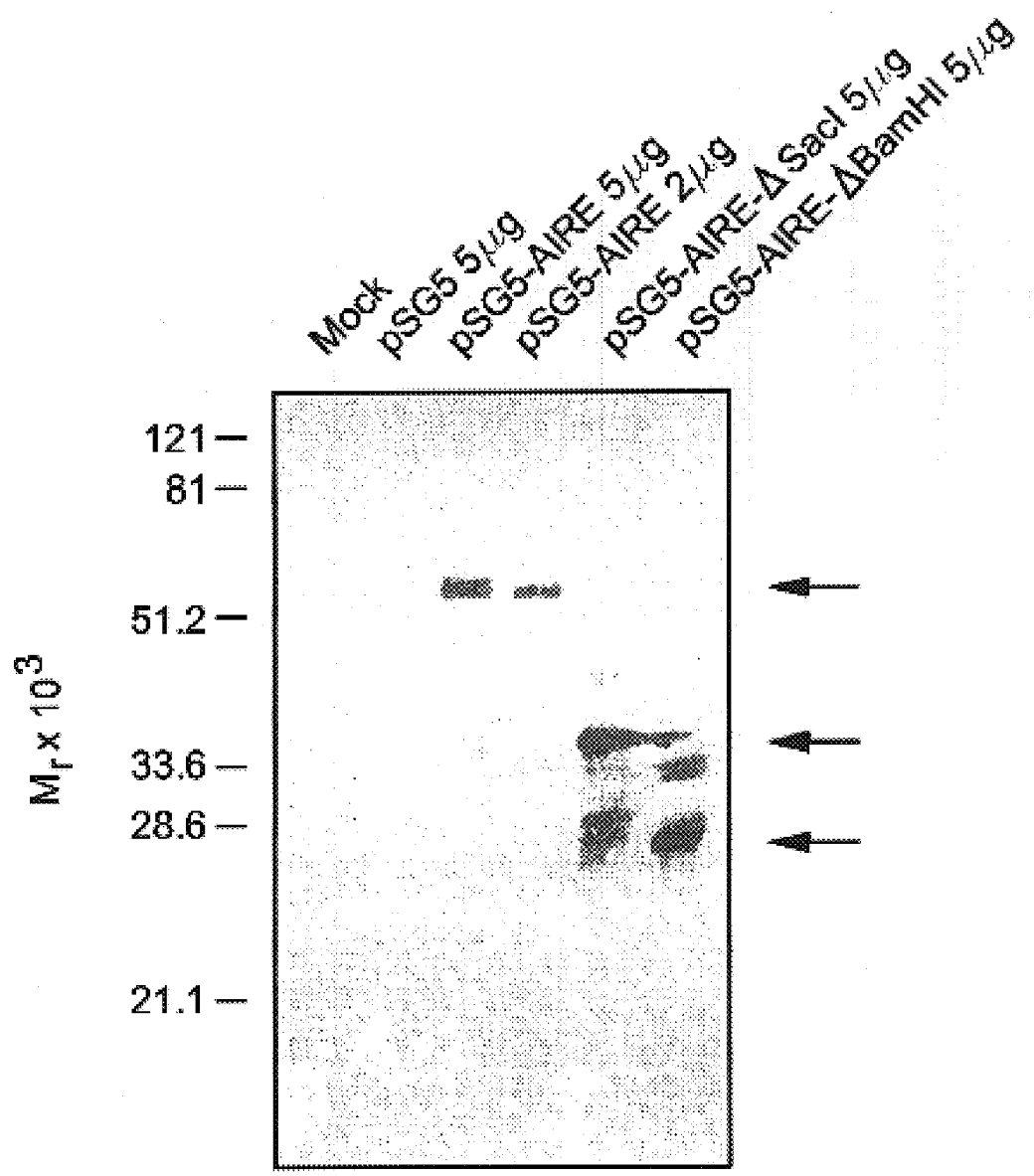

*Escherichia coli.* Both sp97179 and sp97181 antisera selectively recognized the His-tagged full length AIRE. FIG. 5 shows a Western blot analysis of the expression of the AIRE constructs in transfected COS1 cells using antibody sp97181. The immunoblot revealed one strong immunoreactive band corresponding to the gene product of each construct. The size of the full length AIRE protein expressed in transfected cells was calculated at 58.8 kDa that is in agreement with the predicted molecular weight of 57.7 kDa. When cells were transfected with the truncated constructs AIRE-ΔSacI and AIRE-ΔBamHI, appropriate size bands were seen at 34.7 kDa and 23.5 kDa, respectively. No immunoreactivity was found in mock transfection nor in cells transfected with empty pSG5 vector. Similar results were obtained with sp97179 antiserum.

Immunocytofluorescence detection of the AIRE constructs expressed in COS cells was investigated 24 h and 48 h post-transfection by confocal laser microscopy and serial optical sections, after staining with antibodies sp97179 and sp97181. The staining pattern obtained with sp97181 antiserum was essentially similar to that of sp97179. Only transfected cells showed a labeling with either of these antibodies indicating that COS1 cells are not expressing detectable endogenous AIRE. Mock or pSG5-only transfected cells showed no evident staining with either antisera. Immunofluorescence labeling as well as Western blot specific detection were blocked by pre-incubation of the antibodies with AIRE recombinant protein, further confirming the specificity of the antibodies. All experiments were performed in parallel with both antibodies and we will describe here data obtained using sp97181 antibody.

EXAMPLE 11

Sub-cellular Localization of Wild-Type AIRE

Figure 6:
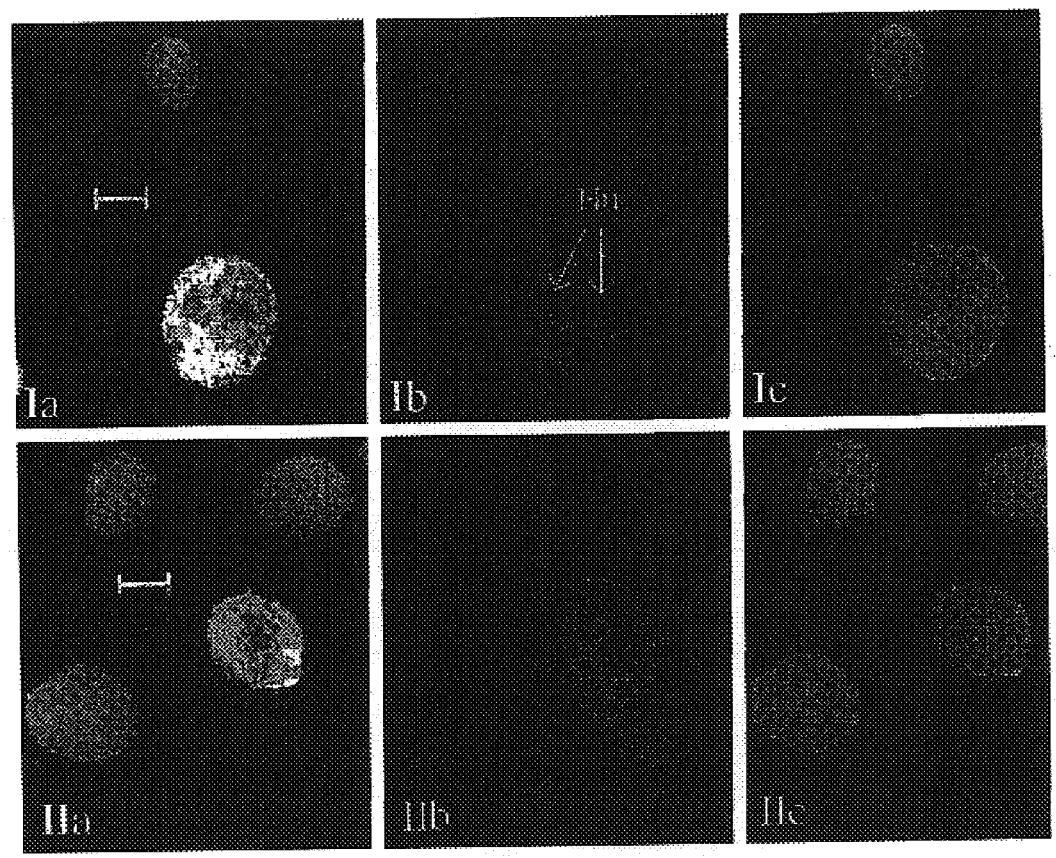

COS1 cells transfected with the full length construct showed two populations of stained cells, one with a punctuate granular staining strictly restricted to the nucleus, as defined by YOYO-1 labeling of DNA, and a second one showing also a cytoplasmic expression of AIRE (FIG. 6). Transfection experiments carried out with either 2, 5, 10 or 20 μg of AIRE B1-1pA cDNA led to similar observations. When more than 300 transfected cells were analyzed, cytoplasmic staining was observed in approximately 70% of the cells whereas the AIRE expression was confined to the nucleus in the remaining 30%. In all of the cells where the staining was exclusively nuclear, the antibody reacted with punctuate structures. AIRE localized into small distinct speckles uniformly distributed in a given optical section of the nucleoplasm but excluded from the nucleoli (FIG. 6-I). Serial optical sections and confocal imaging showed that the nuclear labeling was present in domains representing approximately 5–8 mm of the nucleoplasm depth and thus localized within at least two-thirds of the nuclear volume. In cells where AIRE was expressed in the cytoplasm, the antibody decorated fibers spanning 4–8 mm of the cell depth that were arranged in a scaffold-like structure often forming bundles around the nuclear envelope (FIG. 6-II), reminiscent of the intermediate filaments of the cytoskeleton. This AIRE filamentous staining pattern was generally observed in conjunction with the characteristic nuclear speckles, albeit the nuclear staining sometimes consisted of fibrils spanning the nucleoplasm. Also, a few of the transfected cells were void of detectable labeling in the nucleus. No remarkable difference in the AIRE localization pattern could be noted between cells analyzed 24 h or 48 h after transfection.

Figure 7:
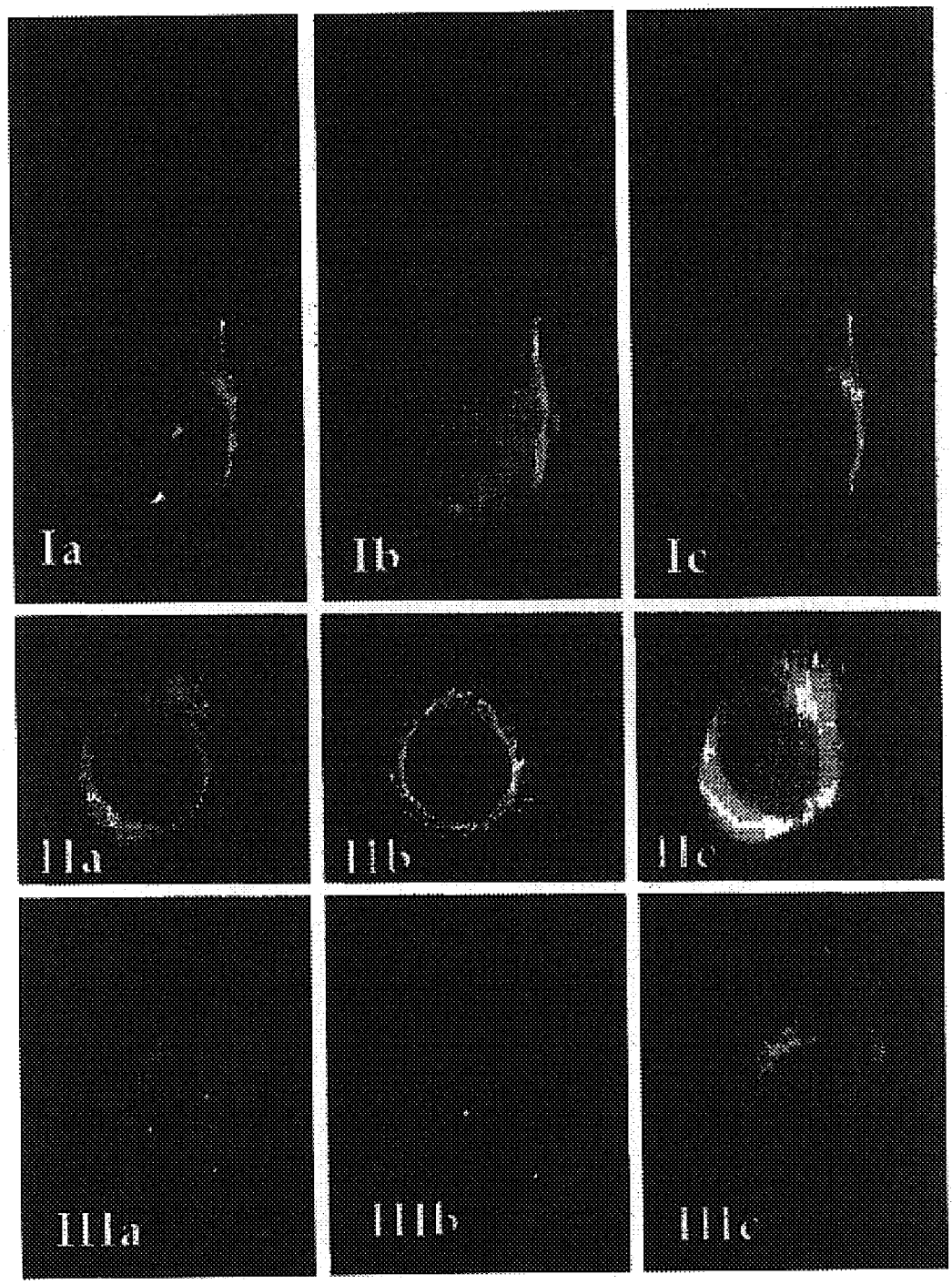

To further authenticate the identity of the cytoskeletal filaments revealed by sp97181, additional transfection experiments were performed with COS1 or COS7 cell lines and human primary fibroblasts. Cells were double-stained with sp97181 and a polyclonal antibody specific for vimentin (produced by standard techniques well known to the person skilled in the art). In COS cells expressing AIRE in the cytoplasm, both antisera decorated similar cytoplasmic fibers stretching from the nuclear envelope to the plasma membrane. FIG. 7-I shows that the AIRE and vimentin patterns are perfectly overlapping, demonstrating co-localization of AIRE with vimentin intermediate filaments. It should yet be noted that AIRE and vimentin appeared only partially overlapping in some of the transfected cells. FIG. 7-II shows the vimentin filaments of a cell expressing AIRE mainly in the nucleus, where the characteristic pattern appears composed of 50–100 speckles. In contrast, no evident punctuate nuclear staining could be observed in the cell shown in FIG. 7-I. Data strongly suggest that AIRE is a nuclear protein localizing to distinct functional sub-domains in the nucleoplasm but which may also be transiently stored in the cytoplasm during particular cellular stages. A similar dual cytoplasmic and nuclear AIRE staining pattern was observed in transfected primary fibroblasts. FIG. 7-III shows here discontinuous cytoplasmic fibers arranged along vimentin intermediate filaments. Endogenous AIRE expression was not clearly detectable in fibroblasts either, and the AIRE sub-cellular localization pattern observed in both cell types was independent of the fixation method (see Example 8).

EXAMPLE 12

Altered Cellular Localization of Truncated AIRE Products

Figure 8:
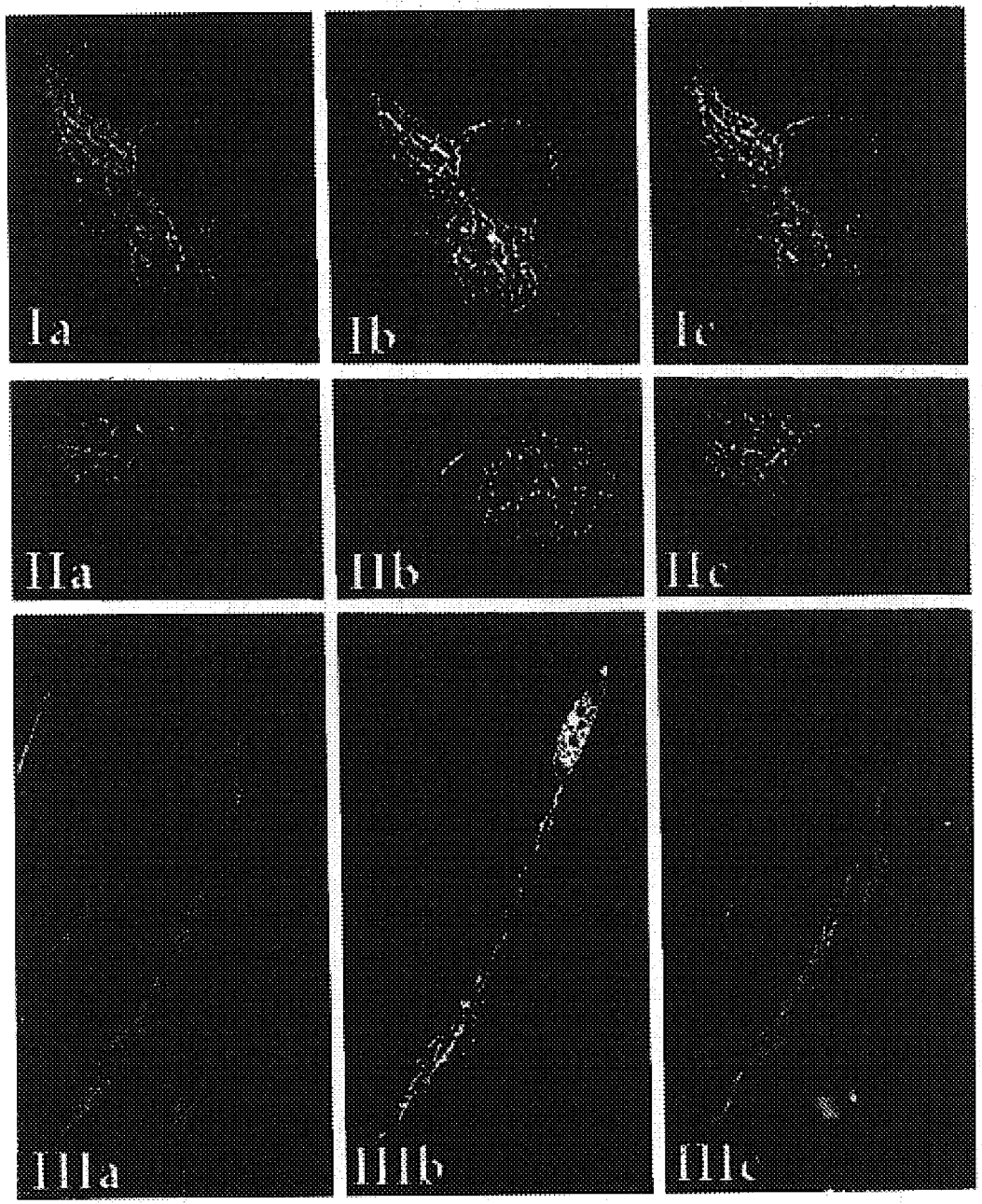
Figure 9:
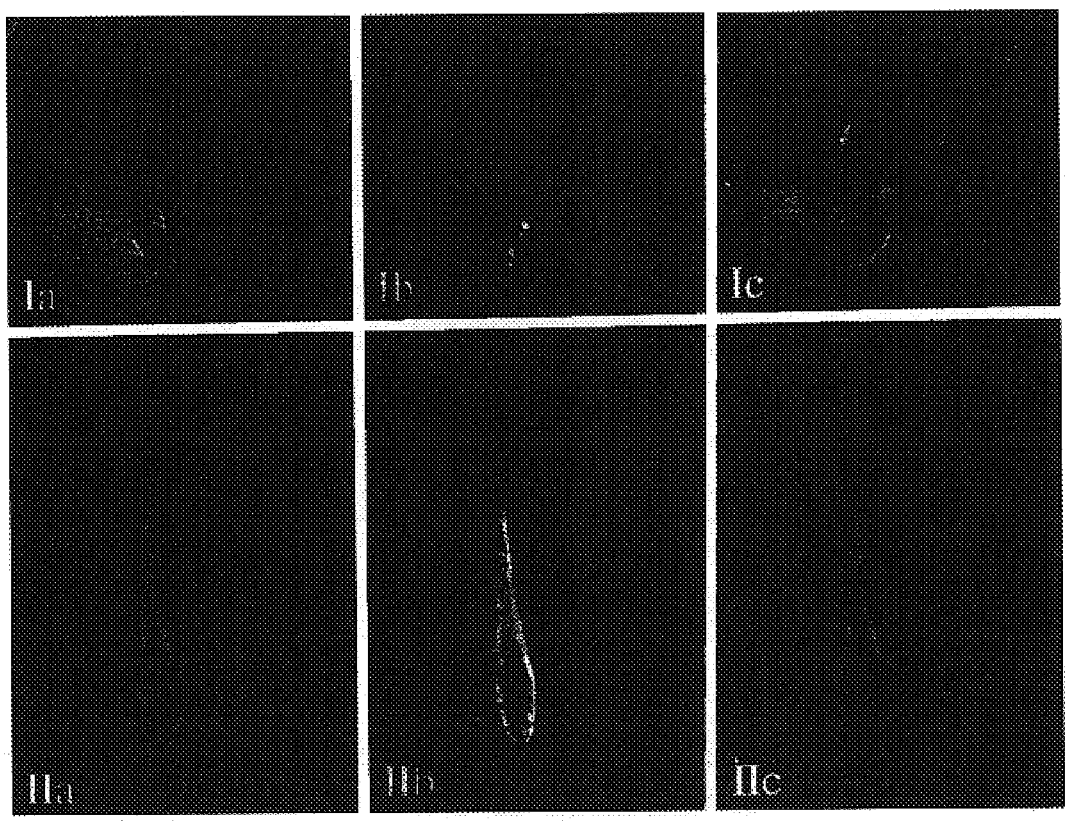

The two N-terminal AIRE protein fragments expressed in COS cells or fibroblasts showed dramatic changes in their cellular distribution as compared with wild-type AIRE. The AIRE-DSacI construct expressing a 35 kDa protein truncated within PHD1 domain was also found localized in both cytoplasmic and nuclear compartments. In COS cells, cytoplasmic AIRE-DSacI showed at least in part co-localization with vimentin (FIG. 8-I) and often revealed fiber bundles around the nuclear envelope which were occasionally associated with small aggregates (FIG. 8-II). In contrast to wild-type, AIRE-ΔSacI protein showed a drastically altered nuclear sub-localization pattern. 24 h post-transfection, the mutant protein systematically localized in discrete nuclear domains consisting of intensely labeled foci, whereas no speckled pattern organization could be distinguished (FIGS. 8-I and III). These intense nuclear dots were heterogeneous in size but often appeared as lipid-like round structures found as pairs but also as 3, 4 or multiple inclusions in the nucleoplasm, sometimes seen in the immediate vicinity of the nucleoli. These observations evoke similar structures referred as nuclear bodies, particularly coiled bodies. In some of the cells analyzed 48 h post-transfection, these nuclear inclusions were set against a very faint staining distributed diffusely in the nucleoplasm and excluding nucleoli. In human fibroblasts, similar observations were noted, though the nuclear inclusions were often significantly larger than in COS cells (FIG. 9-I); the cytoplasmic distribution was also found co-localizing with vimentin (FIG. 9-II).

Figure 10:
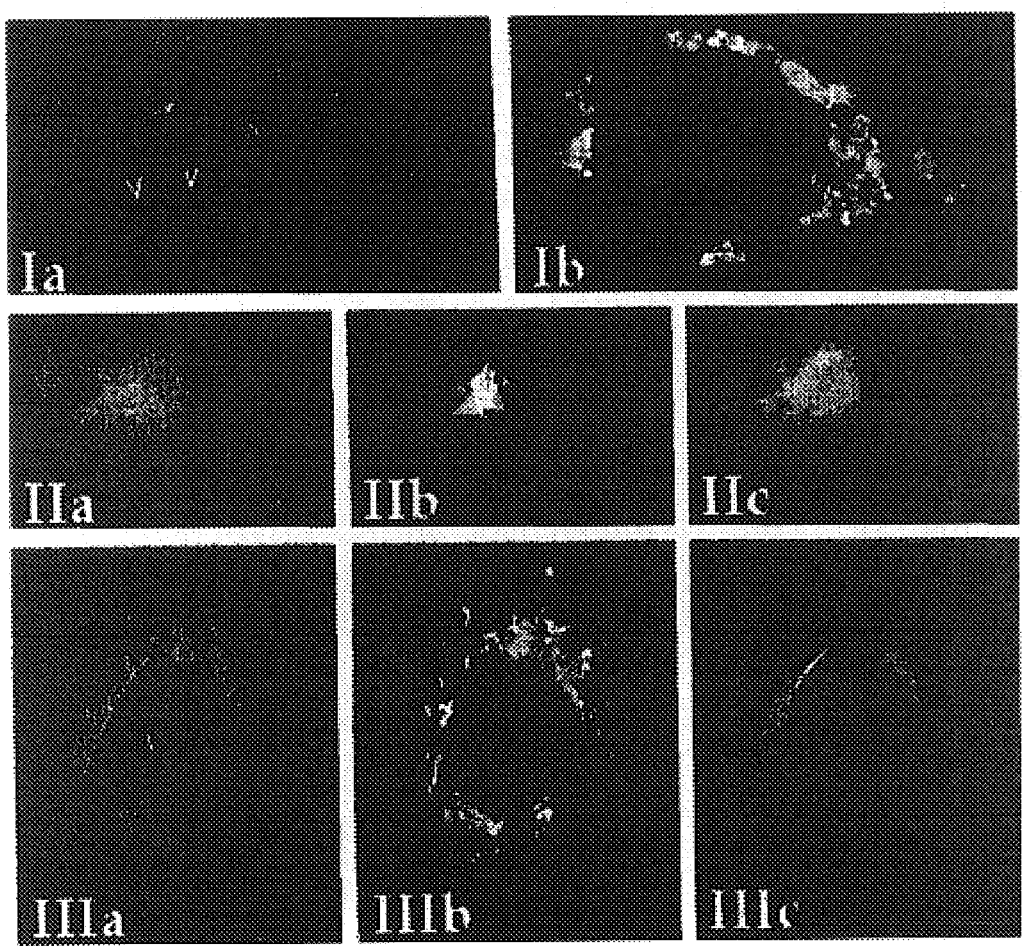
Figure 11:
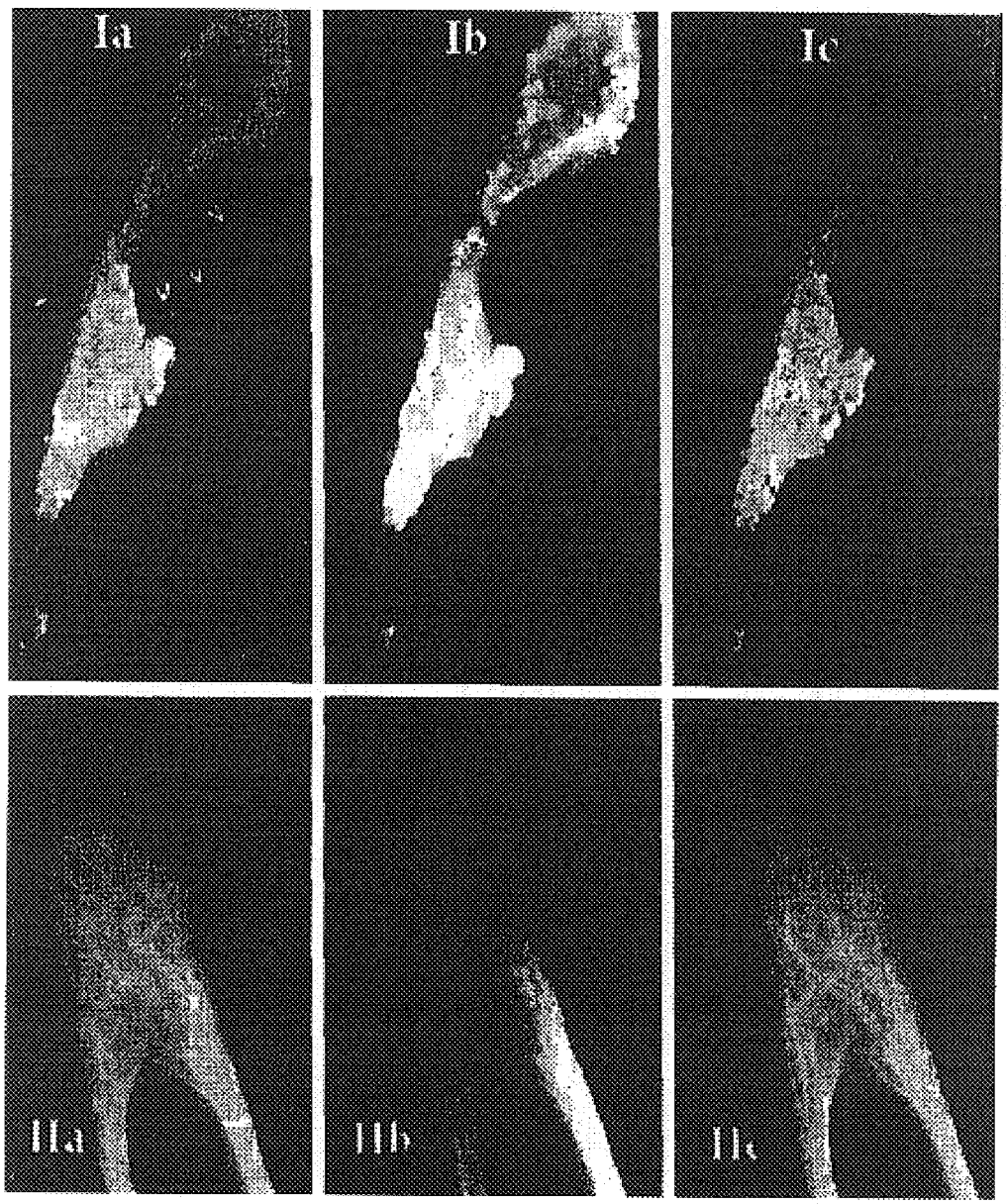

The AIRE-ΔBamHI construct showed a strikingly different sub-cellular localization as compared with full-length AIRE and AIRE-ΔSacI. This truncated protein of 23.5 kDa presented a drastically impaired cytoplasmic distribution pattern where fibers could never be observed in any of the COS cells expressing AIRE-ΔBamHI. Instead, large cytoplasmic aggregates were commonly concentrated in the perinuclear region (FIG. 10-I) or at one pole of the nucleus (FIG. 10-II), albeit sometimes dispersed in the cytoplasm (FIG. 10-III). The same construct expressed in fibroblasts could also form cytoplasmic aggregates (FIG. 11-I), but interestingly the mutant protein has retained the ability to co-localize along vimentin intermediate filaments in this cell type. Nonetheless, AIRE-ΔBamHI and vimentin staining revealed unusual wavy filaments that were never observed otherwise (FIG. 11-II). Besides, COS cells and fibroblasts containing large aggregates of the AIRE-ΔBamHI protein generally presented a dramatically altered distribution of the vimentin intermediate filaments (FIG. 10-III). This is particularly exemplified in the cell shown in FIG. 11-I, where vimentin appears trapped within AIRE aggregates rather than being organized in filaments. This evokes the hypothesis that protein-protein interactions involved in maintaining the shape and integrity of intermediate filaments are impaired in cells overexpressing AIRE-ΔBamHI. The nuclear staining showed a confined pattern comparable to that of the AIRE-ΔSacI truncated protein as indicated in FIG. 10-I. Intensely labeled discrete foci appearing as pairs or as multiple dots with a typical diameter of about 1 micron were observed at 24 h or 48 h post-transfection. Orthogonal sections of such nuclear inclusions indicate rod-like structures spanning 2–5 μm in the nucleoplasm depth. However, no diffuse or speckled nuclear staining could be seen at 24 h nor 48 h post-transfection.

Importantly, these data showed that deletion of the one-third C-terminal part of AIRE containing the PHD motifs abolished the normal nuclear distribution. The question whether the PHD zinc fingers directly mediate the correct protein localization to specific nuclear domains was not addressed here. The truncated proteins retained the ability to be targeted to the nucleus since they contain the NLS domain. However, the two deletion mutants are mislocalized in the nucleus when lacking an element conferring speckled punctuate pattern and located between residue no. 306 and the C-terminus.

EXAMPLE 13

Isolation of the Mouse AIRE Gene

Briefly, mouse homologues of the human AIRE gene were isolated by cross-species hybridization of mouse genomic libraries with a human cDNA probe containing the complete AIRE coding sequence. Six positive mouse clones (PAC RPCIP711H2150, P1's ICRFP703A23152, A10129, G23152 and J2183, and cosmid MPMGc121L12287) were isolated from the screenings and were analyzed further by restriction digest mapping and southern hybridization analysis.

In detail, the mouse homolog of the human AIRE gene was isolated by cross-species screening of various mouse genomic libraries with a human cDNA containing the complete AIRE coding sequence (see FIG. 2A, referred to as hAIRE). Six positive clones were isolated and analyzed by restriction digest: 1 PAC (RPCIP711H2150), 4 P1s (ICRFP703A23152, A10129, G23152 and J2183) and 1 cosmid (MPMGc121L12287). When hybridized with hAIRE, all clones showed 4 EcoRI fragments totaling a size of 20,6 kb excepted for A10129 showing an AIRE EcoRI pattern of 13,54 kb. Hybridizations with the most 5' end or 3' end of hAIRE indicated that A10129 was missing at least the first exon, whereas the 5 other genomic clones contained the complete AIRE coding sequence. Cosmid MPMGc121L12287 was chosen for genomic sequencing. The mouse AIRE exons were mapped by restriction mapping and Southern hybridization of cosmid L12287 with individual human exons. The gene organization was characterized further after examination of the complete genomic sequence and comparison with AIRE mouse cDNA sequence.

EXAMPLE 14

Restriction Digests and Southern Hybridization Analysis

DNA from the mouse hAIRE positive clones were digested with EcoRI and HindIII restriction enzymes (New England Biolabs) according to the manufacturer's recommendations. Digested DNA was separated by 1–1.5% agarose gel electrophoresis and transferred onto Amersham Hybond-N+ nylon membranes. Full-length hAIRE probes and probes corresponding to either the most 5' end or the 3' end of hAIRE were generated by PCR. Southern hybridizations were carried out overnight at 42° C. in hybridization mix consisting of 5×SSPE, 5×Denhardt's solution, 50% Fluka formamide, 1% SDS and 0.05 mg/ml of denatured salmon sperm DNA. Filters were washed in 2 changes of 2×SSC each for 10 minutes at 42° C., then in 2 changes of 2×SSC/0.1% SDS, the first for 15 min at 42° C. and then a final wash for 20 minutes at 65° C. Filters were exposed at −70° C. to Kodak X-OMAT AR imaging film with a single intensifying screen for several hours to overnight, depending on the intensity of signals.

EXAMPLE 15

Human and Mouse RT-PCR Analysis

Human: RT-PCR analysis was performed on Clontech's Human Immune System Multiple Tissue cDNA Panel of first-strand cDNA from the following tissues: human bone marrow, fetal liver, lymph node, peripheral blood leukocyte, spleen, thymus and tonsil. Primers B127FR4-21 (5'-GGC TTC TGA GGC TGC ACC) (SEQ ID NO:28) and B127FR4-29 (5'-GCT CTG GAT GGC CTA CTG C) (SEQ ID NO:21) were used to amplify a 1.6 kb region specific for hAIRE. Each PCR was performed in a 50 ml reaction mix containing 5 ml of MTC Panel cDNA, 10–20 pmol of each primer, 1 ml of a 10 mM dNTP mix, 5 ml of Perkin Elmer GeneAmp "10×–PCR buffer (100 mM Tris-HCl pH 8.3; 500 mM KCl; 15 mM $MgCl_2$; 0.01% w/v gelatin), and 3 ml of freshly prepared 28:1 (7 mM:1.4 mM) mixture of TaqStart Antibody (Clontech) and AmpliTaq" DNA Polymerase (Perkin Elmer). PCR reactions were performed in a Biometra UNO II thermocycler beginning with a 2 min initial denaturation step at 94° C., followed by 38 cycles of 94° C. for 45 sec, 56° C. for 40 sec 72° C. for 1 min, and a final extension step at 72° C. for 5 min. Products of the PCR were re-amplified with nested primers B127FR4-17 (5'-AGA AGT GCA TCC AGG TTG GC) and B127FR4-33 (5'-GTG TGC TCG CTC AGA AGG G) to confirm that the products were specific to hAIRE.

RT-PCR amplification with primers B127FR4-21 and B127FR4-29 was also performed on human marathon tissues isolated from lung, muscle, testis, hindbrain, and spinal cord following the PCR conditions described above.

Mouse: Mouse primers Mforw4 (5'-TGG CAG GTG GGG ATG GAA) (SEQ ID NO:24) and Mrev15 (5'-GGA GGG ATG GAA GGG GAG GA) (SEQ ID NO:25) were used to amplify AIRE specific regions from Clontech's Mouse Multiple Tissue cDNA Panel 1 (consisting of first-strand cDNA from mouse heart, brain, spleen, lung, liver, skeletal, kidney, testis and 7-day, 11-day, 15-day and 17-day embryo tissues). PCR reaction mixtures were set up according to the same conditions described for human RT-PCR's, with the exception of using mouse specific primers and a PCR annealing temperature of 63° C.

EXAMPLE 16

Chromosomal Localization of mAIRE

Chromosomal localization of mAIRE was established by PCR analysis of mouse chromosomes 3, 10 and 17. PCR amplifications were performed using mouse specific primers Mforw2 (5'-TCC CAC CTG AAG ACT AAG C) (SEQ ID NO:26) and Mrev32 (5'-TCA CAG CTC TCT GGA CAG AA) (SEQ ID NO.:27) on cell hybrids SN11CS3 (chromosome 3), SN17C3 (chromosome 10) and EJ167 (chomosomes 17 and 3 on a human background). PCR reactions were performed in 30 ml volumes containing 5 ml of mouse chromosomal preparations, 10–20 pmol of each primer, 1 ml of a 10 mM dNTP mix, 5 ml of Perkin Elmer GetteAmp "10x–PCR buffer, and 3 ml of freshly prepared 28:1 (7 mM:1.4 m) mixture of TaqStart Antibody (Clontech) and AmpliTaq" DNA Polymerase (Perkin Elmer). PCR reactions were performed in a Biometra UNO II thermocycler beginning with a 2 min initial denaturation step at 94° C., followed by 35 cycles of 94° C. for 45 sec, 51 ° C. for 40 sec, 72° C. for 2 min, and a final extension step at 72° C. for 5 min.

EXAMPLE 17

PCR Products

Products from PCR amplifications were purified using the Qiagen QIAquick PCR Purification Kit or Clontech Chroma Spin+TE columns. Purified products were then checked by 1.5% agarose gel electrophoresis and sequenced.

EXAMPLE 18

Genomic Sequencing

The cosmid DNA was isolated using a standard lysis method (Birnboim and Doly 1979) and purified on a CsCl-gradient (Radloff et al. 1967). The closed circle band was sonicated, size fractionated and ligated into M13 vector (Craxton 1993). M13 templates were prepared by the triton method (Mardis 1994). The shotgun sequencing was performed using Thermo Sequenase (Amersham) and dye-terminator chemistry (Perkin Elmer). Data were collected using ABI 377 automated sequencers and assembled with the gap4 (Staden 1996). Gaps were closed by resequencing the M13 templates with ET dye primers (Amersham).

Computer Analysis: Genome-wide repeats were identified with the Repeatmasker program (A. F. A Smit and P. Green on the internet in file transfer protocol (ftp) at genome.washington.edu/RM/RepeatMasker.html). The GC content and distribution was determined with the LPC algorithm (Huang 1994). Homology searches against various databases were performed using BLAST version 1.4 (Altschul et al. 1990) and FASTA version 2.0 (Pearson and Lipman 1998). Programs GRAIL2 (Uberbacher and Mural 1991), XPOUND (Thomas and Skolnick 1994), MZEF (Zhang 1997) and GENSCAN (Burge and Karlin 1997) were used for exon prediction. Promoter predictions were done with "Promoter Scan II" (Prestridge1995) and "Transcription Start Site" using both Ghosh/Prestridce (TSSG) and Wigender (TSSW) motif databases (V. V. Solovyev, A. A. Salamov and C. B. Lawrence on the internet at dot.imgen.bcm.tmc.edu:9331/gene-finder/gf.html).

EXAMPLE 19

Comparative Genomic Sequencing

Cosmid L12287 was completely sequenced (468,872 bp long; EMBL accession no. AF07379) and the data were compared with the human AIRE gene locus that we have previously sequenced (36,284 bp, accession no. HSAJ9610). Automatic sequence analysis of clone L12287 was performed with the Rummage software available on the world-wide web at genome.imb_jena.de). Gene prediction progams detected the AIRE gene and revealed also an incomplete gene model located 6 kb from the 5' end of AIRE that was corroborated by anonymous EST matches (e.g. accession no. AA413561). Interestingly, one of the anonymous exons showed high homology with a trapped exon (HC21EXc32; D86111) mapping to human chromosome 21q22.3 (Genebank Accession no. D86111) This confirmed the high degree of conserved syntheny between mouse and human in this region.

Figure 12:
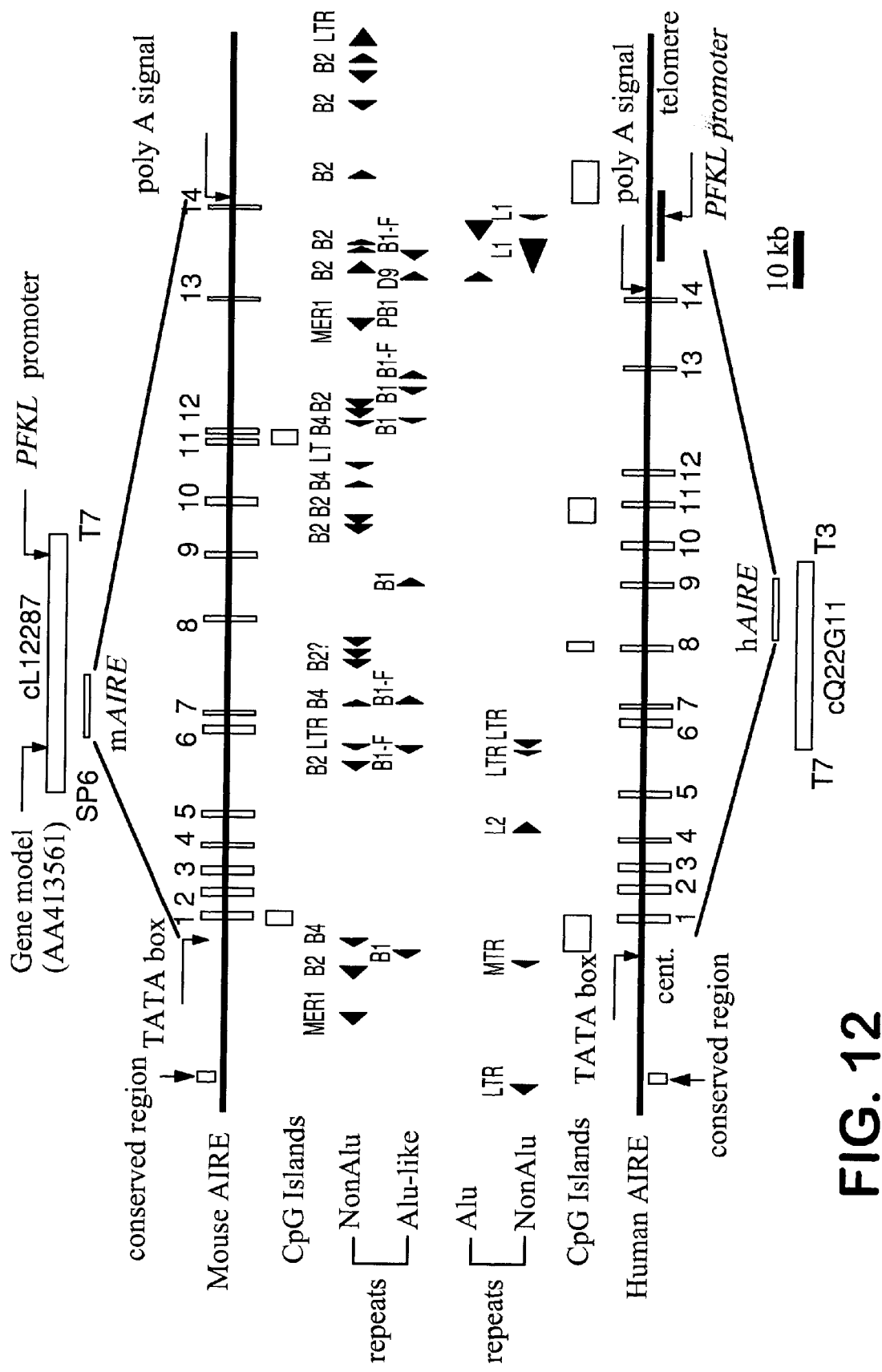

The mouse AIRE gene structure was initially deduced by comparison of the genomic sequence with that of the hAIRE human cDNA. Sequence analysis confirmed that cosmid L12287 contained the complete AIRE coding sequence consisting of 14 exons spanning 13,276 bp from the proposed initiation codon to the termination codon, which compares with 11,714 bp for the human gene (FIG. 12). The mouse AIRE intron/exon boundaries were confirmed experimentally after alignment of mouse cDNA and genomic sequences. Data are summarized in Table 2A and 2B. In both species, splice acceptor and splice donor sequences were found to conform to the GT-AG rule, and the intron phase is completely conserved. Sizes of coding exons ranges from 63 to 181 bp in human, versus 69 to 177 bp in mouse. The GC content of the mouse AIRE coding sequence is 61% whereas that of the human is 67,7 %. The overall nucleotide sequence identity between the mouse AIRE coding sequence and that of the human is 76.67 %.

Figure 13A:
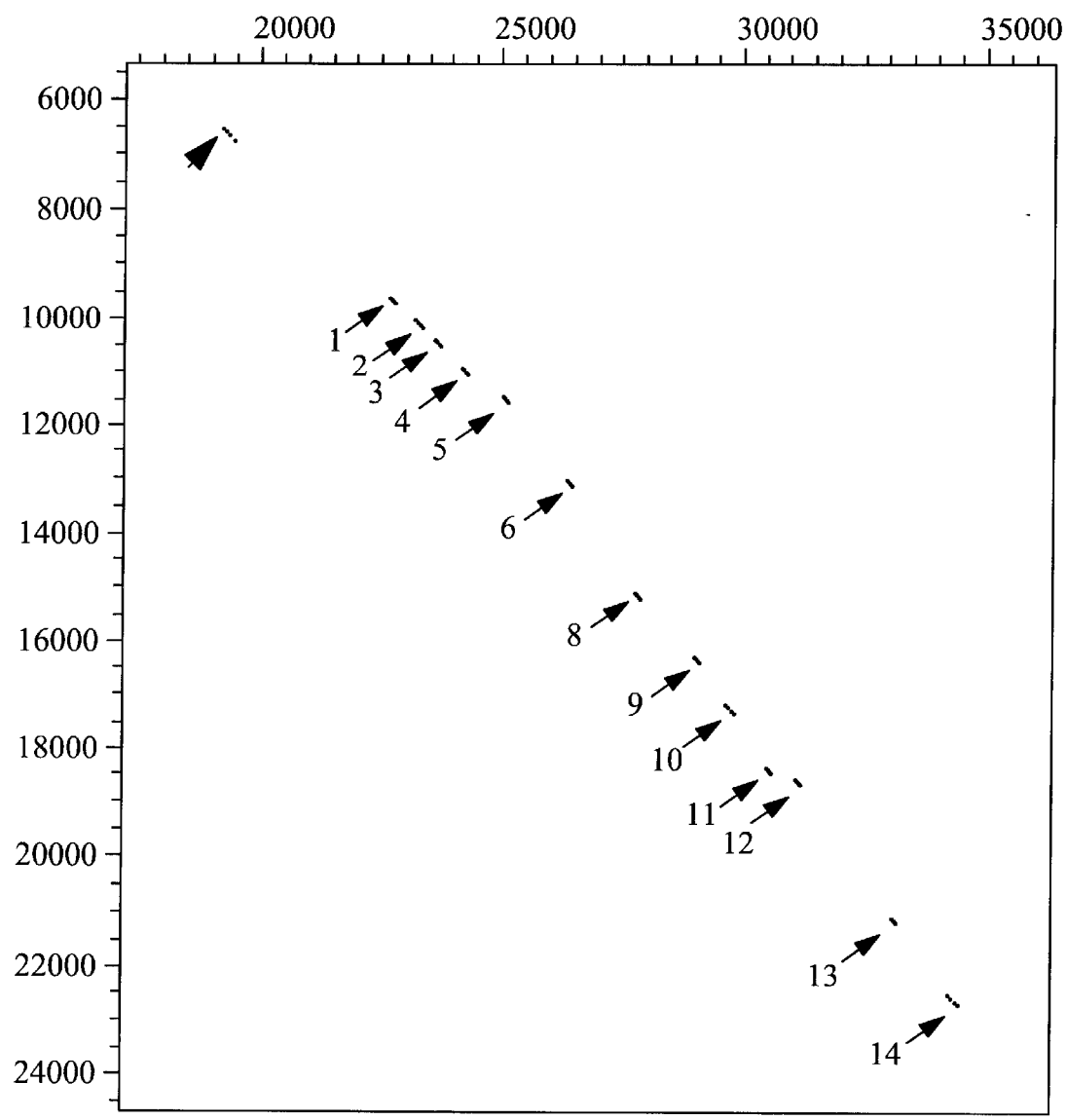

A TATA box was found in a conserved position less than 200 bp upstream of the putative translation initiation site, at position 9,413 and 22,486 of the mouse and human sequences, respectively. A CpG island was identified immediately upstream of the AIRE gene in both species (see FIG. 1). In order to detect potentially conserved regulatory regions, sequence comparison was represented in a dot-matrix using the dotter program (Erik L. L. Sonnhammer and Richard Durbin, Gene 167:GC1-10 (1995)) (FIG. 13A). The plot shows clear identification of exons 1 to 11 and of the terminal exon, whereas exons 12 and 13 are below threshold indicating higher sequence divergence for these 2 exons (FIG. 13A). Interestingly, a conserved region of approximately 100 nucleotides was identified 3 kb upstream of the AIRE first exon suggesting that this region may be potentially relevant to the expression of the AIRE gene (FIG. 13B).

EXAMPLE 20

Localization of the mAIRE Gene to Chromosome 10

Figure 15:
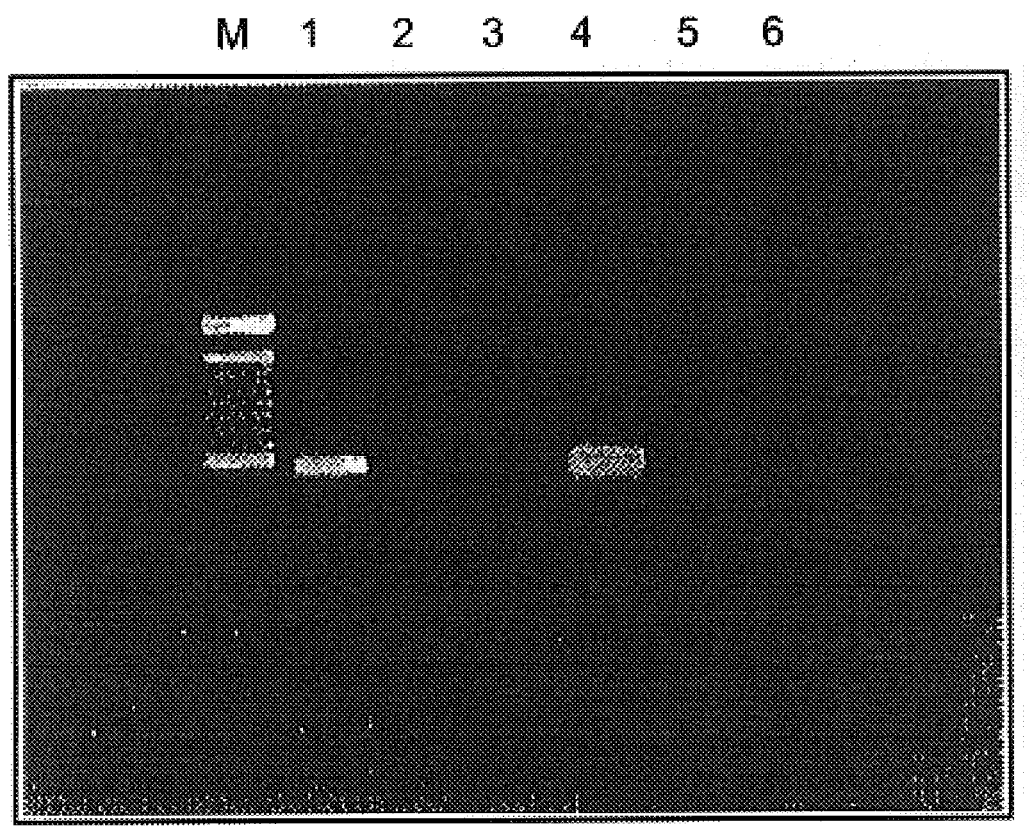

Comparative mapping between mice and human has shown that human chromosome 21q22.3 shares conserved synteny with mouse chromosomes 10 and 17. Then, the chromosomal localization of AIRE was determined by PCR analysis of monochromosomal hybrids containing mouse chromosomes 10 or 17. A primer set derived from the genomic sequence (see Example 16) amplified a specific band in total mouse gename and chromosome 10. FIG. 15 demonstrates that this fragment is mouse-specific and different to that amplified in human DNA. Data are consistent with the expected conserved synteny in this region.

The predicted mouse AIRE protein (mAIRE) is 552 residues and has a calculated pI of 8.43 and a theoretical molecular weight of 59 kDa. The overall identity between the mouse and human AIRE proteins is 72,37 % and similarity is 74,58 %. The two proteins are remarkably conserved and harbor the modular domains described for the human protein. These features include a N-terminal LXXLL motif located in a putative helical region that is a signature for nuclear receptor binding, a nuclear targeting signal, a SAND domain that was recently described as potential DNA binding domain, and two PHD-type zinc finger motifs (FIG. 16). Essential residues are conserved between the two species. The two protein are likewise proline rich (11 %) and have a predicted globular secondary structure. AIRE possibly encodes for a chromatin-associated transcription factor on the basis of its functional attributes shared by other nuclear PHD zinc finger proteins involved in transcriptional control.

EXAMPLE 21

AIRE Gene Expression

Figure 17A:
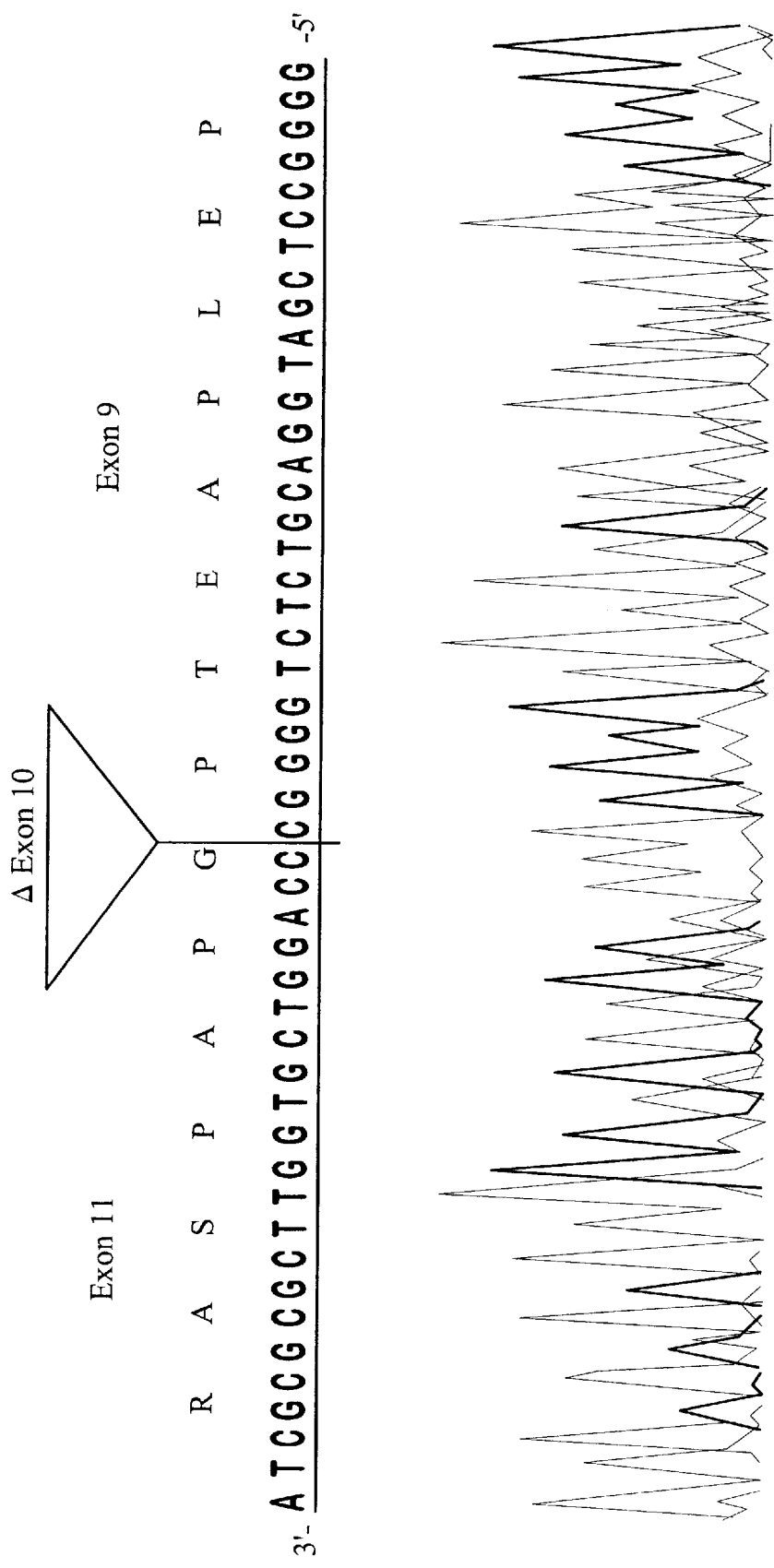
Figure 17B:
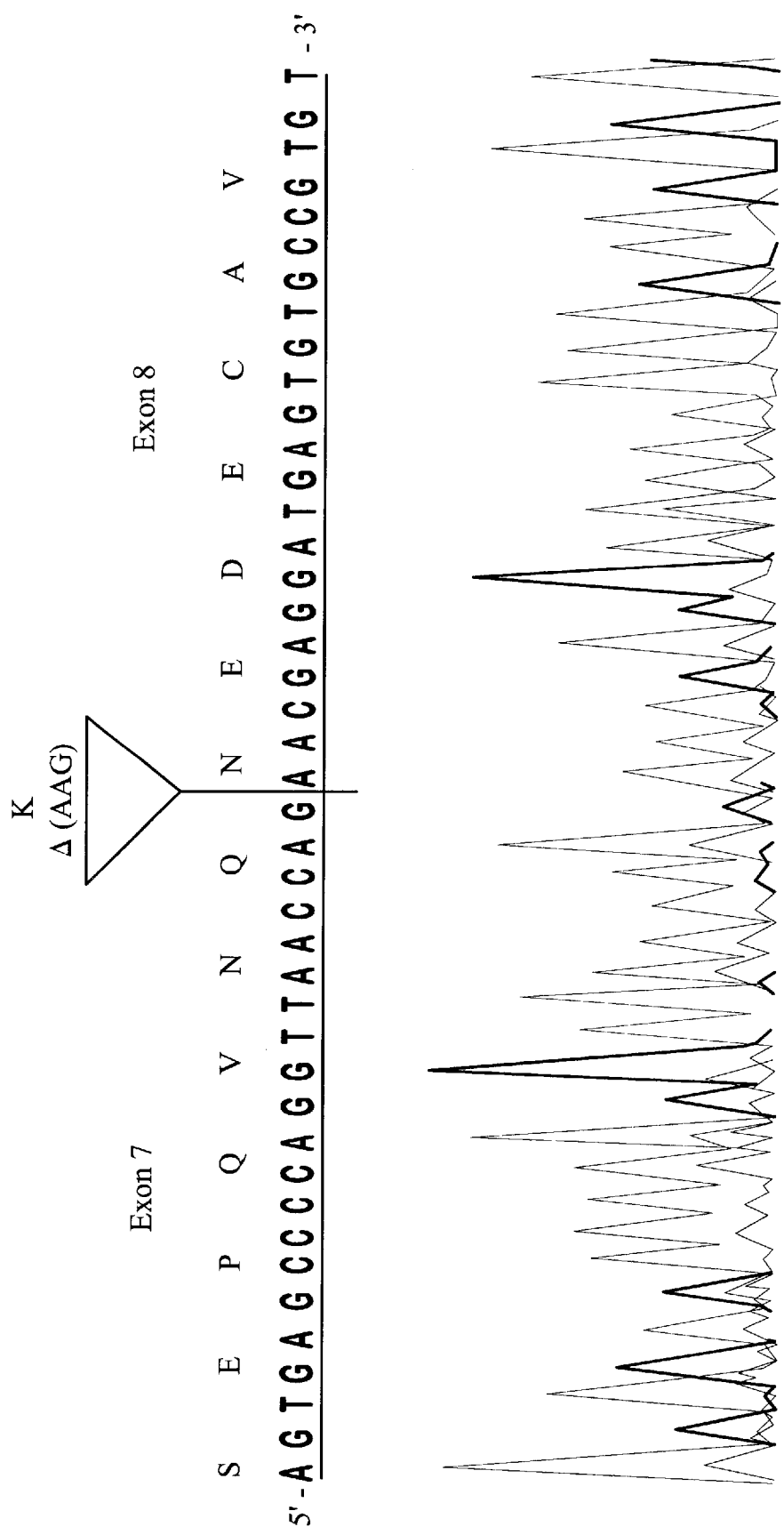
Figure 17C:
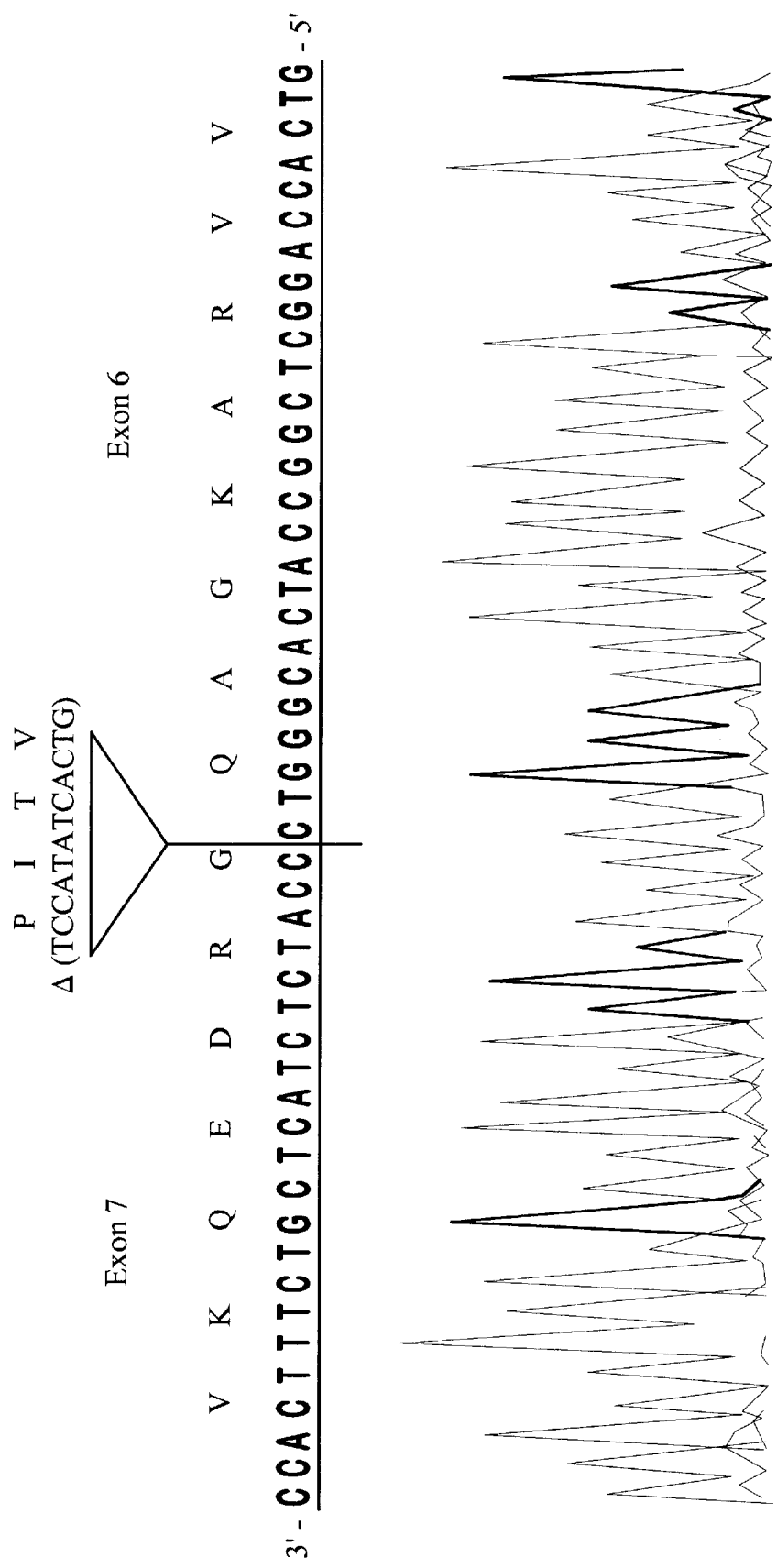

AIRE transcripts were detected by PCR amplification from mouse cDNAs derived from a wide range of tissues. Sequenced PCR fragments confirmed the presence of AIRE cDNAs in ES cells, 11 days embryo, spleen, lung, heart, skeletal muscle and testis. The complete mouse cDNA sequence was deduced from overlapping PCR fragments amplified in ES cells. Evidence for 3 alternatively spliced isoform transcripts was also observed and these were designated type I, II and III. One variant found present in ES cells corresponds to skipping of exon 10 (Type I; FIG. 17A). If translated, variant type I would lead to a protein with only a small spacer between the two PHD fingers. A second splice variant found in ES cells and testis correspond to a 3 bp deletion in the splice acceptor site in exon 8, leading to a shorter exon 8 (Type II; FIG. 17B). The predicted protein for type II is similar to canonical AIRE with only with a missing lysine at the beginning of exon 8. The third splice variant that was observed in 11 days embryo, heart, testis and spleen was a 12 bp shorter exon 6 consecutive to a change in exon 6 splice donor site (type III; FIG. 17C). The predicted peptide is 4 residues shorter at the end of exon 6 as compared to normal AIRE. In ES cells, type III was observed in combination with variant type II or in a combination with the types I and II in the same cDNA molecule.

Figure 18:
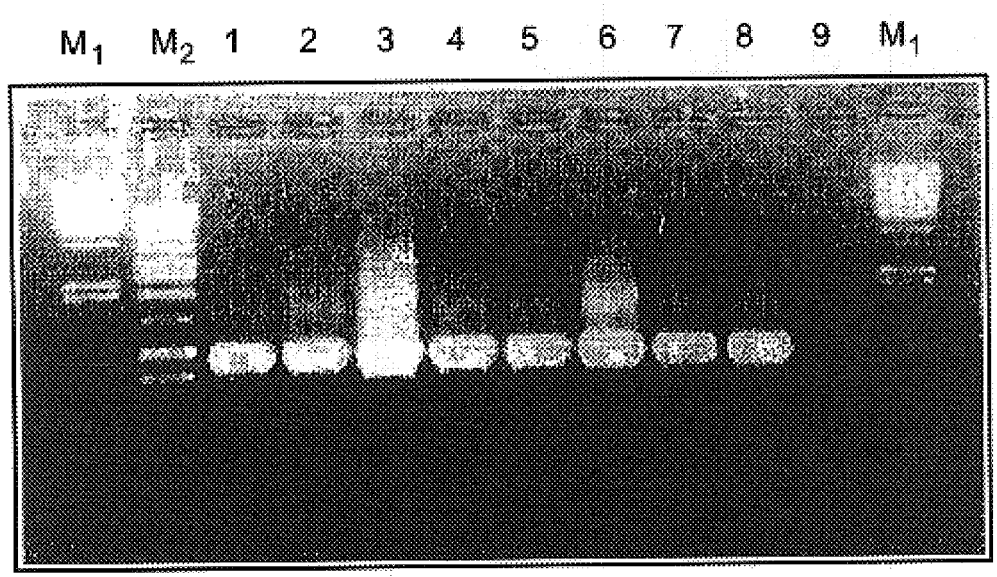

Expression of human AIRE was assessed in a panel of cDNA from various immunological tissues (FIG. 18). Sequenced PCR products indicated that AIRE was expressed in fetal liver, lymph node, peripheral blood leukocyte, thymus, bone marrow and spleen. Interestingly, the splice variant type II described above was also found in two human tissues, spleen and bone marrow. However, the data did not address whether alternative splicing leading to the two other variants was conserved between the two species.

TABELLE 1

Mutations in the APGD1 gene

| Mutation | No. | Exon | Nucleotide | Haplotype | No. | Consequence |
|---|---|---|---|---|---|---|
| $C_{889}$ -> $T_{Fin\ major}$ | 1 | 6 | 889 | (4 3 5 1 2) | 1.1 | Arg -> STOP, truncated 256 aa protein |
|  |  |  |  | (4 4 7 4 5) | 1.2 |  |
|  |  |  |  | (5 4 2 2 5) | 1.3 |  |
|  |  |  |  | (5 4 5 4 3) | 1.4 |  |
| 4 bp insertion | 2 | 8 | 1086–1089 | (5 3 5 3 3) | 2.1 | frame shift, truncated 371 aa protein |
| 13 bp deletion | 3 | 8 | 1085–1097 | (4 5 5 4 5) | 3.1 | frame shift, truncated 372 aa protein |
| A insertion | 4 | 10 | 1284 | (5 4 3 2 5) | 4.1 | frame shift, truncated 422 aa protein |
| C deletion | 5 | 10 | 1313 | (2 10 7 4 5) | 5.1 | frame shift, truncated 478 aa protein |

Table 1 summarizes the mutations and the predicted consequences for the APGD1 putative protein. The APGD1 exons were amplified with intronic primers and initially screened by the SSCP method (Orita, M., et al., *Proc. Natl. Acad. Sci. USA,* 86, 2766–2770 (1989)). Detected changes were characterized by solid-phase sequencing (Syvanen, A. C., et al., *FEBS Lett.,* 258, 71–74 (1989)). The haplotypes of the disease chromosomes were constructed from alleles of the markers shown in FIG. 1A (cen—JA1, D21S1912, PFKL(CA)$_n$, PB1, D21S171—tel). Haplotype 1.1 is the major haplotype in Finland (Fin major). Haplotypes 1.2 (Italian), 1.3 (German) and 1.4 (German) carry the same mutation as the major Finnish allele. Haplotypes 1.3 and 1.4 are most probably of the same origin since they share the same centromeric alleles. An Italian patient was homozygous for haplotype 2.1 and mutation 2. Haplotype 3.1 was observed as homozygous in one Dutch and in two British patients, and as heterozygous in one German patient. All chromosomes carrying this haplotype have mutation 3. Two Finnish patients were compound heterozygotes for haplotype 4.1 and for mutation 4. Haplotype 5.1 and mutation 5 were found homozygous in a French patient. The detected mutations were monitored against a control panel (see text) by minisequencing (Syvänen, A. C., et al., *Am. J. Hum. Genet.,* 52, 46–59 (1993)) (mutations 1, 4 and 5) or by size separation of radioactively labeled PCR products on denaturing PAGE (mutations 2 and 3). None of these mutations were detected in a homozygous form in the control subjects. The carrier frequency of the Fin major mutation was observed to be 1:250 in the Finland. This mutation was also found in a heterozygous form in one CEPH parent whereas we did not detect any carriers for the other mutations.

TABELLE 2A

| Exon | Size (bp) | Position in cDNA | Position in genomic DNA | Intron size (bp) | Splice acceptor | Splice donor | Intron phase |
|---|---|---|---|---|---|---|---|
| 1 | 132 | 121–252 | 22648–22779 | 418 | 5' UTR | CAGgtggg | 0 |
| 2 | 175 | 253–427 | 23198–23372 | 246 | tgcagAG | AAGgtggg | 1 |
| 3 | 156 | 428–583 | 23619–23774 | 383 | tgcagATG | CAGgtacc | 1 |
| 4 | 75 | 584–658 | 24158–24232 | 753 | ttcagGCT | ACGgtgag | 1 |
| 5 | 112 | 659–772 | 24986–25099 | 1198 | cccagGGA | CAGgtaga | 1 |
| 6 | 144 | 773–918 | 26298–26443 | 185 | cccagGCG | CCCgtaag | 0 |
| 7 | 81 | 919–999 | 26629–26709 | 1026 | tgcagGGT | CAGgtaat | 0 |
| 8 | 116 | 1000–1115 | 27736–27851 | 1091 | gccagAAG | CAGgtgag | 2 |
| 9 | 100 | 1116–1215 | 28943–29042 | 590 | agcagTGG | CCGgtatg | 0 |
| 10 | 181 | 1216–1398 | 29633–29815 | 612 | tccagCTC | CAGgtgag | 0 |
| 11 | 122 | 1399–1520 | 30428–30549 | 490 | cacagAAC | CGGgtgag | 2 |
| 12 | 103 | 1521–1623 | 31040–31142 | 1879 | tgcagGAC | AAGgtcag | 0 |
| 13 | 63 | 1624–1686 | 33022–33084 | 1206 | tccagGAT | GAGgtaac | 0 |
| 14 |  | 1687–1755 | 34291–34359 |  | cgcagCAC | 3' UTR after stop |  | human AIRE gene structure information
Numbering of exon 1 begins from translation start site (A of ATG start codon is posit 1):
Numbering of exon 14 ends at the stop codon. The exon location in the cDNA sequence correspond to EMBL accession no. Z97990, and the exon location in the genomic sequence correspond to GenBank accession no. ? WEB C.741.

TABELLE 2B

| Exon | Size (bp) | Position in cDNA | Position in genomic DNA | Intron size (bp) | Splice acceptor | Splice donor | Intron phase |
|---|---|---|---|---|---|---|---|
| 1 | 135 | 1–135 | 9555–9689 | 312 | 5' UTR | CAGgtggg | 0 |
| 2 | 175 | 136–310 | 10002–10176 | 229 | tgcagGAG | AAGgtggg | 1 |
| 3 | 156 | 311–466 | 10406–10561 | 381 | tgcagATG | CAGgtaca | 1 |
| 4 | 75 | 467–541 | 10943–11017 | 447 | cgcagGCT | ACGgtgag | 1 |
| 5 | 114 | 542–655 | 11465–11578 | 1420 | tccagGAA | CAGgtaaa | 1 |
| 6 | 149 | 656–804 | 12999–13147 | 188 | cccagGAA | CCTgtaag | 0 |
| 7 | 81 | 805–885 | 13336–13416 | 1674 | catagGGT | CAGgtaag | 0 |
| 8 | 116 | 886–1001 | 15091–15206 | 1088 | gtcagAAG | CAGgtaag | 2 |
| 9 | 100 | 1002–1101 | 16295–16394 | 851 | cacagTGG | CCGgtagt | 0 |
| 10 | 177 | 1102–1278 | 17246–17422 | 949 | tccagATC | CCAgtgag | 0 |
| 11 | 122 | 1279–1400 | 18372–18493 | 96 | tgcagGGT | GGGgtgag | 2 |
| 12 | 109 | 1401–1509 | 18590–18698 | 2491 | gacagGAC | AAGgtcag | 0 |
| 13 | 69 | 1510–1578 | 21190–21258 | 1492 | tccagGTA | GAGgtaat | 0 |
| 14 | 78 | 1579–1656 | 22751–22828 |  | ctcagCAC | 3' UTR after stop |  | mAIRE gene structure information
Numbering of exon 1 begins from translation start site (A of ATG start codon is posit 1):
Numbering of exon 14 ends at the stop codon. The exon location in the cDNA sequence correspond to EMBL accession no. ???, and the exon location in the genomic sequence correspond to GenBank accession no. AF073797.

What is claimed is:

1. An isolated nucleic acid molecule comprising a contiguous coding region encoding the polypeptide having the amino acid sequence of SEQ ID NO:2.

2. The isolated nucleic acid molecule of claim 1 wherein the molecule is DNA or RNA.

3. An isolated nucleic acid molecule according to claim 1, wherein the nucleic acid molecule comprises the nucleotide sequence of SEQ ID NO:1.

4. The isolated nucleic acid molecule of claim 1, wherein the nucleic acid molecule consists of the contiguous nucleotide sequence of SEQ ID NO:1, or the coding region thereof that encodes the polypeptide of SEQ ID NO:2.

5. An isolated nucleic acid molecule differing from the nucleic acid sequence of SEQ ID NO:1 by an insertion, wherein the insertion is:

a) an insertion of CCTG at position 1086;

b) a 4 nucleotide insertion at the nucleotide position 1085 or 1090;

c) an insertion of an adenosine at position 1284; or d) an insertion of a cytosine at position 1365 of the nucleotide sequence of SEQ ID NO: 1.

6. An isolated nucleic acid molecule which is complementary to a nucleic acid molecule of claim 1 or claim 5.

7. An isolated nucleic acid molecule differing from the nucleic acid sequence of SEQ ID NO:1 by a deletion, wherein the deletion is:

a) a 13 nucleotide deletion of nucleotides 1085–1097;

b) a deletion of the thymidine at position 1051; or c) a deletion of the cytosine at position 1309 or 1313 of the nucleic acid sequence of SEQ ID NO:1.

8. An isolated nucleic acid molecule differing from the nucleic acid sequence of SEQ ID NO:1 by a substitution, wherein the substitution is: changes of cytosine to thymidine at nucleotide position 889, guanosine to thymidine at nucleotide position 358, adenosine to guanosine at nucleotide position 374, guanosine to adenosine at nucleotide position 1052, or cytosine to adenosine at nucleotide position 1094.

9. The nucleic acid molecule of claim 8, wherein said substitution is a cytosine to thymidine exchange at nucleotide position 889 of SEQ ID NO:1.

10. An isolated vector comprising the nucleic acid molecule of claim 1, claim 5, or claim 4.

11. An isolated host cell transformed with a vector of claim 10.

12. The host of claim 11 which is a bacterium, a yeast cell, an insect cell, a fungal cell, a mammalian cell, or a plant cell.

13. An isolated nucleic acid molecule encoding the polypeptide having the amino acid sequence of SEQ ID NO:9.

14. The isolated nucleic acid molecule of claim 13 wherein the molecule is a murine homologue.

15. The isolated nucleic acid molecule of claim 14, wherein the nucleic acid molecule comprises SEQ ID NO:6.

16. A method of producing a polypeptide encoded by the nucleic acid molecule of claim 1, comprising culturing an isolated host cell transformed with a vector comprising a nucleic acid molecule of claim 1 and isolating said polypeptide.

* * * * *

SEQUENCE LISTING

<160> NUMBER OF SEQ ID NOS: 30

<210> SEQ ID NO 1
<211> LENGTH: 2245
<212> TYPE: DNA
<213> ORGANISM: Homo sapiens
<220> FEATURE:
<221> NAME/KEY: CDS
<222> LOCATION: (121)..(1758)
<223> OTHER INFORMATION:

<400> SEQUENCE: 1

```
cgggcgcaca gccggcgcgg aggccccaca gccccgccgg gacccgaggc caagcgaggg      60
gctgccagtg tcccgggacc caccgcgtcc gccccagccc cgggtcccccg cgcccacccc    120 atg gcg acg gac gcg gcg cta cgc cgg ctt ctg agg ctg cac cgc acg       168
Met Ala Thr Asp Ala Ala Leu Arg Arg Leu Leu Arg Leu His Arg Thr
1               5                   10                  15 gag atc gcg gtg gcc gtg gac agc gcc ttc cca ctg ctg cac gcg ctg       216
Glu Ile Ala Val Ala Val Asp Ser Ala Phe Pro Leu Leu His Ala Leu
                20                  25                  30 gct gac cac gac gtg gtc ccc gag gac aag ttt cag gag acg ctt cat       264
Ala Asp His Asp Val Val Pro Glu Asp Lys Phe Gln Glu Thr Leu His
            35                  40                  45 ctg aag gaa aag gag ggc tgc ccc cag gcc ttc cac gcc ctc ctg tcc       312
Leu Lys Glu Lys Glu Gly Cys Pro Gln Ala Phe His Ala Leu Leu Ser
        50                  55                  60 tgg ctg ctg acc cag gac tcc aca gcc atc ctg gac ttc tgg agg gtg       360
Trp Leu Leu Thr Gln Asp Ser Thr Ala Ile Leu Asp Phe Trp Arg Val
65                  70                  75                  80 ctg ttc aag gac tac aac ctg gag cgc tat ggc cgg ctg cag ccc atc       408
Leu Phe Lys Asp Tyr Asn Leu Glu Arg Tyr Gly Arg Leu Gln Pro Ile
                85                  90                  95 ctg gac agc ttc ccc aaa gat gtg gac ctc agc cag ccc cgg aag ggg       456
Leu Asp Ser Phe Pro Lys Asp Val Asp Leu Ser Gln Pro Arg Lys Gly
                100                 105                 110 agg aag ccc ccg gcc gtc ccc aag gct ttg gta ccg cca ccc aga ctc       504
Arg Lys Pro Pro Ala Val Pro Lys Ala Leu Val Pro Pro Pro Arg Leu
            115                 120                 125 ccc acc aag agg aag gcc tca gaa gag gct cga gct gcc gcg cca gca       552
Pro Thr Lys Arg Lys Ala Ser Glu Glu Ala Arg Ala Ala Ala Pro Ala
        130                 135                 140 gcc ctg act cca agg ggc acc gcc agc cca ggc tct caa ctg aag gcc       600
Ala Leu Thr Pro Arg Gly Thr Ala Ser Pro Gly Ser Gln Leu Lys Ala
145                 150                 155                 160 aag ccc ccc aag aag ccg gag agc agc gca gag cag cag cgc ctt cca       648
Lys Pro Pro Lys Lys Pro Glu Ser Ser Ala Glu Gln Gln Arg Leu Pro
                165                 170                 175 ctc ggg aac ggg att cag acc atg tca gct tca gtc cag aga gct gtg       696
Leu Gly Asn Gly Ile Gln Thr Met Ser Ala Ser Val Gln Arg Ala Val
            180                 185                 190 gcc atg tcc tcc ggg gac gtc ccg gga gcc cga ggg gcc gtg gag ggg       744
Ala Met Ser Ser Gly Asp Val Pro Gly Ala Arg Gly Ala Val Glu Gly
        195                 200                 205 atc ctc atc cag cag gtg ttt gag tca ggc ggc tcc aag aag tgc atc       792
Ile Leu Ile Gln Gln Val Phe Glu Ser Gly Gly Ser Lys Lys Cys Ile
    210                 215                 220 cag gtt ggt ggg gag ttc tac act ccc agc aag ttc gaa gac tcc ggc       840
Gln Val Gly Gly Glu Phe Tyr Thr Pro Ser Lys Phe Glu Asp Ser Gly
225                 230                 235                 240
```

```
agt ggg aag aac aag gcc cgc agc agc agt ggc ccg aag cct ctg gtt        888
Ser Gly Lys Asn Lys Ala Arg Ser Ser Ser Gly Pro Lys Pro Leu Val
            245                 250                 255 cga gcc aag gga gcc cag ggc gct gcc ccc ggt gga ggt gag gct agg        936
Arg Ala Lys Gly Ala Gln Gly Ala Ala Pro Gly Gly Gly Glu Ala Arg
        260                 265                 270 ctg ggc cag cag ggc agc gtt ccc gcc cct ctg gcc ctc ccc agt gac        984
Leu Gly Gln Gln Gly Ser Val Pro Ala Pro Leu Ala Leu Pro Ser Asp
        275                 280                 285 ccc cag ctc cac cag aag aat gag gac gag tgt gcc gtg tgt cgg gac       1032
Pro Gln Leu His Gln Lys Asn Glu Asp Glu Cys Ala Val Cys Arg Asp
        290                 295                 300 ggc ggg gag ctc atc tgc tgt gac ggc tgc cct cgg gcc ttc cac ctg       1080
Gly Gly Glu Leu Ile Cys Cys Asp Gly Cys Pro Arg Ala Phe His Leu
305                 310                 315                 320 gcc tgc ctg tcc cct ccg ctc cgg gag atc ccc agt ggg acc tgg agg       1128
Ala Cys Leu Ser Pro Pro Leu Arg Glu Ile Pro Ser Gly Thr Trp Arg
                325                 330                 335 tgc tcc agc tgc ctg cag gca aca gtc cag gag gtg cag ccc cgg gca       1176
Cys Ser Ser Cys Leu Gln Ala Thr Val Gln Glu Val Gln Pro Arg Ala
            340                 345                 350 gag gag ccc cgg ccc cag gag cca ccc gtg gag acc ccg ctc ccc ccg       1224
Glu Glu Pro Arg Pro Gln Glu Pro Pro Val Glu Thr Pro Leu Pro Pro
        355                 360                 365 ggg ctt agg tcg gcg gga gag gag gta aga ggt cca cct ggg gaa ccc       1272
Gly Leu Arg Ser Ala Gly Glu Glu Val Arg Gly Pro Pro Gly Glu Pro
        370                 375                 380 cta gcc ggc atg gac acg act ctt gtc tac aag cac ctg ccg gct ccg       1320
Leu Ala Gly Met Asp Thr Thr Leu Val Tyr Lys His Leu Pro Ala Pro
385                 390                 395                 400 cct tct gca gcc ccg ctg cca ggg ctg gac tcc tcg gcc ctg cac ccc       1368
Pro Ser Ala Ala Pro Leu Pro Gly Leu Asp Ser Ser Ala Leu His Pro
                405                 410                 415 cta ctg tgt gtg ggt cct gag ggt cag cag aac ctg gct cct ggt gcg       1416
Leu Leu Cys Val Gly Pro Glu Gly Gln Gln Asn Leu Ala Pro Gly Ala
            420                 425                 430 cgt tgc ggg gtg tgc gga gat ggt acg gac gtg ctg cgg tgt act cac       1464
Arg Cys Gly Val Cys Gly Asp Gly Thr Asp Val Leu Arg Cys Thr His
        435                 440                 445 tgc gcc gct gcc ttc cac tgg cgc tgc cac ttc cca gcc ggc acc tcc       1512
Cys Ala Ala Ala Phe His Trp Arg Cys His Phe Pro Ala Gly Thr Ser
450                 455                 460 cgg ccc ggg acg ggc ctg cgc tgc aga tcc tgc tca gga gac gtg acc       1560
Arg Pro Gly Thr Gly Leu Arg Cys Arg Ser Cys Ser Gly Asp Val Thr
465                 470                 475                 480 cca gcc cct gtg gag ggg gtg ctg gcc ccc agc ccc gcc cgc ctg gcc       1608
Pro Ala Pro Val Glu Gly Val Leu Ala Pro Ser Pro Ala Arg Leu Ala
                485                 490                 495 cct ggg cct gcc aag gat gac act gcc agt cac gag ccc gct ctg cac       1656
Pro Gly Pro Ala Lys Asp Asp Thr Ala Ser His Glu Pro Ala Leu His
                500                 505                 510 agg gat gac ctg gag tcc ctt ctg agc gag cac acc ttc gat ggc atc       1704
Arg Asp Asp Leu Glu Ser Leu Leu Ser Glu His Thr Phe Asp Gly Ile
            515                 520                 525 ctg cag tgg gcc atc cag agc atg gcc gtt ccg gcg gcc ccc ttc ccc       1752
Leu Gln Trp Ala Ile Gln Ser Met Ala Arg Pro Ala Ala Pro Phe Pro
        530                 535                 540 tcc tga ccccagatgg ccgggacatg cagctctgat gagagagtgc tgagaaggac        1808
Ser
```

-continued

```
545
acctccttcc tcagtcctgg aagccggccg gctgggatca agaagggggac agcgccacct     1868 cttgtcagtg ctcggctgta acagctctg tgtttctggg gacaccagcc atcatgtgcc      1928
tggaaattaa accctgcccc acttctctac tctggaagtc cccgggagcc tctccttgcc     1988
tggtgaccta ctaaaaatat aaaaattagc tgggtgtggt ggtgggtgcc tgtaatccca     2048
gctacatggg agcctgaggc atgagaatca cttgaactcg ggaggtggag gttgcagtga    2108
gctgagattg cgccactgca ctccagtctg gtcggcaaga gtgagactcc gtctcaaaaa    2168
caaaacaaaa aaaccacata acataaattt atcatctcga ccacttttca gttcagtggc   2228
attcacatct catgtaa                                                   2245
```

<210> SEQ ID NO 2
<211> LENGTH: 545
<212> TYPE: PRT
<213> ORGANISM: Homo sapiens

<400> SEQUENCE: 2

```
Met Ala Thr Asp Ala Ala Leu Arg Arg Leu Leu Arg Leu His Arg Thr
1               5                   10                  15

Glu Ile Ala Val Ala Val Asp Ser Ala Phe Pro Leu Leu His Ala Leu
                20                  25                  30

Ala Asp His Asp Val Val Pro Glu Asp Lys Phe Gln Glu Thr Leu His
            35                  40                  45

Leu Lys Glu Lys Glu Gly Cys Pro Gln Ala Phe His Ala Leu Leu Ser
        50                  55                  60

Trp Leu Leu Thr Gln Asp Ser Thr Ala Ile Leu Asp Phe Trp Arg Val
65                  70                  75                  80

Leu Phe Lys Asp Tyr Asn Leu Glu Arg Tyr Gly Arg Leu Gln Pro Ile
                85                  90                  95

Leu Asp Ser Phe Pro Lys Asp Val Leu Ser Gln Pro Arg Lys Gly
                100                 105                 110

Arg Lys Pro Pro Ala Val Pro Lys Ala Leu Val Pro Pro Arg Leu
            115                 120                 125

Pro Thr Lys Arg Lys Ala Ser Glu Glu Ala Arg Ala Ala Pro Ala
        130                 135                 140

Ala Leu Thr Pro Arg Gly Thr Ala Ser Pro Gly Ser Gln Leu Lys Ala
145                 150                 155                 160

Lys Pro Pro Lys Lys Pro Glu Ser Ser Ala Glu Gln Gln Arg Leu Pro
                165                 170                 175

Leu Gly Asn Gly Ile Gln Thr Met Ser Ala Ser Val Gln Arg Ala Val
            180                 185                 190

Ala Met Ser Ser Gly Asp Val Pro Gly Ala Arg Gly Ala Val Glu Gly
        195                 200                 205

Ile Leu Ile Gln Gln Val Phe Glu Ser Gly Gly Ser Lys Lys Cys Ile
    210                 215                 220

Gln Val Gly Gly Glu Phe Tyr Thr Pro Ser Lys Phe Glu Asp Ser Gly
225                 230                 235                 240

Ser Gly Lys Asn Lys Ala Arg Ser Ser Ser Gly Pro Lys Pro Leu Val
                245                 250                 255

Arg Ala Lys Gly Ala Gln Gly Ala Ala Pro Gly Gly Gly Glu Ala Arg
            260                 265                 270

Leu Gly Gln Gln Gly Ser Val Pro Ala Pro Leu Ala Leu Pro Ser Asp
        275                 280                 285
```

-continued

```
Pro Gln Leu His Gln Lys Asn Glu Asp Glu Cys Ala Val Cys Arg Asp
    290                 295                 300
Gly Gly Glu Leu Ile Cys Cys Asp Gly Cys Pro Arg Ala Phe His Leu
305                 310                 315                 320
Ala Cys Leu Ser Pro Pro Leu Arg Glu Ile Pro Ser Gly Thr Trp Arg
                325                 330                 335
Cys Ser Ser Cys Leu Gln Ala Thr Val Gln Glu Val Gln Pro Arg Ala
            340                 345                 350
Glu Glu Pro Arg Pro Gln Glu Pro Val Glu Thr Pro Leu Pro Pro
        355                 360                 365
Gly Leu Arg Ser Ala Gly Glu Glu Val Arg Gly Pro Pro Gly Glu Pro
    370                 375                 380
Leu Ala Gly Met Asp Thr Thr Leu Val Tyr Lys His Leu Pro Ala Pro
385                 390                 395                 400
Pro Ser Ala Ala Pro Leu Pro Gly Leu Asp Ser Ser Ala Leu His Pro
                405                 410                 415
Leu Leu Cys Val Gly Pro Glu Gly Gln Gln Asn Leu Ala Pro Gly Ala
            420                 425                 430
Arg Cys Gly Val Cys Gly Asp Gly Thr Asp Val Leu Arg Cys Thr His
        435                 440                 445
Cys Ala Ala Ala Phe His Trp Arg Cys His Phe Pro Ala Gly Thr Ser
    450                 455                 460
Arg Pro Gly Thr Gly Leu Arg Cys Arg Ser Cys Ser Gly Asp Val Thr
465                 470                 475                 480
Pro Ala Pro Val Glu Gly Val Leu Ala Pro Ser Pro Ala Arg Leu Ala
                485                 490                 495
Pro Gly Pro Ala Lys Asp Asp Thr Ala Ser His Glu Pro Ala Leu His
            500                 505                 510
Arg Asp Asp Leu Glu Ser Leu Leu Ser Glu His Thr Phe Asp Gly Ile
        515                 520                 525
Leu Gln Trp Ala Ile Gln Ser Met Ala Arg Pro Ala Ala Pro Phe Pro
    530                 535                 540
Ser
545

<210> SEQ ID NO 3
<211> LENGTH: 90
<212> TYPE: DNA
<213> ORGANISM: Murine

<400> SEQUENCE: 3
gtgtggactg tcacggaaac ccccacgtgt gatggaaagt ccaaaattct acaggagtct      60
ttctgttgat ctccagtcag aggctggggg                                      90

<210> SEQ ID NO 4
<211> LENGTH: 90
<212> TYPE: DNA
<213> ORGANISM: Homo sapiens

<400> SEQUENCE: 4
aaggggctgg tgtggaaagc cccacggcat ggtggaaagt ccgaaattct acaggggcct      60
ctttgttaaa cctccatgca agaggctggg                                      90

<210> SEQ ID NO 5
<211> LENGTH: 90
```

```
<212> TYPE: DNA
<213> ORGANISM: Artificial sequence
<220> FEATURE:
<223> OTHER INFORMATION: Consensus sequence of SEQ ID NO:3 & SEQ ID NO:4
<220> FEATURE:
<221> NAME/KEY: misc_feature
<222> LOCATION: (1)..(90)
<223> OTHER INFORMATION: n is any nucleotide or a gap

<400> SEQUENCE: 5
nngnggnnng tnnngnaanc cccnnngnnt gntggaaagt ccnaaattct acaggngnct    60
ntntgttnan cnncnntnnn agnnnnnggg                                    90

<210> SEQ ID NO 6
<211> LENGTH: 1656
<212> TYPE: DNA
<213> ORGANISM: Murine
<220> FEATURE:
<221> NAME/KEY: CDS
<222> LOCATION: (1)..(1656)
<223> OTHER INFORMATION:

<400> SEQUENCE: 6
```

| | | | | | | | | | | | | | | | | |
|---|---|---|---|---|---|---|---|---|---|---|---|---|---|---|---|---|
| atg | gca | ggt | ggg | gat | gga | atg | cta | cgc | cgt | ctg | ctg | agg | ctg | cac | cgc | 48 |
| Met | Ala | Gly | Gly | Asp | Gly | Met | Leu | Arg | Arg | Leu | Leu | Arg | Leu | His | Arg | |
| 1 | | | | 5 | | | | | 10 | | | | | 15 | | |
| acc | gag | atc | gcg | gtg | gcc | ata | gac | agt | gcc | ttt | ccg | ctg | ctg | cat | gct | 96 |
| Thr | Glu | Ile | Ala | Val | Ala | Ile | Asp | Ser | Ala | Phe | Pro | Leu | Leu | His | Ala | |
| | | | 20 | | | | | 25 | | | | | 30 | | | |
| cta | gcc | gac | cac | gac | gtg | gtc | cct | gag | gac | aag | ttc | cag | gag | acg | ctc | 144 |
| Leu | Ala | Asp | His | Asp | Val | Val | Pro | Glu | Asp | Lys | Phe | Gln | Glu | Thr | Leu | |
| | 35 | | | | | 40 | | | | | 45 | | | | | |
| cgt | ctg | aag | gag | aag | gaa | ggc | tgc | ccc | cag | gcc | ttc | cac | gcc | ctg | ctg | 192 |
| Arg | Leu | Lys | Glu | Lys | Glu | Gly | Cys | Pro | Gln | Ala | Phe | His | Ala | Leu | Leu | |
| 50 | | | | | 55 | | | | | 60 | | | | | | |
| tcc | tgg | ctc | ctg | acc | cgg | gac | agt | ggg | gcc | atc | ctg | gat | ttc | tgg | agg | 240 |
| Ser | Trp | Leu | Leu | Thr | Arg | Asp | Ser | Gly | Ala | Ile | Leu | Asp | Phe | Trp | Arg | |
| 65 | | | | | 70 | | | | | 75 | | | | | 80 | |
| att | ctc | ttt | aag | gac | tac | aat | ctg | gag | cgg | tac | agc | cgc | ctg | cat | agc | 288 |
| Ile | Leu | Phe | Lys | Asp | Tyr | Asn | Leu | Glu | Arg | Tyr | Ser | Arg | Leu | His | Ser | |
| | | | | 85 | | | | | 90 | | | | | 95 | | |
| atc | ctg | gac | ggc | ttc | cca | aaa | gat | gtg | gac | cta | aac | cag | tcc | cgg | aaa | 336 |
| Ile | Leu | Asp | Gly | Phe | Pro | Lys | Asp | Val | Asp | Leu | Asn | Gln | Ser | Arg | Lys | |
| | | | 100 | | | | | 105 | | | | | 110 | | | |
| ggg | aga | aag | ccc | ctt | gct | ggt | ccc | aag | gcc | gcg | gta | ctg | cca | ccc | aga | 384 |
| Gly | Arg | Lys | Pro | Leu | Ala | Gly | Pro | Lys | Ala | Ala | Val | Leu | Pro | Pro | Arg | |
| | 115 | | | | | 120 | | | | | 125 | | | | | |
| ccc | ccc | acc | aag | aga | aaa | gca | ctg | gag | gag | cct | cga | gcc | acc | cca | cca | 432 |
| Pro | Pro | Thr | Lys | Arg | Lys | Ala | Leu | Glu | Glu | Pro | Arg | Ala | Thr | Pro | Pro | |
| 130 | | | | | 135 | | | | | 140 | | | | | | |
| gca | act | ctg | gcc | tca | aag | agc | gtc | tcc | agc | cca | ggc | tcc | cac | ctg | aag | 480 |
| Ala | Thr | Leu | Ala | Ser | Lys | Ser | Val | Ser | Ser | Pro | Gly | Ser | His | Leu | Lys | |
| 145 | | | | | 150 | | | | | 155 | | | | | 160 | |
| act | aag | ccc | cct | aag | aag | cca | gat | ggc | aac | ttg | gag | tca | cag | cac | ctt | 528 |
| Thr | Lys | Pro | Pro | Lys | Lys | Pro | Asp | Gly | Asn | Leu | Glu | Ser | Gln | His | Leu | |
| | | | | 165 | | | | | 170 | | | | | 175 | | |
| cct | ctt | gga | aac | gga | att | cag | acc | atg | gca | gct | tct | gtc | cag | aga | gct | 576 |
| Pro | Leu | Gly | Asn | Gly | Ile | Gln | Thr | Met | Ala | Ala | Ser | Val | Gln | Arg | Ala | |
| | | | 180 | | | | | 185 | | | | | 190 | | | |
| gtg | acc | gtg | gcc | tct | ggg | gat | gtt | cca | gga | acc | cga | ggg | gcc | gtg | gaa | 624 |
| Val | Thr | Val | Ala | Ser | Gly | Asp | Val | Pro | Gly | Thr | Arg | Gly | Ala | Val | Glu | |
| | 195 | | | | | 200 | | | | | 205 | | | | | |

-continued

| | |
|---|---|
| ggg atc ctt atc cag cag gtg ttt gag tca gga aga tcc aag aag tgc<br>Gly Ile Leu Ile Gln Gln Val Phe Glu Ser Gly Arg Ser Lys Lys Cys<br>210                         215                          220 | 672 |
| att cag gtt ggg gga gag ttt tat aca ccc aac aag ttc gaa gac ccc<br>Ile Gln Val Gly Gly Glu Phe Tyr Thr Pro Asn Lys Phe Glu Asp Pro<br>225                      230                      235                  240 | 720 |
| agt ggc aat ttg aag aac aag gcc cgg agt ggt agc agc cta aag cca<br>Ser Gly Asn Leu Lys Asn Lys Ala Arg Ser Gly Ser Ser Leu Lys Pro<br>                    245                      250                      255 | 768 |
| gtg gtc cga gcc aag gga gcc cag gtc act ata cct ggt aga gat gag<br>Val Val Arg Ala Lys Gly Ala Gln Val Thr Ile Pro Gly Arg Asp Glu<br>             260                      265                      270 | 816 |
| cag aaa gtg ggc cag cag tgt ggg gtt cct ccc ctt cca tcc ctc ccc<br>Gln Lys Val Gly Gln Gln Cys Gly Val Pro Pro Leu Pro Ser Leu Pro<br>275                         280                      285 | 864 |
| agt gag ccc cag gtt aac cag aag aac gag gat gag tgt gcc gtg tgc<br>Ser Glu Pro Gln Val Asn Gln Lys Asn Glu Asp Glu Cys Ala Val Cys<br>        290                      295                      300 | 912 |
| cac gac gga ggt gag ctc atc tgt tgt gac ggc tgt ccc cgg gcc ttc<br>His Asp Gly Gly Glu Leu Ile Cys Cys Asp Gly Cys Pro Arg Ala Phe<br>305                         310                      315                  320 | 960 |
| cac ctg gct tgc ctg tcc cca cct ctg cag gag atc ccc agt ggc ctc<br>His Leu Ala Cys Leu Ser Pro Pro Leu Gln Glu Ile Pro Ser Gly Leu<br>                    325                      330                      335 | 1008 |
| tgg aga tgc tcc tgc tgc ctc cag ggc aga gtc caa cag aac ctg tcc<br>Trp Arg Cys Ser Cys Cys Leu Gln Gly Arg Val Gln Gln Asn Leu Ser<br>                    340                      345                      350 | 1056 |
| cag cct gag gtg tcc agg ccc ccg gag cta cct gca gag acc ccg atc<br>Gln Pro Glu Val Ser Arg Pro Pro Glu Leu Pro Ala Glu Thr Pro Ile<br>                355                      360                      365 | 1104 |
| ctc gtg gga ctg agg tca gct tca gag aaa acc agg ggc cca tcc agg<br>Leu Val Gly Leu Arg Ser Ala Ser Glu Lys Thr Arg Gly Pro Ser Arg<br>370                         375                      380 | 1152 |
| gag ctc aaa gcc agc tct gat gct gct gtc aca tat gtg aac ctg ctg<br>Glu Leu Lys Ala Ser Ser Asp Ala Ala Val Thr Tyr Val Asn Leu Leu<br>385                         390                      395                  400 | 1200 |
| gcc ccg cac cct gca gct cct ctg ctg gag cct tca gca ctg tgc cct<br>Ala Pro His Pro Ala Ala Pro Leu Leu Glu Pro Ser Ala Leu Cys Pro<br>                    405                      410                      415 | 1248 |
| cta ctg agt gct ggg aat gag ggg cgg cca ggt cca gca cca agc gcg<br>Leu Leu Ser Ala Gly Asn Glu Gly Arg Pro Gly Pro Ala Pro Ser Ala<br>                    420                      425                      430 | 1296 |
| cga tgc agt gtg tgt ggc gat ggc acc gag gtg ttg cgg tgt gca cac<br>Arg Cys Ser Val Cys Gly Asp Gly Thr Glu Val Leu Arg Cys Ala His<br>                      435                      440                      445 | 1344 |
| tgt gcc gct gcc ttc cac tgg cgc tgc cac ttc ccg acg gcc gcc gcc<br>Cys Ala Ala Ala Phe His Trp Arg Cys His Phe Pro Thr Ala Ala Ala<br>450                         455                      460 | 1392 |
| cgg ccg ggg acc aat ctc cgc tgc aaa tcc tgc tct gca gac tcg act<br>Arg Pro Gly Thr Asn Leu Arg Cys Lys Ser Cys Ser Ala Asp Ser Thr<br>465                         470                      475                  480 | 1440 |
| ccc acg cca ggc aca ccg ggc gaa gct gta ccc acc tct ggg ccc cgt<br>Pro Thr Pro Gly Thr Pro Gly Glu Ala Val Pro Thr Ser Gly Pro Arg<br>                    485                      490                      495 | 1488 |
| cca gca cct ggg ctt gcc aag gta ggg gac gac tct gct agt cac gac<br>Pro Ala Pro Gly Leu Ala Lys Val Gly Asp Asp Ser Ala Ser His Asp<br>             500                      505                      510 | 1536 |
| cct gtt cta cat agg gac gac ctg gag tcc ctc ctc aat gag cac tca<br>Pro Val Leu His Arg Asp Asp Leu Glu Ser Leu Leu Asn Glu His Ser<br>515                         520                      525 | 1584 |

-continued

```
ttt gac ggc atc ctg cag tgg gcc atc cag agc atg tca cgc ccg ctg    1632
Phe Asp Gly Ile Leu Gln Trp Ala Ile Gln Ser Met Ser Arg Pro Leu
    530                 535                 540 gcc gag aca cca ccc ttc tct tcc                                    1656
Ala Glu Thr Pro Pro Phe Ser Ser
545                 550
```

<210> SEQ ID NO 7
<211> LENGTH: 552
<212> TYPE: PRT
<213> ORGANISM: Murine

<400> SEQUENCE: 7

```
Met Ala Gly Gly Asp Gly Met Leu Arg Arg Leu Leu Arg Leu His Arg
1               5                   10                  15

Thr Glu Ile Ala Val Ala Ile Asp Ser Ala Phe Pro Leu Leu His Ala
            20                  25                  30

Leu Ala Asp His Asp Val Val Pro Glu Asp Lys Phe Gln Glu Thr Leu
        35                  40                  45

Arg Leu Lys Glu Lys Glu Gly Cys Pro Gln Ala Phe His Ala Leu Leu
    50                  55                  60

Ser Trp Leu Leu Thr Arg Asp Ser Gly Ala Ile Leu Asp Phe Trp Arg
65                  70                  75                  80

Ile Leu Phe Lys Asp Tyr Asn Leu Glu Arg Tyr Ser Arg Leu His Ser
                85                  90                  95

Ile Leu Asp Gly Phe Pro Lys Asp Val Asp Leu Asn Gln Ser Arg Lys
            100                 105                 110

Gly Arg Lys Pro Leu Ala Gly Pro Lys Ala Ala Val Leu Pro Pro Arg
        115                 120                 125

Pro Pro Thr Lys Arg Lys Ala Leu Glu Glu Pro Arg Ala Thr Pro Pro
    130                 135                 140

Ala Thr Leu Ala Ser Lys Ser Val Ser Ser Pro Gly Ser His Leu Lys
145                 150                 155                 160

Thr Lys Pro Pro Lys Lys Pro Asp Gly Asn Leu Glu Ser Gln His Leu
                165                 170                 175

Pro Leu Gly Asn Gly Ile Gln Thr Met Ala Ala Ser Val Gln Arg Ala
            180                 185                 190

Val Thr Val Ala Ser Gly Asp Val Pro Gly Thr Arg Gly Ala Val Glu
        195                 200                 205

Gly Ile Leu Ile Gln Gln Val Phe Glu Ser Gly Arg Ser Lys Lys Cys
    210                 215                 220

Ile Gln Val Gly Gly Glu Phe Tyr Thr Pro Asn Lys Phe Glu Asp Pro
225                 230                 235                 240

Ser Gly Asn Leu Lys Asn Lys Ala Arg Ser Gly Ser Ser Leu Lys Pro
                245                 250                 255

Val Val Arg Ala Lys Gly Ala Gln Val Thr Ile Pro Gly Arg Asp Glu
            260                 265                 270

Gln Lys Val Gly Gln Gln Cys Gly Val Pro Pro Leu Pro Ser Leu Pro
        275                 280                 285

Ser Glu Pro Gln Val Asn Gln Lys Asn Glu Asp Glu Cys Ala Val Cys
    290                 295                 300

His Asp Gly Gly Glu Leu Ile Cys Cys Asp Gly Cys Pro Arg Ala Phe
305                 310                 315                 320

His Leu Ala Cys Leu Ser Pro Pro Leu Gln Glu Ile Pro Ser Gly Leu
                325                 330                 335
```

-continued

```
Trp Arg Cys Ser Cys Cys Leu Gln Gly Arg Val Gln Gln Asn Leu Ser
            340                 345                 350

Gln Pro Glu Val Ser Arg Pro Glu Leu Pro Ala Glu Thr Pro Ile
            355                 360                 365

Leu Val Gly Leu Arg Ser Ala Ser Glu Lys Thr Arg Gly Pro Ser Arg
            370                 375                 380

Glu Leu Lys Ala Ser Ser Asp Ala Ala Val Thr Tyr Val Asn Leu Leu
385                 390                 395                 400

Ala Pro His Pro Ala Ala Pro Leu Leu Glu Pro Ser Ala Leu Cys Pro
                405                 410                 415

Leu Leu Ser Ala Gly Asn Glu Gly Arg Pro Gly Pro Ala Pro Ser Ala
            420                 425                 430

Arg Cys Ser Val Cys Gly Asp Gly Thr Glu Val Leu Arg Cys Ala His
            435                 440                 445

Cys Ala Ala Ala Phe His Trp Arg Cys His Phe Pro Thr Ala Ala Ala
    450                 455                 460

Arg Pro Gly Thr Asn Leu Arg Cys Lys Ser Cys Ser Ala Asp Ser Thr
465                 470                 475                 480

Pro Thr Pro Gly Thr Pro Gly Glu Ala Val Pro Thr Ser Gly Pro Arg
                485                 490                 495

Pro Ala Pro Gly Leu Ala Lys Val Gly Asp Asp Ser Ala Ser His Asp
            500                 505                 510

Pro Val Leu His Arg Asp Asp Leu Glu Ser Leu Leu Asn Glu His Ser
            515                 520                 525

Phe Asp Gly Ile Leu Gln Trp Ala Ile Gln Ser Met Ser Arg Pro Leu
    530                 535                 540

Ala Glu Thr Pro Pro Phe Ser Ser
545                 550

<210> SEQ ID NO 8
<211> LENGTH: 545
<212> TYPE: PRT
<213> ORGANISM: Homo sapiens

<400> SEQUENCE: 8

Met Ala Thr Asp Ala Ala Leu Arg Arg Leu Leu Arg Leu His Arg Thr
1               5                   10                  15

Glu Ile Ala Val Ala Val Asp Ser Ala Phe Pro Leu Leu His Ala Leu
            20                  25                  30

Ala Asp His Asp Val Val Pro Glu Asp Lys Phe Gln Glu Thr Leu His
            35                  40                  45

Leu Lys Glu Lys Glu Gly Cys Pro Gln Ala Phe His Ala Leu Leu Ser
        50                  55                  60

Trp Leu Leu Thr Gln Asp Ser Thr Ala Ile Leu Asp Phe Trp Arg Val
65                  70                  75                  80

Leu Phe Lys Asp Tyr Asn Leu Glu Arg Tyr Gly Arg Leu Gln Pro Ile
                85                  90                  95

Leu Asp Ser Phe Pro Lys Asp Val Asp Leu Ser Gln Pro Arg Lys Gly
            100                 105                 110

Arg Lys Pro Pro Ala Val Pro Lys Ala Leu Val Pro Pro Arg Leu
            115                 120                 125

Pro Thr Lys Arg Lys Ala Ser Glu Glu Ala Arg Ala Ala Pro Ala
    130                 135                 140

Ala Leu Thr Pro Arg Gly Thr Ala Ser Pro Gly Ser Gln Leu Lys Ala
```

-continued

```
            145                 150                 155                 160
Lys Pro Pro Lys Lys Pro Glu Ser Ser Ala Glu Gln Gln Arg Leu Pro
                165                 170                 175
Leu Gly Asn Gly Ile Gln Thr Met Ser Ala Ser Val Gln Arg Ala Val
            180                 185                 190
Ala Met Ser Ser Gly Asp Val Pro Gly Ala Arg Gly Ala Val Glu Gly
        195                 200                 205
Ile Leu Ile Gln Gln Val Phe Glu Ser Gly Ser Lys Lys Cys Ile
    210                 215                 220
Gln Val Gly Gly Glu Phe Tyr Thr Pro Ser Lys Phe Glu Asp Ser Gly
225                 230                 235                 240
Ser Gly Lys Asn Lys Ala Arg Ser Ser Ser Gly Pro Lys Pro Leu Val
                245                 250                 255
Arg Ala Lys Gly Ala Gln Gly Ala Ala Pro Gly Gly Gly Glu Ala Arg
            260                 265                 270
Leu Gly Gln Gln Gly Ser Val Pro Ala Pro Leu Ala Leu Pro Ser Asp
        275                 280                 285
Pro Gln Leu His Gln Lys Asn Glu Asp Glu Cys Ala Val Cys Arg Asp
    290                 295                 300
Gly Gly Glu Leu Ile Cys Cys Asp Gly Cys Pro Arg Ala Phe His Leu
305                 310                 315                 320
Ala Cys Leu Ser Pro Pro Leu Arg Glu Ile Pro Ser Gly Thr Trp Arg
                325                 330                 335
Cys Ser Ser Cys Leu Gln Ala Thr Val Gln Glu Val Gln Pro Arg Ala
            340                 345                 350
Glu Glu Pro Arg Pro Gln Glu Pro Val Glu Thr Pro Leu Pro Pro
        355                 360                 365
Gly Leu Arg Ser Ala Gly Glu Glu Val Arg Gly Pro Pro Gly Glu Pro
    370                 375                 380
Leu Ala Gly Met Asp Thr Thr Leu Val Tyr Lys His Leu Pro Ala Pro
385                 390                 395                 400
Pro Ser Ala Ala Pro Leu Pro Gly Leu Asp Ser Ser Ala Leu His Pro
                405                 410                 415
Leu Leu Cys Val Gly Pro Glu Gly Gln Gln Asn Leu Ala Pro Gly Ala
            420                 425                 430
Arg Cys Gly Val Cys Gly Asp Gly Thr Asp Val Leu Arg Cys Thr His
        435                 440                 445
Cys Ala Ala Ala Phe His Trp Arg Cys His Phe Pro Ala Gly Thr Ser
    450                 455                 460
Arg Pro Gly Thr Gly Leu Arg Cys Arg Ser Cys Ser Gly Asp Val Thr
465                 470                 475                 480
Pro Ala Pro Val Glu Gly Val Leu Ala Pro Ser Pro Ala Arg Leu Ala
                485                 490                 495
Pro Gly Pro Ala Lys Asp Asp Thr Ala Ser His Glu Pro Ala Leu His
            500                 505                 510
Arg Asp Asp Leu Glu Ser Leu Leu Ser Glu His Thr Phe Asp Gly Ile
        515                 520                 525
Leu Gln Trp Ala Ile Gln Ser Met Ala Arg Pro Ala Ala Pro Phe Pro
    530                 535                 540
Ser
545

<210> SEQ ID NO 9
```

```
<211> LENGTH: 552
<212> TYPE: PRT
<213> ORGANISM: Murine

<400> SEQUENCE: 9

Met Ala Gly Gly Asp Gly Met Leu Arg Arg Leu Leu Arg Leu His Arg
1               5                   10                  15

Thr Glu Ile Ala Val Ala Ile Asp Ser Ala Phe Pro Leu Leu His Ala
                20                  25                  30

Leu Ala Asp His Asp Val Val Pro Glu Asp Lys Phe Gln Glu Thr Leu
            35                  40                  45

Arg Leu Lys Glu Lys Glu Gly Cys Pro Gln Ala Phe His Ala Leu Leu
    50                  55                  60

Ser Trp Leu Leu Thr Arg Asp Ser Gly Ala Ile Leu Asp Phe Trp Arg
65                  70                  75                  80

Ile Leu Phe Lys Asp Tyr Asn Leu Glu Arg Tyr Ser Arg Leu His Ser
                85                  90                  95

Ile Leu Asp Gly Phe Pro Lys Asp Val Asp Leu Asn Gln Ser Arg Lys
            100                 105                 110

Gly Arg Lys Pro Leu Ala Gly Pro Lys Ala Ala Val Leu Pro Pro Arg
    115                 120                 125

Pro Pro Thr Lys Arg Lys Ala Leu Glu Glu Pro Arg Ala Thr Pro Pro
130                 135                 140

Ala Thr Leu Ala Ser Lys Ser Val Ser Ser Pro Gly Ser His Leu Lys
145                 150                 155                 160

Thr Lys Pro Pro Lys Lys Pro Asp Gly Asn Leu Glu Ser Gln His Leu
                165                 170                 175

Pro Leu Gly Asn Gly Ile Gln Thr Met Ala Ala Ser Val Gln Arg Ala
            180                 185                 190

Val Thr Val Ala Ser Gly Asp Val Pro Gly Thr Arg Gly Ala Val Glu
    195                 200                 205

Gly Ile Leu Ile Gln Gln Val Phe Glu Ser Gly Arg Ser Lys Lys Cys
210                 215                 220

Ile Gln Val Gly Gly Glu Phe Tyr Thr Pro Asn Lys Phe Glu Asp Pro
225                 230                 235                 240

Ser Gly Asn Leu Lys Asn Lys Ala Arg Ser Gly Ser Ser Leu Lys Pro
                245                 250                 255

Val Val Arg Ala Lys Gly Ala Gln Val Thr Ile Pro Gly Arg Asp Glu
            260                 265                 270

Gln Lys Val Gly Gln Gln Cys Gly Val Pro Leu Pro Ser Leu Pro
    275                 280                 285

Ser Glu Pro Gln Val Asn Gln Lys Asn Glu Asp Glu Cys Ala Val Cys
290                 295                 300

His Asp Gly Gly Glu Leu Ile Cys Cys Asp Gly Cys Pro Arg Ala Phe
305                 310                 315                 320

His Leu Ala Cys Leu Ser Pro Pro Leu Gln Glu Ile Pro Ser Gly Leu
                325                 330                 335

Trp Arg Cys Ser Cys Cys Leu Gln Gly Arg Val Gln Gln Asn Leu Ser
            340                 345                 350

Gln Pro Glu Val Ser Arg Pro Glu Leu Pro Ala Glu Thr Pro Ile
    355                 360                 365

Leu Val Gly Leu Arg Ser Ala Ser Glu Lys Thr Arg Gly Pro Ser Arg
370                 375                 380

Glu Leu Lys Ala Ser Ser Asp Ala Ala Val Thr Tyr Val Asn Leu Leu
```

-continued

```
                385                 390                 395                 400
Ala Pro His Pro Ala Pro Leu Leu Glu Pro Ser Ala Leu Cys Pro
            405                 410                 415
Leu Leu Ser Ala Gly Asn Glu Gly Arg Pro Gly Pro Ala Pro Ser Ala
            420                 425                 430
Arg Cys Ser Val Cys Gly Asp Gly Thr Glu Val Leu Arg Cys Ala His
            435                 440                 445
Cys Ala Ala Phe His Trp Arg Cys His Phe Pro Thr Ala Ala Ala
    450                 455                 460
Arg Pro Gly Thr Asn Leu Arg Cys Lys Ser Cys Ser Ala Asp Ser Thr
465                 470                 475                 480
Pro Thr Pro Gly Thr Pro Gly Glu Ala Val Pro Thr Ser Gly Pro Arg
            485                 490                 495
Pro Ala Pro Gly Leu Ala Lys Val Gly Asp Ser Ala Ser His Asp
            500                 505                 510
Pro Val Leu His Arg Asp Asp Leu Glu Ser Leu Leu Asn Glu His Ser
            515                 520                 525
Phe Asp Gly Ile Leu Gln Trp Ala Ile Gln Ser Met Ser Arg Pro Leu
    530                 535                 540
Ala Glu Thr Pro Pro Phe Ser Ser
545                 550

<210> SEQ ID NO 10
<211> LENGTH: 550
<212> TYPE: PRT
<213> ORGANISM: Artificial Sequence
<220> FEATURE:
<223> OTHER INFORMATION: Consensus sequence of SEQ ID NO:8 & SEQ ID
      NO:10
<220> FEATURE:
<221> NAME/KEY: MISC_FEATURE
<222> LOCATION: (1)..(550)
<223> OTHER INFORMATION: Xaa denotes mismatch of SEQ ID NO:8 & SEQ ID
      NO:9

<400> SEQUENCE: 10

Xaa Xaa Xaa Asp Xaa Xaa Leu Arg Arg Leu Leu Arg Leu His Arg Thr
1               5                   10                  15
Glu Ile Ala Val Ala Xaa Asp Ser Ala Phe Pro Leu Leu His Ala Leu
            20                  25                  30
Ala Asp His Asp Val Val Pro Glu Asp Lys Phe Gln Glu Thr Leu Xaa
        35                  40                  45
Leu Lys Glu Lys Glu Gly Cys Pro Gln Ala Phe His Ala Leu Leu Ser
    50                  55                  60
Trp Leu Leu Thr Xaa Asp Ser Xaa Ala Ile Leu Asp Phe Trp Arg Xaa
65                  70                  75                  80
Leu Phe Lys Asp Tyr Asn Leu Glu Arg Tyr Xaa Arg Leu Xaa Xaa Ile
            85                  90                  95
Leu Asp Xaa Phe Pro Lys Asp Val Asp Leu Xaa Gln Xaa Arg Lys Gly
            100                 105                 110
Arg Lys Pro Xaa Ala Xaa Pro Lys Ala Xaa Val Xaa Pro Arg Xaa
        115                 120                 125
Pro Thr Lys Arg Lys Ala Xaa Glu Glu Xaa Arg Ala Xaa Xaa Pro Ala
        130                 135                 140
Xaa Leu Xaa Xaa Xaa Xaa Xaa Xaa Ser Pro Gly Ser Xaa Leu Lys Xaa
145                 150                 155                 160
Lys Pro Pro Lys Lys Pro Xaa Xaa Xaa Xaa Glu Xaa Gln Xaa Leu Pro
```

-continued

```
            165                 170                 175
Leu Gly Asn Gly Ile Gln Thr Met Xaa Ala Ser Val Gln Arg Ala Val
        180                 185                 190

Xaa Xaa Xaa Ser Gly Asp Val Pro Gly Xaa Arg Gly Ala Val Glu Gly
        195                 200                 205

Ile Leu Ile Gln Gln Val Phe Glu Ser Gly Xaa Ser Lys Lys Cys Ile
        210                 215                 220

Gln Val Gly Gly Glu Phe Tyr Thr Pro Xaa Lys Phe Glu Asp Xaa Ser
225                 230                 235                 240

Gly Xaa Xaa Lys Asn Lys Ala Arg Ser Xaa Ser Xaa Xaa Lys Pro Xaa
            245                 250                 255

Val Arg Ala Lys Gly Ala Gln Xaa Xaa Xaa Pro Gly Xaa Xaa Glu Xaa
            260                 265                 270

Xaa Xaa Gly Gln Gln Xaa Xaa Val Pro Xaa Xaa Xaa Leu Pro Ser
            275                 280                 285

Xaa Pro Gln Xaa Xaa Gln Lys Asn Glu Asp Glu Cys Ala Val Cys Xaa
            290                 295                 300

Asp Gly Gly Glu Leu Ile Cys Cys Asp Gly Cys Pro Arg Ala Phe His
305                 310                 315                 320

Leu Ala Cys Leu Ser Pro Leu Xaa Glu Ile Pro Ser Gly Xaa Trp
            325                 330                 335

Arg Cys Ser Xaa Cys Leu Gln Xaa Xaa Val Gln Xaa Xaa Xaa Xaa
            340                 345                 350

Xaa Glu Xaa Xaa Arg Pro Xaa Glu Xaa Pro Xaa Glu Thr Pro Xaa Xaa
            355                 360                 365

Xaa Gly Leu Arg Ser Ala Xaa Glu Xaa Xaa Arg Gly Pro Xaa Xaa Glu
            370                 375                 380

Xaa Xaa Ala Xaa Xaa Asp Xaa Xaa Xaa Tyr Xaa Xaa Leu Xaa Ala
385                 390                 395                 400

Pro Xaa Xaa Ala Ala Pro Leu Xaa Xaa Leu Xaa Xaa Ser Ala Leu Xaa
            405                 410                 415

Pro Leu Leu Xaa Xaa Gly Xaa Glu Gly Xaa Xaa Xaa Xaa Ala Pro Xaa
            420                 425                 430

Ala Arg Cys Xaa Val Cys Gly Asp Gly Thr Xaa Val Leu Arg Cys Xaa
            435                 440                 445

His Cys Ala Ala Ala Phe His Trp Arg Cys His Phe Pro Xaa Xaa Xaa
            450                 455                 460

Xaa Arg Pro Gly Thr Xaa Leu Arg Cys Xaa Ser Cys Ser Xaa Asp Xaa
465                 470                 475                 480

Thr Pro Xaa Pro Xaa Xaa Xaa Gly Xaa Xaa Xaa Pro Xaa Ser Xaa Xaa
            485                 490                 495

Arg Xaa Ala Pro Gly Xaa Ala Lys Xaa Xaa Asp Asp Xaa Ala Ser His
            500                 505                 510

Xaa Pro Xaa Leu His Arg Asp Asp Leu Glu Ser Leu Leu Xaa Glu His
            515                 520                 525

Xaa Phe Asp Gly Ile Leu Gln Trp Ala Ile Gln Ser Met Xaa Arg Pro
            530                 535                 540

Xaa Ala Xaa Xaa Pro Xaa
545                 550

<210> SEQ ID NO 11
<211> LENGTH: 48
<212> TYPE: DNA
<213> ORGANISM: Mouse
```

-continued

<400> SEQUENCE: 11
ggggcctcga tggacgtctc tggggcccag gtcgtggttc gcgcgcta          48

<210> SEQ ID NO 12
<211> LENGTH: 15
<212> TYPE: PRT
<213> ORGANISM: Mouse

<400> SEQUENCE: 12

Pro Glu Leu Pro Ala Glu Thr Pro Gly Pro Ala Pro Ser Ala Arg
1               5                   10                  15

<210> SEQ ID NO 13
<211> LENGTH: 43
<212> TYPE: DNA
<213> ORGANISM: Mouse

<400> SEQUENCE: 13
agtgagcccc aggttaacca gaacgaggat gagtgtgccg tgt               43

<210> SEQ ID NO 14
<211> LENGTH: 14
<212> TYPE: PRT
<213> ORGANISM: Mouse

<400> SEQUENCE: 14

Ser Glu Pro Gln Val Asn Gln Asn Glu Asp Glu Cys Ala Val
1               5                   10

<210> SEQ ID NO 15
<211> LENGTH: 48
<212> TYPE: DNA
<213> ORGANISM: Mouse

<400> SEQUENCE: 15
gtcaccaggc tcggttccct cgggtcccat ctctactcgt ctttcacc          48

<210> SEQ ID NO 16
<211> LENGTH: 15
<212> TYPE: PRT
<213> ORGANISM: Mouse

<400> SEQUENCE: 16

Val Val Arg Ala Lys Gly Ala Gln Gly Arg Asp Glu Gln Lys Val
1               5                   10                  15

<210> SEQ ID NO 17
<211> LENGTH: 20
<212> TYPE: DNA
<213> ORGANISM: Artificial sequence
<220> FEATURE:
<223> OTHER INFORMATION: PCR primer

<400> SEQUENCE: 17
agaagtgcat ccaggttggc                                         20

<210> SEQ ID NO 18
<211> LENGTH: 20
<212> TYPE: DNA
<213> ORGANISM: Artificial sequence
<220> FEATURE:
<223> OTHER INFORMATION: PCR primer

<400> SEQUENCE: 18
ggaagagggg cgtcagcaat                                             20

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Met Ala Thr Asp Ala Ala Leu Arg Arg Leu Leu Arg Leu His Arg
1               5                  10                  15

<210> SEQ ID NO 20
<211> LENGTH: 14
<212> TYPE: PRT
<213> ORGANISM: Artificial Sequence
<220> FEATURE:
<223> OTHER INFORMATION: Synthetic peptide

<400> SEQUENCE: 20

Ser Gln Pro Arg Lys Gly Arg Lys Pro Pro Ala Val Pro Lys
1               5                  10

<210> SEQ ID NO 21
<211> LENGTH: 19
<212> TYPE: DNA
<213> ORGANISM: Artificial Sequence
<220> FEATURE:
<223> OTHER INFORMATION: B127FR4-29 primer for PCR

<400> SEQUENCE: 21
gctctggatg gcctactgc                                              19

<210> SEQ ID NO 22
<211> LENGTH: 20
<212> TYPE: DNA
<213> ORGANISM: Artificial Sequence
<220> FEATURE:
<223> OTHER INFORMATION: B127FR4-17 primer for PCR

<400> SEQUENCE: 22
agaagtgcat ccaggttggc                                             20

<210> SEQ ID NO 23
<211> LENGTH: 19
<212> TYPE: DNA
<213> ORGANISM: Artificial Sequence
<220> FEATURE:
<223> OTHER INFORMATION: B127FR4-33 primer for PCR

<400> SEQUENCE: 23
gtgtgctcgc tcagaaggg                                              19

<210> SEQ ID NO 24
<211> LENGTH: 18
<212> TYPE: DNA
<213> ORGANISM: Artificial Sequence
<220> FEATURE:
<223> OTHER INFORMATION: Forward primer Mforw4 for PCR

<400> SEQUENCE: 24
tggcaggtgg ggatggaa                                               18

<210> SEQ ID NO 25

```
<211> LENGTH: 20
<212> TYPE: DNA
<213> ORGANISM: Artificial Sequence
<220> FEATURE:
<223> OTHER INFORMATION: Reverse primer Mrev15 for PCR

<400> SEQUENCE: 25
ggagggatgg aagggagga                                           20

<210> SEQ ID NO 26
<211> LENGTH: 19
<212> TYPE: DNA
<213> ORGANISM: Artificial Sequence
<220> FEATURE:
<223> OTHER INFORMATION: Forward primer Mforw2 for PCR

<400> SEQUENCE: 26
tcccacctga agactaagc                                           19

<210> SEQ ID NO 27
<211> LENGTH: 20
<212> TYPE: DNA
<213> ORGANISM: Artificial Sequence
<220> FEATURE:
<223> OTHER INFORMATION: Reverse primer Mrev32 for PCR

<400> SEQUENCE: 27
tcacagctct ctggacagaa                                          20

<210> SEQ ID NO 28
<211> LENGTH: 18
<212> TYPE: DNA
<213> ORGANISM: Artificial Sequence
<220> FEATURE:
<223> OTHER INFORMATION: Primer B127FR4-21 for PCR

<400> SEQUENCE: 28
ggcttctgag gctgcacc                                            18

<210> SEQ ID NO 29
<211> LENGTH: 8
<212> TYPE: PRT
<213> ORGANISM: Artificial Sequence
<220> FEATURE:
<223> OTHER INFORMATION: Double-paired finger motif

<400> SEQUENCE: 29

Cys Cys Cys Cys His Cys Cys Cys
1               5

<210> SEQ ID NO 30
<211> LENGTH: 42
<212> TYPE: PRT
<213> ORGANISM: Artificial Sequence
<220> FEATURE:
<223> OTHER INFORMATION: Structural motiff
<220> FEATURE:
<221> NAME/KEY: MISC_FEATURE
<222> LOCATION: (1)..(42)
<223> OTHER INFORMATION: Xaa is any amino acid

<400> SEQUENCE: 30
```

```
                                            -continued
Cys Xaa Xaa Cys Xaa Xaa Xaa Xaa Xaa Xaa Xaa Cys Xaa Xaa Cys
1               5                   10              15

Xaa Xaa Xaa Xaa His Xaa Xaa Cys Xaa Xaa Xaa Xaa Xaa Xaa Xaa
            20              25              30

Xaa Xaa Xaa Xaa Xaa Xaa Cys Xaa Xaa Cys
        35              40
```